US007741046B2

(12) United States Patent
Larsen et al.

(10) Patent No.: US 7,741,046 B2
(45) Date of Patent: *Jun. 22, 2010

(54) SEQUENTIAL ANALYSIS OF BIOLOGICAL SAMPLES

(75) Inventors: Melinda Larsen, Albany, NY (US); Anup Sood, Clifton Park, NY (US); Michael J. Gerdes, Albany, NY (US); Michael Christopher Montalto, Albany, NY (US); Zhengyu Pang, Clifton Park, NY (US); Fiona Ginty, Saratoga Springs, NY (US)

(73) Assignee: General Electric Company, Niskayuna, NY (US)

( * ) Notice: Subject to any disclaimer, the term of this patent is extended or adjusted under 35 U.S.C. 154(b) by 207 days.

This patent is subject to a terminal disclaimer.

(21) Appl. No.: 11/864,093

(22) Filed: Sep. 28, 2007

(65) Prior Publication Data

US 2008/0118944 A1 May 22, 2008

Related U.S. Application Data

(63) Continuation-in-part of application No. 11/560,599, filed on Nov. 16, 2006, now Pat. No. 7,629,125.

(51) Int. Cl.
*C12Q 1/68* (2006.01)
*G01N 33/53* (2006.01)

(52) U.S. Cl. .......................................... 435/6; 435/7.1
(58) Field of Classification Search ........................ None
See application file for complete search history.

(56) References Cited

U.S. PATENT DOCUMENTS

| 6,083,486 | A | 7/2000 | Weissleder et al. |
|---|---|---|---|
| 6,150,173 | A | 11/2000 | Schubert et al. |
| 6,534,041 | B1 | 3/2003 | Licha et al. |
| 6,833,246 | B2 | 12/2004 | Balasubramanian et al. |
| 6,924,115 | B2 | 8/2005 | Schubert et al. |
| 2002/0106648 | A1 | 8/2002 | Lizardi et al. |
| 2002/0173053 | A1 | 11/2002 | Damaj et al. |
| 2002/0177149 | A1 | 11/2002 | Rimm et al. |
| 2003/0044353 | A1 | 3/2003 | Weissleder et al. |
| 2003/0064398 | A1 | 4/2003 | Barnes et al. |
| 2003/0073149 | A1 | 4/2003 | Archer et al. |
| 2004/0121382 | A1 | 6/2004 | Lie et al. |
| 2004/0248325 | A1 | 12/2004 | Bukusoglu et al. |
| 2005/0169843 | A1 | 8/2005 | Weissleder et al. |
| 2005/0171434 | A1 | 8/2005 | Madden et al. |
| 2007/0099208 | A1* | 5/2007 | Drmanac et al. ............... 435/6 |

FOREIGN PATENT DOCUMENTS

| DE | 4421891 | 1/1996 |
|---|---|---|
| WO | WO0003034 | 1/2000 |
| WO | WO0020641 | 4/2000 |
| WO | WO 0058507 A1 | 10/2000 |
| WO | WO02079771 | 10/2002 |
| WO | WO2005017485 | 2/2005 |

OTHER PUBLICATIONS

PCT Search Report—Nov. 15, 2007.
Segal et al., "Decomposition of Pinacyanol chloride Dye Using Several Manganese Oxide Catalysts", Chem. Mater, vol. 9, pp. 2526-2532 (1997).
Wahlby et al., "Sequential immunofluorescense staining and image analysis for detection of large number of amtigens in individual cell nuclei", Cytometry, vol. 47, pp. 32-41 (2002).
Mittag et al., "Sequential photobleaching of fluorochromes for polychromatic slide-based cytometry", Cytometry Part A, vol. 69A, pp. 139-141 (2006).
Laffers et al., "Iterative restaining as a pivotal tool for n-color immunophenotyping by Iside-based cytometry", Cytometry Part A, vol. 69A, pp. 127-130 (2006).
Masseyeff, Methods of Immunological Analysis, vol. 3, 1993, XP002503445, pp. 318-319.
PCT Search Report Jan. 12, 2008.
PCT Search Report Nov. 25, 2008.
PCT Search Report Nov. 28, 2008.

* cited by examiner

*Primary Examiner*—Kenneth R. Horlick
*Assistant Examiner*—David C Thomas
(74) *Attorney, Agent, or Firm*—Jenifer E. Haeckl

(57) ABSTRACT

Methods for probing multiple targets in a biological sample are provided. The methods include the steps of providing a biological sample containing multiple targets adhered to a solid support, binding at least one fluorescent probe to one or more target present in the sample, and observing a signal from the fluorescent probe. The method further includes the steps of oxidizing the bound fluorescent probe with a solution containing an oxidizing agent that substantially inactivates the fluorescent probe, binding at least one fluorescent probe to one or more target present in the sample, and observing a signal from the fluorescent probe. The methods disclosed herein also provide for multiple iterations of binding, observing, and oxidizing for deriving information about multiple targets in a single sample. An associated kit is also provided.

24 Claims, 36 Drawing Sheets

SAMPLE 23A
DAPI channel

SAMPLE 23A
Cy3 channel

SAMPLE 23B

SAMPLE 23D

SAMPLE 23C

SAMPLE 23E

SAMPLE 24A SAMPLE 24B

SAMPLE 24C SAMPLE 24D

SAMPLE 24E SAMPLE 24F

SAMPLE 30B

SAMPLE 30D

SAMPLE 30A

SAMPLE 30C

SAMPLE 30F

SAMPLE 30D

SAMPLE 30E

SAMPLE 30C

US 7,741,046 B2

SEQUENTIAL ANALYSIS OF BIOLOGICAL SAMPLES

CROSS REFERENCE TO RELATED APPLICATIONS

This application is a continuation-in-part of U.S. patent application Ser. No. 11/560,599, entitled "Sequential Analysis of Biological Samples", filed Nov. 16, 2006, which is incorporated herein by reference.

BACKGROUND

Disclosed herein are methods for sequentially analyzing a biological sample to discern inter alia the presence, absence, concentration, and/or spatial distribution of multiple biological targets in a biological sample.

Various methods may be used in biology and in medicine to observe different targets in a biological sample. For example, analysis of proteins in histological sections and other cytological preparations may be performed using the techniques of histochemistry, immunohistochemistry (IHC), or immunofluorescence. Analysis of proteins in biological samples may also be performed using solid-state immunoassays, for example, using the techniques of western blots.

Many of the current techniques may detect only a few targets at one time (such as, IHC or fluorescence-based western blots where number of targets detectable is limited by the fluorescence-based detection system) in a single sample. Further analysis of targets may require use of additional biological samples from the source limiting the ability to determine relative characteristics of the targets such as the presence, absence, concentration, and/or the spatial distribution of multiple biological targets in the biological sample. Moreover, in certain instances, a limited amount of sample may be available for analysis or the individual sample may require further analysis. Thus, methods, agents, and devices capable of iteratively analyzing an individual sample are needed.

BRIEF DESCRIPTION

In some embodiments, methods of detecting multiple targets in a biological sample are provided. The methods include the steps of providing a biological sample containing multiple targets adhered to a solid support, binding at least one fluorescent probe to one or more target present in the sample, and observing a signal from the fluorescent probe. The method further includes the steps of oxidizing the bound fluorescent probe with a solution containing an oxidizing agent that substantially inactivates the fluorescent probe, binding at least one fluorescent probe to one or more target present in the sample, and observing a signal from the fluorescent probe. The process of binding, observing and oxidizing may be iteratively repeated.

In some embodiments, the methods include the steps of providing a biological sample containing multiple targets adhered to a membrane, binding at least one fluorescent probe to one or more target present in the sample, and observing a signal from the fluorescent probe. The method further includes the steps of oxidizing the bound fluorescent probe with a solution containing an oxidizing agent that substantially inactivates the fluorescent probe, binding at least one fluorescent probe to one or more target present in the sample, and observing a signal from the fluorescent probe. The process of binding, observing and oxidizing may be iteratively repeated.

In some embodiments, kits for detection of multiple targets in a biological sample are provided. The kits include multiple probes having a binder coupled to a fluorescent signal generator. An oxidizing agent when applied to the sample substantially inactivates the fluorescent signal generator.

DETAILED DESCRIPTION

Figure 1:
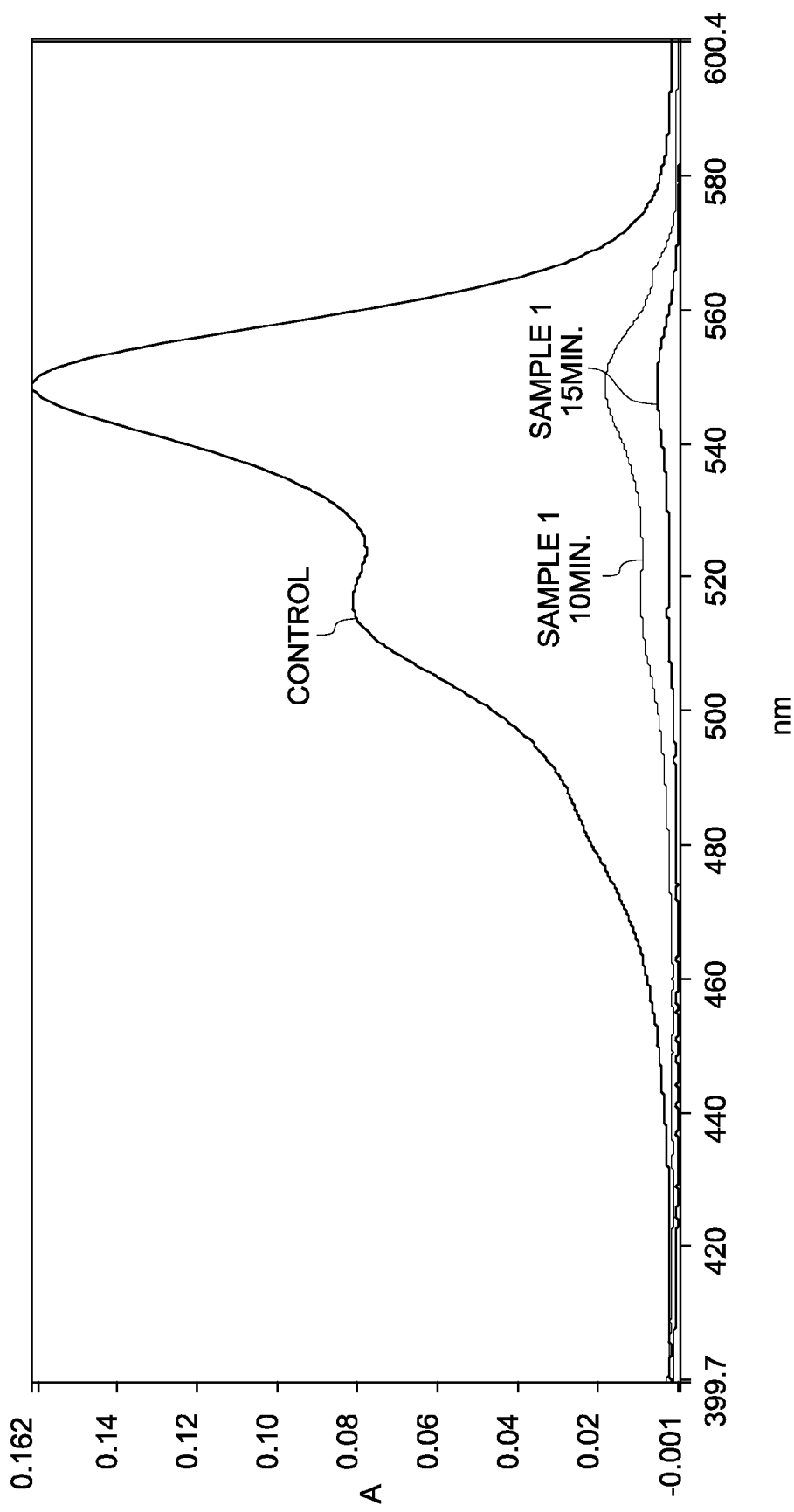
FIG. 1 shows the absorbance spectra of Sample 1 as a function of wavelength, after 10 minutes and 15 minutes.

To more clearly and concisely describe and point out the subject matter of the claimed invention, the following definitions are provided for specific terms, which are used in the following description and the appended claims.

The singular forms "a" "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least each numerical parameter should at least be construed in light of the number of reported significant digits and by applying ordinary rounding techniques.

DEFINITIONS

To more clearly and concisely describe and point out the subject matter of the claimed invention, the following definitions are provided for specific terms that are used in the following description and the claims appended hereto.

As used herein, the term "antibody" refers to an immunoglobulin that specifically binds to and is thereby defined as complementary with a particular spatial and polar organization of another molecule. The antibody may be monoclonal or polyclonal and may be prepared by techniques that are well known in the art such as immunization of a host and collection of sera (polyclonal), or by preparing continuous hybrid cell lines and collecting the secreted protein (monoclonal), or by cloning and expressing nucleotide sequences or mutagenized versions thereof, coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM. Functional antibody fragments may include portions of an antibody capable of retaining binding at similar affinity to full-length antibody (for example, Fab, Fv and F(ab')$_2$, or Fab'). In addition, aggregates, polymers, and conjugates of immunoglobulins or their fragments may be used where appropriate so long as binding affinity for a particular molecule is substantially maintained.

As used herein, the term "binder" refers to a molecule that may bind to one or more targets in the biological sample. A binder may specifically bind to a target. Suitable binders may include one or more of natural or modified peptides, proteins (e.g., antibodies, affibodies, or aptamers), nucleic acids (e.g., polynucleotides, DNA, RNA, or aptamers); polysaccharides (e.g., lectins, sugars), lipids, enzymes, enzyme substrates or inhibitors, ligands, receptors, antigens, or haptens. A suitable binder may be selected depending on the sample to be analyzed and the targets available for detection. For example, a target in the sample may include a ligand and the binder may include a receptor or a target may include a receptor and the binder may include a ligand. Similarly, a target may include an antigen and the binder may include an antibody or antibody fragment or vice versa. In some embodiments, a target may include a nucleic acid and the binder may include a complementary nucleic acid. In some embodiments, both the target and the binder may include proteins capable of binding to each other.

As used herein, the term "biological sample" refers to a sample obtained from a biological subject, including sample of biological tissue or fluid origin obtained in vivo or in vitro. Such samples can be, but are not limited to, body fluid (e.g., blood, blood plasma, serum, or urine), organs, tissues, fractions, and cells isolated from mammals including, humans. Biological samples also may include sections of the biological sample including tissues (e.g., sectional portions of an organ or tissue). Biological samples may also include extracts from a biological sample, for example, an antigen from a biological fluid (e.g., blood or urine).

A biological sample may be of prokaryotic origin or eukaryotic origin (e.g., insects, protozoa, birds, fish, reptiles). In some embodiments, the biological sample is mammalian (e.g., rat, mouse, cow, dog, donkey, guinea pig, or rabbit). In certain embodiments, the biological sample is of primate origin (e.g., example, chimpanzee, or human).

As used herein, the term "control probe" refers to an agent having a binder coupled to a signal generator or a signal generator capable of staining directly, such that the signal generator retains at least 80 percent signal after contact with a solution of an oxidizing agent employed to inactivate the fluorescent probe. A suitable signal generator in a control probe is not substantially oxidized or substantially inactivated when contacted with the oxidizing agent. Suitable examples of signal generators may include a radioactive label or a non-oxidizable fluorophore (e.g., DAPI)

As used herein, the term "enzyme" refers to a protein molecule that can catalyze a chemical reaction of a substrate. In some embodiments, a suitable enzyme catalyzes a chemical reaction of the substrate to form a reaction product that can bind to a receptor (e.g., phenolic groups) present in the sample or a solid support to which the sample is bound. A receptor may be exogeneous (that is, a receptor extrinsically adhered to the sample or the solid-support) or endogeneous (receptors present intrinsically in the sample or the solid-support). Examples of suitable enzymes include peroxidases, oxidases, phosphatases, esterases, and glycosidases. Specific examples of suitable enzymes include horseradish peroxidase, alkaline phosphatase, β-D-galactosidase, lipase, and glucose oxidase.

As used herein, the term "enzyme substrate" refers to a chemical compound that is chemically catalyzed by an enzyme to form a reaction product. In some embodiments, the reaction product is capable of binding to a receptor present in the sample or a solid support to which the sample is bound. In some embodiments, enzyme substrates employed in the methods herein may include non-chromogenic or non-chemiluminescent substrates. A signal generator may be attached to the enzyme substrate as a label.

As used herein, the term "fluorophore" or "fluorescent signal generator" refers to a chemical compound, which when excited by exposure to a particular wavelength of light, emits light at a different wavelength. Fluorophores may be described in terms of their emission profile, or "color." Green fluorophores (for example Cy3, FITC, and Oregon Green) may be characterized by their emission at wavelengths generally in the range of 515-540 nanometers. Red fluorophores (for example Texas Red, Cy5, and tetramethylrhodamine) may be characterized by their emission at wavelengths generally in the range of 590-690 nanometers. Examples of fluorophores include, but are not limited to, 4-acetamido-4'-isothiocyanatostilbene-2,2'disulfonic acid, acridine, derivatives of acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin, coumarin derivatives, 7-amino-4-methylcoumarin (AMC, Coumarin 120), 7-amino-trifluoromethylcoulaurin (Coumaran 151), cyanosine; 4',6-diaminidino-2-phenylindole (DAPI), 5',5''-dibromopyrogallol-sulfonephthalein (Bromopyrogallol Red), 7-diethylamino-3-(4'-isothiocyanatophenyl)-4-methylcoumarin, -, 4,4'-diisothiocyanatodihydro-stilbene-2,2'-disulfonic acid, 4,4'-diisothiocyanatostilbene-2,2'-disulfonic acid, 5-[dimethylamino]naphthalene-1-sulfonyl chloride (DNS, dansyl chloride), eosin, derivatives of eosin such as eosin isothiocyanate, erythrosine, derivatives of erythrosine such as erythrosine B and erythrosin isothiocyanate; ethidium; fluorescein and derivatives such as 5-carboxyfluorescein (FAM), 5-(4,6-dichlorotriazin-2-yl) aminofluorescein (DTAF), 2'7'-dimethoxy-4'5'-dichloro-6-carboxyfluorescein (JOE), fluorescein, fluorescein isothiocyanate (FITC), QFITC (XRITC); fluorescamine derivative (fluorescent upon reaction with amines); IR144; IR1446; Malachite Green isothiocyanate; 4-methylumbelliferone; ortho cresolphthalein; nitrotyrosine; pararosaniline; Phenol Red, B-phycoerythrin; o-phthaldialdehyde derivative (fluorescent upon reaction with amines); pyrene and derivatives such as pyrene, pyrene butyrate and succinimidyl 1-pyrene butyrate; Reactive Red 4 (Cibacron® Brilliant Red 3B-A), rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl Rhodamine, tetramethyl rhodamine isothiocyanate (TRITC); riboflavin; rosolic acid and lathanide chelate derivatives, quantum dots, cyanines, pyrelium dyes, and squaraines.

As used herein, the term "in situ" generally refers to an event occurring in the original location, for example, in intact organ or tissue or in a representative segment of an organ or tissue. In some embodiments, in situ analysis of targets may be performed on cells derived from a variety of sources, including an organism, an organ, tissue sample, or a cell culture. In situ analysis provides contextual information that may be lost when the target is removed from its site of origin. Accordingly, in situ analysis of targets describes analysis of target-bound probe located within a whole cell or a tissue sample, whether the cell membrane is fully intact or partially intact where target-bound probe remains within the cell. Furthermore, the methods disclosed herein may be employed to analyze targets in situ in cell or tissue samples that are fixed or unfixed.

As used herein, the term "peroxidase" refers to an enzyme class that catalyzes an oxidation reaction of an enzyme substrate along with an electron donor Examples of peroxidase enzymes include horseradish peroxidase, cytochrome C peroxidase, glutathione peroxidase, microperoxidase, myeloperoxidase, lactoperoxidase, or soybean peroxidase.

As used herein, the term "peroxidase substrate" refers to a chemical compound that is chemically catalyzed by peroxidase to form a reaction product. In some embodiments, peroxidase substrates employed in the methods herein may include non-chromogenic or non-chemiluminescent substrates. A fluorescent signal generator may be attached to the peroxidase substrate as a label.

As used herein, the term "probe" refers to an agent having a binder and a label, such as a signal generator or an enzyme. In some embodiments, the binder and the label (signal generator or the enzyme) are embodied in a single entity. The binder and the label may be attached directly (e.g., via a fluorescent molecule incorporated into the binder) or indirectly (e.g., through a linker, which may include a cleavage site) and applied to the biological sample in a single step. In alternative embodiments, the binder and the label are embodied in discrete entities (e.g., a primary antibody capable of binding a target and an enzyme or a signal generator-labeled secondary antibody capable of binding the primary antibody). When the binder and the label (signal generator or the enzyme) are separate entities they may be applied to a biological sample in a single step or multiple steps. As used herein, the term "fluorescent probe" refers to an agent having a binder coupled to a fluorescent signal generator.

As used herein, the term "signal generator" refers to a molecule capable of providing a detectable signal using one or more detection techniques (e.g., spectrometry, calorimetry, spectroscopy, or visual inspection). Suitable examples of a detectable signal may include an optical signal, and electrical signal, or a radioactive signal. Examples of signal generators include one or more of a chromophore, a fluorophore, a Raman-active tag, or a radioactive label. As stated above, with regard to the probe, the signal generator and the binder may be present in a single entity (e.g., a target binding protein with a fluorescent label) in some embodiments. Alternatively, the binder and the signal generator may be discrete entities (e.g., a receptor protein and a labeled-antibody against that particular receptor protein) that associate with each other before or upon introduction to the sample.

As used herein, the term "solid support" refers to an article on which targets present in the biological sample may be immobilized and subsequently detected by the methods disclosed herein. Targets may be immobilized on the solid support by physical adsorption, by covalent bond formation, or by combinations thereof. A solid support may include a polymeric, a glass, or a metallic material. Examples of solid supports include a membrane, a microtiter plate, a bead, a filter, a test strip, a slide, a cover slip, and a test tube.

As used herein, the term "specific binding" refers to the specific recognition of one of two different molecules for the other compared to substantially less recognition of other molecules. The molecules may have areas on their surfaces or in cavities giving rise to specific recognition between the two molecules arising from one or more of electrostatic interactions, hydrogen bonding, or hydrophobic interactions. Specific binding examples include, but are not limited to, antibody-antigen interactions, enzyme-substrate interactions, polynucleotide interactions, and the like. In some embodiments, a binder molecule may have an intrinsic equilibrium association constant (KA) for the target no lower than about $10^5$ $M^{-1}$ under ambient conditions such as a pH of about 6 to about 8 and temperature ranging from about 0° C. to about 37° C.

As used herein, the term "target," refers to the component of a biological sample that may be detected when present in the biological sample. The target may be any substance for which there exists a naturally occurring specific binder (e.g., an antibody), or for which a specific binder may be prepared (e.g., a small molecule binder or an aptamer). In general, a binder may bind to a target through one or more discrete chemical moieties of the target or a three-dimensional structural component of the target (e.g., 3D structures resulting from peptide folding). The target may include one or more of natural or modified peptides, proteins (e.g., antibodies, affibodies, or aptamers), nucleic acids (e.g., polynucleotides, DNA, RNA, or aptamers); polysaccharides (e.g., lectins or sugars), lipids, enzymes, enzyme substrates, ligands, receptors, antigens, or haptens. In some embodiments, targets may include proteins or nucleic acids.

The invention includes embodiments that relate generally to methods applicable in analytical, diagnostic, or prognostic applications such as analyte detection, histochemistry, immunohistochemistry, or immunofluorescence. In some embodiments, the methods disclosed herein may be particularly applicable in histochemistry, immunostaining, immunohistochemistry, immunoassays, or immunofluorescence. In some embodiments, the methods disclosed herein may be particularly applicable in immunoblotting techniques, for example, western blots or immunoassays such as enzyme-linked immunosorbent assays (ELISA).

The disclosed methods relate generally to detection of multiple targets in a single biological sample. In some embodiments, methods of detecting multiple targets in a single biological sample using the same detection channel are disclosed. The targets may be present on the surface of cells in suspension, on the surface of cytology smears, on the surface of histological sections, on the surface of DNA microarrays, on the surface of protein microarrays, or on the surface of solid supports (such as gels, blots, glass slides, beads, or ELISA plates).

The methods disclosed herein may allow detection of a plurality of targets in the same biological sample with little or no effect on the integrity of the biological sample. Detecting the targets in the same biological sample may further provide spatial information about the targets in the biological sample. Methods disclosed herein may also be applicable in analytical applications where a limited amount of biological sample may be available for analysis and the same sample may have to be processed for multiple analyses. Methods disclosed herein may also facilitate multiple analyses of solid-state samples (e.g., tissue sections) or samples adhered to a solid support (e.g., blots) without substantially stripping the probes and the targets. Furthermore, the same detection channel may be employed for detection of different targets in the sample, enabling fewer chemistry requirements for analyses of multiple targets. The methods may further facilitate analyses based on detection methods that may be limited in the number of simultaneously detectable targets because of limitations of resolvable signals. For example, using fluorescent-based detection, the number of targets that may be simultaneously detected may be limited to about four as only about four fluorescent signals may be resolvable based on their excitation and emission wavelength properties. In some embodiments, the methods disclosed herein may allow detection of greater than four targets using fluorescent-based detection system.

In some embodiments, the method of detecting multiple targets in a biological sample includes sequential detection of targets in the biological sample. The method generally includes the steps of detecting a first target in the biological sample, modifying the signal from the first target using a chemical agent, and detecting a second target in the biological sample. The method may further include repeating the step of modification of signal from the second target followed by detecting a third target in the biological sample, and so forth.

In some embodiments, the method includes the steps of contacting a biological sample with a first probe and physically binding a first probe to a first target. The method further includes observing a first signal from the first probe. A chemical agent is applied to the probe to modify the first signal. The method further includes contacting the biological sample with a second probe and physically binding the second probe to a second target in the biological sample followed by observing a second signal from the second probe.

In other embodiments, the method includes the steps of providing a sample containing multiple targets and binding at least one probe having a binder coupled to an enzyme to one or more target present in the sample. The method further includes reacting the bound probe with an enzyme substrate coupled to a fluorescent signal generator and observing a signal from the fluorescent signal generator. A solution including an oxidizing agent that substantially inactivates both the fluorescent signal generator and the enzyme is applied to the sample. The method further includes binding at least one subsequent probe having a binder coupled to an enzyme to one or more target present in the sample. The method further includes reacting the bound probe with an enzyme substrate coupled to a fluorescent signal generator and observing a signal from the fluorescent signal generator.

In yet other embodiments, the method includes the steps of providing a biological sample containing multiple targets adhered to a solid support and binding at least one fluorescent probe to one or more target present in the sample. The method further includes observing a signal from the bound fluorescent probe. The bound fluorescent probe is oxidized with an oxidizing agent that substantially inactivates the fluorescent probe. The method further includes binding at least one subsequent fluorescent probe to one or more target present in the sample followed by observing a signal from the subsequent bound fluorescent probe.

In yet other embodiments, the method includes the steps of providing a biological sample containing multiple targets adhered to a solid support and binding at least one fluorescent probe to one or more target present in the sample. The method further includes binding at least one control probe to one or more target in the sample. The method further includes observing a signal from the bound fluorescent probe and a control signal from the control probe. The bound fluorescent probe is oxidized with an oxidizing agent that substantially inactivates the fluorescent probe and not the control probe. The method further includes binding at least one subsequent fluorescent probe to one or more target present in the sample followed by observing a signal from the subsequent bound fluorescent probe.

Biological Samples

A biological sample in accordance with one embodiment of the invention may be solid or fluid. Suitable examples of biological samples may include, but are not limited to, but are not limited to, cultures, blood, plasma, serum, saliva, cerebral spinal fluid, pleural fluid, milk, lymph, sputum, semen, urine, stool, tears, saliva, needle aspirates, external sections of the skin, respiratory, intestinal, and genitourinary tracts, tumors, organs, cell cultures or cell culture constituents, or solid tissue sections. In some embodiments, the biological sample may be analyzed as is, that is, without harvest and/or isolation of the target of interest. In an alternate embodiment, harvest and isolation of targets may be performed prior to analysis. In some embodiments, the methods disclosed herein may be particularly suitable for in-vitro analysis of biological samples.

A biological sample may include any of the aforementioned samples regardless of their physical condition, such as, but not limited to, being frozen or stained or otherwise treated. In some embodiments, a biological sample may include compounds which are not naturally intermixed with the sample in nature such as preservatives, anticoagulants, buffers, fixatives, nutrients, antibiotics, or the like.

In some embodiments, a biological sample may include a tissue sample, a whole cell, a cell constituent, a cytospin, or a cell smear. In some embodiments, a biological sample essentially includes a tissue sample. A tissue sample may include a collection of similar cells obtained from a tissue of a biological subject that may have a similar function. In some embodiments, a tissue sample may include a collection of similar cells obtained from a tissue of a human. Suitable examples of human tissues include, but are not limited to, (1) epithelium; (2) the connective tissues, including blood vessels, bone and cartilage; (3) muscle tissue; and (4) nerve tissue. The source of the tissue sample may be solid tissue obtained from a fresh, frozen and/or preserved organ or tissue sample or biopsy or aspirate; blood or any blood constituents; bodily fluids such as cerebral spinal fluid, amniotic fluid, peritoneal fluid, or interstitial fluid; or cells from any time in gestation or development of the subject. In some embodiments, the tissue sample may include primary or cultured cells or cell lines.

In some embodiments, a biological sample includes tissue sections from healthy or diseases tissue samples (e.g., tissue section from colon, breast tissue, prostate). A tissue section may include a single part or piece of a tissue sample, for example, a thin slice of tissue or cells cut from a tissue sample. In some embodiments, multiple sections of tissue samples may be taken and subjected to analysis, provided the methods disclosed herein may be used for analysis of the same section of the tissue sample with respect to at least two different targets (at morphological or molecular level). In some embodiments, the same section of tissue sample may be analyzed with respect to at least four different targets (at morphological or molecular level). In some embodiments, the same section of tissue sample may be analyzed with respect to greater than four different targets (at morphological or molecular level). In some embodiments, the same section of tissue sample may be analyzed at both morphological and molecular levels.

A tissue section, if employed as a biological sample may have a thickness in a range that is less than about 100 micrometers, in a range that is less than about 50 micrometers, in a range that is less than about 25 micrometers, or in range that is less than about 10 micrometers.

In some embodiments, a biological sample or the targets in the biological sample may be adhered to a solid support. A solid support may include microarrays (e.g., DNA or RNA microarrays), gels, blots, glass slides, beads, or ELISA plates. In some embodiments, a biological sample or the targets in the biological sample may be adhered to a membrane selected from nylon, nitrocellulose, and polyvinylidene difluoride. In some embodiments, the solid support may include a plastic surface selected from polystyrene, polycarbonate, and polypropylene.

Targets

A target may be present on the surface of a biological sample (for example, an antigen on a surface of a tissue section) or present in the bulk of the sample (for example, an antibody in a buffer solution). In some embodiments, a target may not be inherently present on the surface of a biological sample and the biological sample may have to be processed to make the target available on the surface (e.g., antigen recovery, enzymatic digestion, epitope retrieval, or blocking). In some embodiments, the target may be present in a body fluid such as blood, blood plasma, serum, or urine. In some other embodiments, the target may be fixed in a tissue, either on a cell surface, or within a cell.

Suitability of targets to be analyzed may be determined by the type and nature of analysis required for the biological sample. In some embodiments, a target may provide information about the presence or absence of an analyte in the biological sample. In another embodiment, a target may provide information on a state of a biological sample. For example, if the biological sample includes a tissue sample, the methods disclosed herein may be used to detect targets that may help in comparing different types of cells or tissues, comparing different developmental stages, detecting the presence of a disease or abnormality, or determining the type of disease or abnormality.

Targets may include one or more of peptides, proteins (e.g., antibodies, affibodies, or aptamers), nucleic acids (e.g., polynucleotides, DNA, RNA, or aptamers); polysaccharides (e.g., lectins or sugars), lipids, enzymes, enzyme substrates, ligands, receptors, antigens, or haptens. In some embodiments, targets may essentially include proteins or nucleic acids. One or more of the aforementioned targets may be characteristic of particular cells, while other targets may be associated with a particular disease or condition. In some embodiments, targets that may be detected and analyzed using the methods disclosed herein may include, but are not limited to, prognostic targets, hormone or hormone receptor targets, lymphoid targets, tumor targets, cell cycle associated targets, neural tissue and tumor targets, or cluster differentiation targets Suitable examples of prognostic targets may include enzymatic targets such as galactosyl transferase II, neuron specific enolase, proton ATPase-2, or acid phosphatase.

Suitable examples of hormone or hormone receptor targets may include human chorionic gonadotropin (HCG), adrenocorticotropic hormone, carcinoembryonic antigen (CEA), prostate-specific antigen (PSA), estrogen receptor, progesterone receptor, androgen receptor, gC1q-R/p33 complement receptor, IL-2 receptor, p75 neurotrophin receptor, PTH receptor, thyroid hormone receptor, or insulin receptor.

Suitable examples of lymphoid targets may include alpha-1-antichymotrypsin, alpha-1-antitrypsin, B cell target, bcl-2, bcl-6, B lymphocyte antigen 36 kD, BM1 (myeloid target), BM2 (myeloid target), galectin-3, granzyme B, HLA class I Antigen, HLA class II (DP) antigen, HLA class II (DQ) antigen, HLA class II (DR) antigen, human neutrophil defensins, immunoglobulin A, immunoglobulin D, immunoglobulin G, immunoglobulin M, kappa light chain, kappa light chain, lambda light chain, lymphocyte/histocyte antigen, macrophage target, muramidase (lysozyme), p80 anaplastic lymphoma kinase, plasma cell target, secretory leukocyte protease inhibitor, T cell antigen receptor (JOVI 1), T cell antigen receptor (JOVI 3), terminal deoxynucleotidyl transferase, or unclustered B cell target.

Suitable examples of tumour targets may include alpha fetoprotein, apolipoprotein D, BAG-1 (RAP46 protein), CA19-9 (sialyl lewisa), CA50 (carcinoma associated mucin antigen), CA125 (ovarian cancer antigen), CA242 (tumour associated mucin antigen), chromogranin A, clusterin (apolipoprotein J), epithelial membrane antigen, epithelial-related antigen, epithelial specific antigen, gross cystic disease fluid protein-15, hepatocyte specific antigen, heregulin, human gastric mucin, human milk fat globule, MAGE-1, matrix metalloproteinases, melan A, melanoma target (HMB45), mesothelin, metallothionein, microphthalmia transcription factor (MITF), Muc-1 core glycoprotein. Muc-1 glycoprotein, Muc-2 glycoprotein, Muc-5AC glycoprotein, Muc-6 glycoprotein, myeloperoxidase, Myf-3 (Rhabdomyosarcoma target), Myf-4 (Rhabdomyosarcoma target), MyoD1 (Rhabdomyosarcoma target), myoglobin, nm23 protein, placental alkaline phosphatase, prealbumin, prostate specific antigen, prostatic acid phosphatase, prostatic inhibin peptide, PTEN, renal cell carcinoma target, small intestinal mucinous antigen, tetranectin, thyroid transcription factor-1, tissue inhibitor of matrix metalloproteinase 1, tissue inhibitor of matrix metalloproteinase 2, tyrosinase, tyrosinase-related protein-1, villin, or von Willebrand factor.

Suitable examples of cell cycle associated targets may include apoptosis protease activating factor-1, bcl-w, bcl-x, bromodeoxyuridine, CAK (cdk-activating kinase), cellular apoptosis susceptibility protein (CAS), caspase 2, caspase 8, CPP32 (caspase-3), CPP32 (caspase-3), cyclin dependent kinases, cyclin A, cyclin B1, cyclin D1, cyclin D2, cyclin D3, cyclin E, cyclin G, DNA fragmentation factor (N-terminus), Fas (CD95), Fas-associated death domain protein, Fas ligand, Fen-1, IPO-38, Mcl-1, minichromosome maintenance proteins, mismatch repair protein (MSH2), poly (ADP-Ribose) polymerase, proliferating cell nuclear antigen, p16 protein, p27 protein, p34cdc2, p57 protein (Kip2), p105 protein, Stat 1 alpha, topoisomerase I, topoisomerase II alpha, topoisomerase III alpha, or topoisomerase II beta.

Suitable examples of neural tissue and tumor targets may include alpha B crystallin, alpha-internexin, alpha synuclein, amyloid precursor protein, beta amyloid, calbindin, choline acetyltransferase, excitatory amino acid transporter 1, GAP43, glial fibrillary acidic protein, glutamate receptor 2, myelin basic protein, nerve growth factor receptor (gp75), neuroblastoma target, neurofilament 68 kD, neurofilament 160 kD, neurofilament 200 kD, neuron specific enolase, nicotinic acetylcholine receptor alpha4, nicotinic acetylcholine receptor beta2, peripherin, protein gene product 9, S-100 protein, serotonin, SNAP-25, synapsin I, synaptophysin, tau, tryptophan hydroxylase, tyrosine hydroxylase, or ubiquitin.

Suitable examples of cluster differentiation targets may include CD1a, CD1b, CD1c, CD1d, CD1e, CD2, CD3delta, CD3epsilon, CD3gamma, CD4, CD5, CD6, CD7, CD8alpha, CD8beta, CD9, CD10, CD11a, CD11b, CD11c, CDw12, CD13, CD14, CD15, CD15s, CD16a, CD16b, CDw17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42a, CD42b, CD42c, CD42d, CD43, CD44, CD44R, CD45, CD46, CD47, CD48, CD49a, CD49b, CD49c, CD49d, CD49e, CD49f, CD50, CD51, CD52, CD53, CD54, CD55, CD56, CD57, CD58, CD59, CDw60, CD61, CD62E, CD62L, CD62P, CD63, CD64, CD65, CD65s, CD66a, CD66b, CD66c, CD66d, CD66e, CD66f, CD68, CD69, CD70, CD71, CD72, CD73, CD74, CDw75, CDw76, CD77, CD79a, CD79b, CD80, CD81, CD82, CD83, CD84, CD85, CD86, CD87, CD88, CD89, CD90, CD91, CDw92, CDw93, CD94, CD95, CD96, CD97, CD98, CD99, CD100, CD101, CD102, CD103, CD104, CD105, CD106, CD107a, CD107b, CDw108, CD109, CD114, CD115, CD116, CD117, CDw119, CD120a, CD120b, CD121a, CDw121b, CD122, CD123, CD124, CDw125, CD126, CD127, CDw128a, CDw128b, CD130, CDw131, CD132, CD134, CD135, CDw136, CDw137, CD138, CD139, CD140a, CD140b, CD141, CD142, CD143, CD144, CDw145, CD146, CD147, CD148, CDw149, CDw150, CD151, CD152, CD153, CD154, CD155, CD156, CD157, CD158a, CD158b, CD161, CD162, CD163, CD164, CD165, CD166, and TCR-zeta.

Other suitable prognostic targets may include centromere protein-F (CENP-F), giantin, involucrin, lamin A&C (XB 10), LAP-70, mucin, nuclear pore complex proteins, p180 lamellar body protein, ran, r, cathepsin D, Ps2 protein, Her2-neu, P53, S100, epithelial target antigen (EMA), TdT, MB2, MB3, PCNA, or Ki67.

Probes

In some embodiments, a binder and a label (signal generator or an enzyme) may be coupled to each other directly (that is without any linkers). In other embodiments, a binder and a label (signal generator or an enzyme) may be coupled to each other via a linker. As used herein, "coupled" generally refers to two entities (for example, binder and signal generator) stably bound to one another by any physicochemical means. The nature of the coupling may be such that it does not substantially impair the effectiveness of either entity. A binder and a label may be coupled to each other through covalent or non-covalent interactions. Non-covalent interactions may include, but are not limited to, hydrophobic interactions, ionic interactions, hydrogen-bond interactions, high affinity interactions (such as, biotin-avidin or biotin-streptavidin complexation), or other affinity interactions.

A linker may include a form of linking structure or sequence formed due to the non-covalent or covalent bond formation. In some embodiments, the linker may be chemically stable, that is, may maintain its integrity in the presence of a chemical agent. In some embodiments, the linker may be susceptible to chemical agents that is may be capable of dissociating, cleaving, or hydrolyzing in the presence of a chemical agent. Suitable examples of linkers may include disulfide bonds (e.g., SPDP or SMPT), pH sensitive structures/sequences, structures/sequences that may be reduced in the presence of an reducing agent, structures/sequences that may be oxidized in the presence of an oxidizing agent, or any other chemical or physical bond that may be easily manipulated (dissociated, cleaved, or hydrolyzed) in the presence of a chemical agent.

In some embodiments, a binder and a label (signal generator or an enzyme) may be chemically linked to each other through functional groups capable of reacting and forming a linkage under suitable conditions. Suitable examples of functional group combinations may include, but are not limited to, amine ester and amines or anilines; acyl azide and amines or anilines; acyl halides and amines, anilines, alcohols, or phenols; acyl nitrile and alcohols or phenols; aldehyde and amines or anilines; alkyl halide and amines, anilines, alcohols, phenols or thiols; alkyl sulfonate and thiols, alcohols or phenols; anhydride and alcohols, phenols, amines or anilines; aryl halide and thiols; aziridine and thiols or thioethers; carboxylic acid and amines, anilines, alcohols or alkyl halides; diazoalkane and carboxylic acids; epoxide and thiols; haloacetamide and thiols; halotriazin and amines, anilines or phenols; hydrazine and aldehydes or ketones; hydroxyamine and aldehydes or ketones; imido ester and amines or anilines;

isocyanate and amines or anilines; and isothiocyanate and amines or anilines. A functional group in one of the aforementioned functional group pair may be present in a binder and a corresponding functional group may be present in the signal generator or the enzyme. For example, a binder may include a carboxylic acid and the signal generator or the enzyme may include an amine, aniline, alcohol or acyl halide, or vice versa. Conjugation between the binder and the signal generator or the enzyme may be effected in this case by formation of an amide or an ester linkage.

In some embodiments, the binder may be intrinsically labeled with a signal generator (for example, if the binder is a protein, during synthesis using a detectably labeled amino acid) or an enzyme (for example, if the binder is an enzyme). A binder that is intrinsically labeled may not require a separate signal generator or an enzyme in order to be detected. Rather the intrinsic label may be sufficient for rendering the probe detectable. In alternate embodiments, the binder may be labeled by binding to it a specific signal generator or an enzyme (i.e., extrinsically labeled).

In some embodiments, the binder and the label (signal generator or the enzyme) are embodied in a single entity. In alternative embodiments, the binder and the label (signal generator or the enzyme) are embodied in discrete entities (e.g., a primary antibody capable of binding a target and an enzyme or a signal generator-labeled secondary antibody capable of binding the primary antibody or a hapten labeled primary antibody capable of binding a target and an enzyme or a signal generator-labeled anti-hapten antibody capable of binding the hapten labeled primary antibody). When the binder and the signal generator or the enzyme are separate entities they may be applied to a biological sample in a single step or multiple steps. In some embodiments, the binder and the label (signal generator or the enzyme) are separate entities that are pre-attached before application to the biological sample and applied to the biological sample in a single step. In yet other embodiments, the binder and the label (signal generator or the enzyme) are separate entities that are applied to the biological sample independently and combine following application.

Binders

The methods disclosed herein involve the use of binders that physically bind to the target in a specific manner. In some embodiments, a binder may bind to a target with sufficient specificity, that is, a binder may bind to a target with greater affinity than it does to any other molecule. In some embodiments, the binder may bind to other molecules, but the binding may be such that the non-specific binding may be at or near background levels. In some embodiments, the affinity of the binder for the target of interest may be in a range that is at least 2-fold, at least 5-fold, at least 10-fold, or more than its affinity for other molecules. In some embodiments, binders with the greatest differential affinity may be employed, although they may not be those with the greatest affinity for the target.

In some embodiments, binding between the target and the binder may be affected by physical binding. Physical binding may include binding effected using non-covalent interactions. Non-covalent interactions may include, but are not limited to, hydrophobic interactions, ionic interactions, hydrogen-bond interactions, or affinity interactions (such as, biotin-avidin or biotin-streptavidin complexation). In some embodiments, the target and the binder may have areas on their surfaces or in cavities giving rise to specific recognition between the two resulting in physical binding. In some embodiments, a binder may bind to a biological target based on the reciprocal fit of a portion of their molecular shapes.

Binders and their corresponding targets may be considered as binding pairs, of which non-limiting examples include immune-type binding-pairs, such as, antigen/antibody, antigen/antibody fragment, or hapten/anti-hapten; nonimmune-type binding-pairs, such as biotin/avidin, biotin/streptavidin, folic acid/folate binding protein, hormone/hormone receptor, lectin/specific carbohydrate, enzyme/enzyme, enzyme/substrate, enzyme/substrate analog, enzyme/pseudo-substrate (substrate analogs that cannot be catalyzed by the enzymatic activity), enzyme/co-factor, enzyme/modulator, enzyme/inhibitor, or vitamin B12/intrinsic factor. Other suitable examples of binding pairs may include complementary nucleic acid fragments (including DNA sequences, RNA sequences, LNA sequences, and PNA sequences); Protein A/antibody; Protein G/antibody; nucleic acid/nucleic acid binding protein; or polynucleotide/polynucleotide binding protein.

In some embodiments, the binder may be a sequence- or structure-specific binder, wherein the sequence or structure of a target recognized and bound by the binder may be sufficiently unique to that target.

In some embodiments, the binder may be structure-specific and may recognize a primary, secondary, or tertiary structure of a target. A primary structure of a target may include specification of its atomic composition and the chemical bonds connecting those atoms (including stereochemistry), for example, the type and nature of linear arrangement of amino acids in a protein. A secondary structure of a target may refer to the general three-dimensional form of segments of biomolecules, for example, for a protein a secondary structure may refer to the folding of the peptide "backbone" chain into various conformations that may result in distant amino acids being brought into proximity with each other. Suitable examples of secondary structures may include, but are not limited to, alpha helices, beta pleated sheets, or random coils. A tertiary structure of a target may be is its overall three dimensional structure. A quaternary structure of a target may be the structure formed by its noncovalent interaction with one or more other targets or macromolecules (such as protein interactions). An example of a quaternary structure may be the structure formed by the four-globin protein subunits to make hemoglobin. A binder in accordance with the embodiments of the invention may be specific for any of the aforementioned structures.

An example of a structure-specific binder may include a protein-specific molecule that may bind to a protein target. Examples of suitable protein-specific molecules may include antibodies and antibody fragments, nucleic acids (for example, aptamers that recognize protein targets), or protein substrates (non-catalyzable).

In some embodiments, a target may include an antigen and a binder may include an antibody. A suitable antibody may include monoclonal antibodies, polyclonal antibodies, multispecific antibodies (for example, bispecific antibodies), or antibody fragments so long as they bind specifically to a target antigen.

In some embodiments, a biological sample may include a cell or a tissue sample and the methods disclosed herein may be employed in immunohistochemistry (IHC). Immunochemistry may involve binding of a target antigen to an antibody-based binder to provide information about the tissues or cells (for example, diseased versus normal cells). Examples of antibodies (and the corresponding diseases/disease cells) suitable as binders for methods disclosed herein include, but are not limited to, anti-estrogen receptor antibody (breast cancer), anti-progesterone receptor antibody (breast cancer), anti-p53 antibody (multiple cancers), anti-Her-2/neu antibody (multiple cancers), anti-EGFR antibody (epidermal growth factor, multiple cancers), anti-cathepsin D antibody (breast and other cancers), anti-Bcl-2 antibody (apoptotic cells), anti-E-cadherin antibody, anti-CA125 antibody (ovarian and other cancers), anti-CA15-3 antibody (breast cancer), anti-CA19-9 antibody (colon cancer), anti-c-erbB-2 antibody, anti-P-glycoprotein antibody (MDR, multidrug resistance), anti-CEA antibody (carcinoembryonic antigen), anti-retinoblastoma protein (Rb) antibody, anti-ras oneoprotein (p21) antibody, anti-Lewis X (also called CD15) antibody, anti-Ki-67 antibody (cellular proliferation), anti-PCNA (multiple cancers) antibody, anti-CD 3 antibody (T-cells), anti-CD4 antibody (helper T cells), anti-CD5 antibody (T cells), anti-CD7 antibody (thymocytes, immature T cells, NK killer cells), anti-CD8 antibody (suppressor T cells), anti-CD9/p24 antibody (ALL), anti-CD10 (also called CALLA) antibody (common acute lymphoblastic leukemia), anti-CD11c antibody (Monocytes, granulocytes, AML), anti-CD13 antibody (myelomonocytic cells, AML), anti-CD14 antibody (mature monocytes, granulocytes), anti-CD15 antibody (Hodgkin's disease), anti-CD19 antibody (B cells), anti-CD20 antibody (B cells), anti-CD22 antibody (B cells), anti-CD23 antibody (activated B cells, CLL), anti-CD30 antibody (activated T and B cells, Hodgkin's disease), anti-CD31 antibody (angiogenesis marker), anti-CD33 antibody (myeloid cells, AML), anti-CD34 antibody (endothelial stem cells, stromal tumors), anti-CD35 antibody (dendritic cells), anti-CD38 antibody (plasma cells, activated T, B, and myeloid cells), anti-CD 41 antibody (platelets, megakaryocytes), anti-LCA/CD45 antibody (leukocyte common antigen), anti-CD45RO antibody (helper, inducer T cells), anti-CD45RA antibody (B cells), anti-CD39, CD100 antibody, anti-CD95/Fas antibody (apoptosis), anti-CD99 antibody (Ewings Sarcoma marker, MIC2 gene product), anti-CD106 antibody (VCAM-1; activated endothelial cells), anti-ubiquitin antibody (Alzheimer's disease), anti-CD71 (transferrin receptor) antibody, anti-c-myc (oncoprotein and a hapten) antibody, anti-cytokeratins (transferrin receptor) antibody, anti-vimentins (endothelial cells) antibody (B and T cells), anti-HPV proteins (human papillomavirus) antibody, anti-kappa light chains antibody (B cell), anti-lambda light chains antibody (B cell), anti-melanosomes (HMB45) antibody (melanoma), anti-prostate specific antigen (PSA) antibody (prostate cancer), anti-S-100 antibody (melanoma, salivary, glial cells), anti-tau antigen antibody (Alzheimer's disease), anti-fibrin antibody (epithelial cells), anti-keratins antibody, anti-cytokeratin antibody (tumor), anti-alpha-catenin (cell membrane), or anti-Tn-antigen antibody (colon carcinoma, adenocarcinomas, and pancreatic cancer).

Other specific examples of suitable antibodies may include, but are not limited to, anti proliferating cell nuclear antigen, clone pc10 (Sigma Aldrich, P8825); anti smooth muscle alpha actin (SmA), clone 1A4 (Sigma, A2547); rabbit anti beta catenin (Sigma, C 2206); mouse anti pan cytokeratin, clone PCK-26 (Sigma, C1801); mouse anti estrogen receptor alpha, clone 1D5 (DAKO, M 7047); beta catenin antibody, clone 15B8 (Sigma, C 7738); goat anti vimentin (Sigma, V4630); cycle androgen receptor clone AR441 (DAKO, M3562); Von Willebrand Factor 7, keratin 5, keratin 8/18, e-cadherin, Her2/neu, Estrogen receptor, p53, progesterone receptor, beta catenin; donkey anti-mouse (Jackson Immunoresearch, 715-166-150); or donkey anti rabbit (Jackson Immunoresearch, 711-166-152).

In some embodiments, a binder may be sequence-specific. A sequence-specific binder may include a nucleic acid and the binder may be capable of recognizing a particular linear arrangement of nucleotides or derivatives thereof in the target. In some embodiments, the linear arrangement may include contiguous nucleotides or derivatives thereof that may each bind to a corresponding complementary nucleotide in the binder. In an alternate embodiment, the sequence may not be contiguous as there may be one, two, or more nucleotides that may not have corresponding complementary residues on the probe. Suitable examples of nucleic acid-based binders may include, but are not limited to, DNA or RNA oligonucleotides or polynucleotides. In some embodiments, suitable nucleic acids may include nucleic acid analogs, such as dioxygenin dCTP, biotin dcTP 7-azaguanosine, azidothymidine, inosine, or uridine.

In certain embodiments, both the binder and the target may include nucleic acids. In some embodiments, a nucleic-acid based binder may form a Watson-Crick bond with the nucleic acid target. In another embodiment, the nucleic acid binder may form a Hoogsteen bond with the nucleic acid target, thereby forming a triplex. A nucleic acid binder that binds by Hoogsteen binding may enter the major groove of a nucleic acid target and hybridizes with the bases located there. Suitable examples of the above binders may include molecules that recognize and bind to the minor and major grooves of nucleic acids (for example, some forms of antibiotics.) In certain embodiments, the nucleic acid binders may form both Watson-Crick and Hoogsteen bonds with the nucleic acid target (for example, bis PNA probes are capable of both Watson-Crick and Hoogsteen binding to a nucleic acid).

The length of nucleic acid binder may also determine the specificity of binding. The energetic cost of a single mismatch between the binder and the nucleic acid target may be relatively higher for shorter sequences than for longer ones. In some embodiments, hybridization of smaller nucleic acid binders may be more specific than the hybridization of longer nucleic acid probes, as the longer probes may be more amenable to mismatches and may continue to bind to the nucleic acid depending on the conditions. In certain embodiments, shorter binders may exhibit lower binding stability at a given temperature and salt concentration. Binders that may exhibit greater stability to bind short sequences may be employed in this case (for examples, bis PNA). In some embodiments, the nucleic acid binder may have a length in range of from about 4 nucleotides to about 12 nucleotides, from about 12 nucleotides to about 25 nucleotides, from about 25 nucleotides to about 50 nucleotides, from about 50 nucleotides to about 100 nucleotides, from about 100 nucleotides to about 250 nucleotides, from about 250 nucleotides to about 500 nucleotides, or from about 500 nucleotides to about 1000 nucleotides. In some embodiments, the nucleic acid binder may have a length in a range that is greater than about 1000 nucleotides. Notwithstanding the length of the nucleic acid binder, all the nucleotide residues of the binder may not hybridize to complementary nucleotides in the nucleic acid target. For example, the binder may include 50 nucleotide residues in length, and only 25 of those nucleotide residues may hybridize to the nucleic acid target. In some embodiments, the nucleotide residues that may hybridize may be contiguous with each other. The nucleic acid binders may be single stranded or may include a secondary structure. In some embodiments, a biological sample may include a cell or a tissue sample and the biological sample may be subjected to in-situ hybridization (ISH) using a nucleic acid binder. In some embodiments, a tissue sample may be subjected to in situ hybridization in addition to immunohistochemistry (IHC) to obtain desired information from the sample.

Regardless of the type of binder and the target, the specificity of binding between the binder and the target may also be affected depending on the binding conditions (for example, hybridization conditions in case of complementary nucleic acids). Suitable binding conditions may be realized by modulation one or more of pH, temperature, or salt concentration.

A binder may be intrinsically labeled (signal generator or enzyme attached during synthesis of binder) or extrinsically labeled (signal generator or enzyme attached during a later step). For example for a protein-based binder, an intrinsically labeled binder may be prepared by employing labeled amino acids. Similarly, an intrinsically labeled nucleic acid may be synthesized using methods that incorporate signal generator-labeled nucleotides directly into the growing nucleic acid. In some embodiments, a binder may be synthesized in a manner such that signal generators or enzymes may be incorporated at a later stage. For example, this latter labeling may be accomplished by chemical means by the introduction of active amino or thiol groups into nucleic acids of peptide chains. In some embodiments, a binder such a protein (for example, an antibody) or a nucleic acid (for example, a DNA) may be directly chemically labeled using appropriate chemistries.

In some embodiments, combinations of binders may be used that may provide greater specificity or in certain embodiments amplification of the signal. Thus, in some embodiments, a sandwich of binders may be used, where the first binder may bind to the target and serve to provide for secondary binding, where the secondary binder may or may not include a label, which may further provide for tertiary binding (if required) where the tertiary binding member may include a label.

Suitable examples of binder combinations may include primary antibody-secondary antibody, complementary nucleic acids, or other ligand-receptor pairs (such as biotin-streptavidin). Some specific examples of suitable binder pairs may include mouse anti-myc for recombinant expressed proteins with c-myc epitope; mouse anti-HisG for recombinant protein with His-Tag epitope, mouse anti-express for recombinant protein with epitope-tag, rabbit anti-goat for goat IgG primary molecules, complementary nucleic acid sequence for a nucleic acid; mouse anti-thio for thioredoxin fusion proteins, rabbit anti-GFP for fusion protein, jacalin for α-D-galactose; and melibiose for carbohydrate-binding proteins, sugars, nickel couple matrix or heparin.

In some embodiments, a combination of a primary antibody and a secondary antibody may be used as a binder. A primary antibody may be capable of binding to a specific region of the target and the secondary antibody may be capable of binding to the primary antibody. A secondary antibody may be attached to a signal generator or an enzyme before binding to the primary antibody or may be capable of binding to a signal generator or an enzyme at a later step. In an alternate embodiment, a primary antibody and specific binding ligand-receptor pairs (such as biotin-streptavidin) may be used. The primary antibody may be attached to one member of the pair (for example biotin) and the other member (for example streptavidin) may be labeled with a signal generator or an enzyme. The secondary antibody, avidin, streptavidin, or biotin may be each independently labeled with a signal generator or an enzyme.

In some embodiments, the methods disclosed herein may be employed in an immunostaining procedure, and a primary antibody may be used to specifically bind the target protein. A secondary antibody may be used to specifically bind to the primary antibody, thereby forming a bridge between the primary antibody and a subsequent reagent (for example a signal generator or enzyme), if any. For example, a primary antibody may be mouse IgG (an antibody created in mouse) and the corresponding secondary antibody may be goat anti-mouse (antibody created in goat) having regions capable of binding to a region in mouse IgG.

In some embodiments, signal amplification may be obtained when several secondary antibodies may bind to epitopes on the primary antibody. In an immunostaining procedure a primary antibody may be the first antibody used in the procedure and the secondary antibody may be the second antibody used in the procedure. In some embodiments, a primary antibody may be the only antibody used in an immunostaining procedure.

Signal Generators

The type of signal generator suitable for the methods disclosed herein may depend on a variety of factors, including the nature of the analysis being conducted, the type of the energy source and detector used, the type of oxidizing agent employed, the type of binder, the type of target, or the mode of attachment between the binder and the signal generator (e.g., cleavable or non-cleavable).

A suitable signal generator may include a molecule or a compound capable of providing a detectable signal. A signal generator may provide a characteristic signal following interaction with an energy source or a current. An energy source may include electromagnetic radiation source and a fluorescence excitation source. Electromagnetic radiation source may be capable of providing electromagnetic energy of any wavelength including visible, infrared and ultraviolet. Electromagnetic radiation may be in the form of a direct light source or may be emitted by a light emissive compound such as a donor fluorophore. A fluorescence excitation source may be capable of making a source fluoresce or may give rise to photonic emissions (that is, electromagnetic radiation, directed electric field, temperature, physical contact, or mechanical disruption). Suitable signal generators may provide a signal capable of being detected by a variety of methods including optical measurements (for example, fluorescence), electrical conductivity, or radioactivity. Suitable signal generators may be, for example, light emitting, energy accepting, fluorescing, radioactive, or quenching.

A suitable signal generator may be sterically and chemically compatible with the constituents to which it is bound, for example, a binder. Additionally, a suitable signal generator may not interfere with the binding of the binder to the target, nor may it affect the binding specificity of the binder. A suitable signal generator may be organic or inorganic in nature. In some embodiments, a signal generator may be of a chemical, peptide or nucleic acid nature.

A suitable signal generator may be directly detectable. A directly detectable moiety may be one that may be detected directly by its ability to emit a signal, such as for example a fluorescent label that emits light of a particular wavelength following excitation by light of another lower, characteristic wavelength and/or absorb light of a particular wavelength.

A signal generator, suitable in accordance with the methods disclosed herein may be amenable to manipulation on application of a chemical agent. In some embodiments, a signal generator may be capable of being chemically destroyed on exposure to an oxidizing agent. Chemical destruction may include complete disintegration of the signal generator or modification of the signal-generating component of the signal generator. Modification of the signal-generating component may include any chemical modification (such as addition, substitution, or removal) that may result in the modification of the signal generating properties. For example, unconjugating a conjugated signal generator may result in destruction of chromogenic properties of the signal generator. Similarly, substitution of a fluorescence-inhibiting functional group on a fluorescent signal generator may result in modification of its fluorescent properties. In some embodiments, one or more signal generators substantially resistant to inactivation by a specific chemical agent may be used as a control probe in the provided methods.

In some embodiments, a signal generator may be selected from a light emissive molecule, a radioisotope (e.g., $P^{32}$ or $H^3$, $^{14}C$, $^{125}I$ and $^{131}I$), an optical or electron density marker, a Raman-active tag, an electron spin resonance molecule (such as for example nitroxyl radicals), an electrical charge transferring molecule (i.e., an electrical charge transducing molecule), a semiconductor nanocrystal, a semiconductor nanoparticle, a colloid gold nanocrystal, a microbead, a magnetic bead, a paramagnetic particle, or a quantum dot.

In some embodiments, a signal generator may include a light-emissive molecule. A light emissive molecule may emit light in response to irradiation with light of a particular wavelength. Light emissive molecules may be capable of absorbing and emitting light through luminescence (non-thermal emission of electromagnetic radiation by a material upon excitation), phosphorescence (delayed luminescence as a result of the absorption of radiation), chemiluminescence (luminescence due to a chemical reaction), fluorescence, or polarized fluorescence.

In some embodiments, a signal generator may essentially include a fluorophore. In some embodiments, a signal generator may essentially include a fluorophore attached to an antibody, for example, in an immunohistochemistry analysis. Suitable fluorophores that may be conjugated to a primary antibody include, but are not limited to, Fluorescein, Rhodamine, Texas Red, VECTOR Red, ELF (Enzyme-Labeled Fluorescence), Cy2, Cy3, Cy3.5, Cy5, Cy7, Fluor X, Calcein, Calcein-AM, CRYPTOFLUOR, Orange (42 kDa), Tangerine (35 kDa), Gold (31 kDa), Red (42 kDa), Crimson (40 kDa), BHMP, BHDMAP, Br-Oregon, Lucifer Yellow, Alexa dye family, N-[6-(7-nitrobenz-2-oxa-1,3-diazol-4-yl) amino]caproyl] (NBD), BODIPY, boron dipyrromethene difluoride, Oregon Green, MITOTRACKER Red, Phycoerythrin, Phycobiliproteins BPE (240 kDa) RPE (240 kDa) CPC (264 kDa) APC (104 kDa), Spectrum Blue, Spectrum Aqua, Spectrum Green, Spectrum Gold, Spectrum Orange, Spectrum Red, Infra-Red (IR) Dyes, Cyclic GDP-Ribose (cGDPR), Calcfluor White, Lissamine, Umbelliferone, Tyrosine or Tryptophan. In some embodiments, a signal generator may essentially include a cyanine dye. In some embodiments, a signal generator may essentially include one or more a Cy3 dye, a Cy5 dye, or a Cy7 dye.

In some embodiments, the signal generator may be part of a FRET pair. FRET pair includes two fluorophores that are capable of undergoing FRET to produce or eliminate a detectable signal when positioned in proximity to one another. Some examples of donors may include Alexa 488, Alexa 546, BODIPY 493, Oyster 556, Fluor (FAM), Cy3, or TTR (Tamra). Some examples of acceptors may include Cy5, Alexa 594, Alexa 647, or Oyster 656.

As described hereinabove, one or more of the aforementioned molecules may be used as a signal generator. In some embodiments, one or more of the signal generators may not be amenable to chemical destruction and a cleavable linker may be employed to associate the signal generator and the binder. In some embodiments, one or more of the signal generators may be amenable to signal destruction and the signal generator may essentially include a molecule capable of being destroyed chemically. In some embodiments, a signal generator may include a fluorophore capable of being destroyed chemically by an oxidizing agent. In some embodiments, a signal generator may essentially include cyanine, coumarin, BODIPY, ATTO 658, or ATTO 634, capable of being destroyed chemically by an oxidizing agent. In some embodiments, a signal generator may include one or more a Cy3 dye, a Cy5 dye, or a Cy7 dye capable of being destroyed or quenched.

Enzyme and Enzyme Substrates

In some embodiments, a probe may include a binder coupled to an enzyme. In some embodiments, a suitable enzyme catalyzes a chemical reaction of the substrate to form a reaction product that can bind to a receptor (e.g., phenolic groups) present in the sample or a solid support to which the sample is bound. A receptor may be exogeneous (that is, a receptor extrinsically adhered to the sample or the solid-support) or endogeneous (receptors present intrinsically in the sample or the solid-support). Signal amplification may be effected as a single enzyme may catalyze a chemical reaction of the substrate to covalently bind multiple signal generators near the target.

In some embodiments, a suitable enzyme may also be capable of being inactivated by an oxidizing agent. Examples of suitable enzymes include peroxidases, oxidases, phosphatases, esterases, and glycosidases. Specific examples of suitable enzymes include horseradish peroxidase, alkaline phosphatase, β-D-galactosidase, lipase, and glucose oxidase. In some embodiments, the enzyme is a peroxidase selected from horseradish peroxidase, cytochrome C peroxidase, glutathione peroxidase, microperoxidase, myeloperoxidase, lactoperoxidase, and soybean peroxidase.

In some embodiments, a binder and an enzyme may be embodied in a single entity, for example a protein molecule capable of binding to a target and also catalyzing a chemical reaction of substrate. In other embodiments, a binder and an enzyme may be embodied in separate entities and may be coupled by covalent bond formation or by using ligand-receptor conjugate pairs (e.g., biotin streptavidin).

An enzyme substrate may be selected depending on the enzyme employed and the target available for binding in the sample or on the solid support. For example, in embodiments including HRP as an enzyme, a substrate may include a substituted phenol (e.g., tyramine). Reaction of HRP to the tyramine may produce an activated phenolic substrate that may bind to endogeneous receptors like electron-rich moieties (such as tyrosine or tryptophan) or phenolic groups present in the surface proteins of a biological sample. In alternate embodiments, where 3-methyl-2-benzothiazolinone hydrochloride (MBTH) may be employed as a substrate along with an HRP enzyme, exogeneous receptors like p-dimethylaminobenzaldehyde (DMAB) may be adhered to the solid support or the biological sample before reacting with the substrate.

In some embodiments, an enzyme substrate may be dephosphorylated after reaction with the enzyme. The dephosphorylated reaction product may be capable of binding to endogeneous or exogeneous receptors (e.g., antibodies) in the sample or the solid-support. For example, an enzyme may include alkaline phosphatase (AP) and a substrate may include NADP, substituted phosphates (e.g., nitrophenyl phosphate), or phosphorylated biotin. The receptors may include NAD binding proteins, antibodies to the dephosphorylated reaction product (e.g., anti nitro-phenol), avidin, or streptavidin accordingly.

In some embodiments, an enzyme may include β-galactosidase and a substrate may include β-galactopyranosylglycoside of fluorescein or coumarin. Receptors may include antibodies to deglycosylated moieties (e.g., anti-fluorescein or anti-coumarin). In some embodiments, multiple enzyme combinations like HRP/AP may be used as an enzyme. A substrate may include phosphorylated substituted phenol e.g., tyrosine phosphate, which may be dephosphorylated by AP before reacting with HRP to form a reaction product capable of binding to phenolic groups or electron rich moieties-based receptors.

A reaction product of the enzyme substrate may further be capable of being providing a detectable signal. In some embodiments, enzyme substrates employed in the methods disclosed herein may include non-chromogenic or non-chemiluminescent substrates, that is a reaction of the enzyme and the enzyme substrate may not itself produce a detectable signal. Enzyme substrates employed in the methods disclosed herein may include an extrinsic signal generator (e.g., a fluorophore) as a label. The signal generator and the enzyme substrate may be attached directly (e.g., an enzyme substrate with a fluorescent label) or indirectly (e.g., through ligand-receptor conjugate pair). In some embodiments, a substrate may include protected functional groups (e.g., sulfhydryl groups). After binding of the activated substrate to the receptors, the functional group may be deprotected and conjugation to a signal generator effected using a signal generator having a thiol reactive group (e.g., maleimide or iodoacetyl).

In some embodiments, a probe may include horseradish peroxidase and the substrate is selected from substituted phenols (e.g., tyramine). In some embodiments, the horseradish peroxidase causes the activated phenolic substrate to covalently bind to phenolic groups present in the sample or a solid support to which the sample is bound. In some embodiments, a probe may include a binder coupled to HRP and a substrate may include tyramine-coupled to a fluorophore.

Chemical Agents

A chemical agent may include one or chemicals capable of modifying the signal generator, the enzyme, or the cleavable linker (if present) between the signal generator and the binder or the enzyme substrate. A chemical agent may be contacted with the sample in the form of a solid, a solution, a gel, or a suspension.

In some embodiments, a chemical agent may include oxidizing agents, for example, active oxygen species, hydroxyl radicals, singlet oxygen, hydrogen peroxide, or ozone. In some embodiments, a chemical agent may include hydrogen peroxide, potassium permanganate, sodium dichromate, aqueous bromine, iodine-potassium iodide, or t-butyl hydroperoxide One or more of the aforementioned chemical agents may be used in the methods disclosed herein depending upon the susceptibility of the signal generator, of the enzyme, of the binder, of the target, or of the biological sample to the chemical agent. In some embodiments, a chemical agent that essentially does not affect the integrity of the binder, the target, and the biological sample may be employed. In some embodiments, a chemical agent that does not affect the specificity of binding between the binder and the target may be employed.

In some embodiments, where two or more (up to four) signal generators may be employed simultaneously, a chemical agent may be capable of selectively modifying one or more signal generators. Susceptibility of different signal generators to a chemical agent may depend, in part, to the concentration of the signal generator, temperature, or pH. For example, two different fluorophores may have different susceptibility to an oxidizing agent depending upon the concentration of the oxidizing agent.

In some embodiments, a chemical agent may essentially include an oxidizing agent. In other embodiments, a chemical agent may essentially include a basic solution of an oxidizing agent. In some specific embodiments, a basic solution may have a pH in a range of from about 8 to about 10. In some embodiments, a basic solution (e.g., sodium biocarbonate) may have pH of about 10.

A suitable oxidizing agent may be selected from peroxide, sodium periodate, or ozone. In some embodiments, a suitable oxidizing agent may include peroxide or a peroxide source and the basic solution may include hydrogen peroxide. The concentration of hydrogen peroxide in the basic solution may be selected to substantially oxidize the fluorescent signal generator in a predetermined period of time. In some embodiments, the concentration of hydrogen peroxide in the basic solution may be selected to substantially inactivate both the fluorescent signal generator and the enzyme in a given period of time. The concentration of hydrogen peroxide in the basic solution may be selected such that the integrity of the sample, the targets, the binder, or the target-binder specificity may be maintained.

In some embodiments, a basic solution may include hydrogen peroxide in an amount that is in a range of from about 0.5 volume percent to about 5 volume percent, in a range of from about 1 volume percent to about 4 volume percent, or in a range of from about 1.5 volume percent to about 3.5 volume percent. In some specific embodiments, a basic solution may include hydrogen peroxide in an amount that is in a range of about 3 volume percent.

In some embodiments, the basic solution may not include reagents that strip the binders, the targets or both the binders and the targets from the sample such as reducing agents or surfactants.

Sequentially Analyzing a Biological Sample, Contacting and Binding the Probe

A biological sample may be contacted with a probe to bind the probe to a target in the biological sample. In some embodiments, a target may not be easily accessible for binding with the probe and a biological sample may be further processed to facilitate the binding between the target and the binder in the probe, for example through antigen recovery, enzymatic digestion, epitope retrieval, or blocking.

In some embodiments, a probe may be contacted with the biological sample in the form of a solution. In some embodiments, a probe may include a binder coupled to a label (fluorescent signal generator or an enzyme). The binder and the label (signal generator or enzyme) may be embodied in a single molecule and the probe solution may be applied in a single step. Alternatively, the binder and the label (signal generator or enzyme) may be distinct entities and the probe solution may be applied in a single step or multiple steps. In all embodiments, a control probe may further be bonded to one or more targets in the sample.

Depending on the nature of the binder, the target, and the binding between the two, sufficient contact time may be allowed. In some embodiments, an excess of probe molecules (and accordingly binder molecules) may be employed to ensure all the targets in the biological sample are bound. After a sufficient time has been providing for the binding action, the sample may be contacted with a wash solution (for example an appropriate buffer solution) to wash away any unbound probes. Depending on the concentration and type of probes used, a biological sample may be subjected to a number of washing steps with the same or different washing solutions being employed in each step.

In some embodiments, the biological sample may be contacted with more than one probe in the first binding step. The plurality of probes may be capable of binding different targets in the biological sample. For example, a biological sample may include two targets: target1 and target2 and two sets of probes may be used in this instance: probe1 (having binder1 capable of binding to target1) and probe2 (having binder2 capable of binding to target2). A plurality of probes may be contacted with the biological sample simultaneously (for example, as a single mixture) or sequentially (for example, a probe1 may be contacted with the biological sample, followed by washing step to remove any unbound probe1, followed by contacting a probe2 with the biological sample, and so forth).

The number of probes that may be simultaneously bound to the target may depend on the type of detection employed, that is, the spectral resolution achievable. For example, for fluorescence-based signal generators, four different probes (providing four spectrally resolvable fluorescent signals) may be employed in accordance with the disclosed methods. Spectrally resolvable, in reference to a plurality of fluorescent signal generators, indicates that the fluorescent emission bands of the signal generators are sufficiently distinct, that is, sufficiently non-overlapping, such that, binders to which the respective signal generators are attached may be distinguished on the basis of the fluorescent signal generated by the respective signal generators using standard photodetection systems.

In some embodiments, a biological sample may be essentially contacted with four or less than four probes in the first binding step. In embodiments employing enzyme-based probes, the number of probes that may be simultaneously bound to the target may also depend on the number of different enzymes and their corresponding substrates available.

In some embodiments, a biological sample may include a whole cell, a tissue sample, or the biological sample may be adhered to a microarray, a gel, or a membrane. In some embodiments, a biological sample may include a tissue sample. The tissue sample may be obtained by a variety of procedures including, but not limited to surgical excision, aspiration or biopsy. The tissue may be fresh or frozen. In some embodiments, the tissue sample may be fixed and embedded in paraffin. The tissue sample may be fixed or otherwise preserved by conventional methodology; the choice of a fixative may be determined by the purpose for which the tissue is to be histologically stained or otherwise analyzed. The length of fixation may depend upon the size of the tissue sample and the fixative used. For example, neutral buffered formalin, Bouin's or paraformaldehyde, may be used to fix or preserve a tissue sample.

In some embodiments, the tissue sample may be first fixed and then dehydrated through an ascending series of alcohols, infiltrated and embedded with paraffin or other sectioning media so that the tissue sample may be sectioned. In an alternative embodiment, a tissue sample may be sectioned and subsequently fixed. In some embodiments, the tissue sample may be embedded and processed in paraffin. Examples of paraffin that may be used include, but are not limited to, Paraplast, Broloid, and Tissuemay. Once the tissue sample is embedded, the sample may be sectioned by a microtome into sections that may have a thickness in a range of from about three microns to about five microns. Once sectioned, the sections may be attached to slides using adhesives. Examples of slide adhesives may include, but are not limited to, silane, gelatin, poly-L-lysine. In embodiments, if paraffin is used as the embedding material, the tissue sections may be deparaffinized and rehydrated in water. The tissue sections may be deparaffinized, for example, by using organic agents (such as, xylenes or gradually descending series of alcohols).

In some embodiments, aside from the sample preparation procedures discussed above, the tissue section may be subjected to further treatment prior to, during, or following immunohistochemistry. For example, in some embodiments, the tissue section may be subjected to epitope retrieval methods, such as, heating of the tissue sample in citrate buffer. In some embodiments, a tissue section may be optionally subjected to a blocking step to minimize any non-specific binding.

In some embodiments, the biological sample or a portion of the biological sample, or targets present in the biological sample may be adhered on the surface of DNA microarrays, on the surface of protein microarrays, or on the surface of solid supports (such as gels, blots, glass slides, beads, or ELISA plates). In some embodiments, targets present in the biological sample may be adhered on the surface of solid supports. Targets in the biological sample may be adhered on the solid support by physical bond formation, by covalent bond formation, or both.

In some embodiments, the targets in the biological sample may be adhered to membranes and probed sequentially using the methods disclosed herein. In some embodiments, targets in the biological sample may be processed before contacting the sample with the membrane. For example, embodiments involving methods for probing protein targets in a tissue sample may include the step of extracting the target proteins a biological sample of tissue homogenate or an extract. Solid tissues or whole cells may be first broken down mechanically using a blender (for larger sample volumes), using a homogenizer (smaller volumes), or by sonication. Different cell compartments and organelles may be separated using filtration and centrifugation techniques. Detergents, salts, and buffers may also be employed to encourage lysis of cells and to solubilize proteins. Similarly, embodiments involving methods for probing nucleic acids may include the step of preparing DNA or RNA fragments, for example using restriction endonucleases (for DNA).

In some embodiments, targets extracted from the biological sample may be further separated by gel electrophoresis. Separation of targets may be by isoelectric point (pI), molecular weight, electric charge, or a combination of these factors. The nature of the separation may depend on the treatment of the sample and the nature of the gel. A suitable gel may be selected from a polyacrylamide gel, an SDS-polyacrylamide gel, or an agarose gel.

A suitable membrane may be selected such that the membrane has non-specific target binding properties. In some embodiments, a suitable membrane may be selected from a polyvinylidene fluoride membrane, a nitrocellulose membrane, or a nylon membrane. In some embodiment, a suitable membrane may be selected such that the membrane may be substantially stable to multiple probing. In embodiments involving probing of targets using protein probes, the membranes may be blocked using a blocking solution to prevent non-specific binding of protein probes to the membranes. In embodiments, involving probing of DNA fragments, the DNA gel may be treated with a dilute HCL solution or an alkaline solution to facilitate more efficient transfer of the DNA from the gel to the membrane.

In some embodiments, the membrane may be subjected to temperatures in a range of about 60° C. to about 100° C. to covalently bind the targets to the membrane, for example DNA targets to a nitrocellulose membrane. In some embodiments, the membrane may be exposed to ultraviolet radiation to covalently bind the targets to the membrane, for example DNA targets to a nylon membrane. In some embodiments, the targets in the biological sample may not be separated by electrophoresis before blotting on a membrane and may be probed directly on a membrane, for example, in dot blot techniques.

Following the preparation of the tissue sample or the membrane, a probe solution (e.g., labeled-antibody solution) may be contacted with the tissue section or the membrane for a sufficient period of time and under conditions suitable for binding of binder to the target (e.g., antigen). As described earlier, two detection methods may be used: direct or indirect. In a direct detection, a signal generator-labeled primary antibody (e.g., fluorophore-labeled primary antibody or enzyme-labeled primary antibody) may be incubated with an antigen in the tissue sample or the membrane, which may be visualized without further antibody interaction. In an indirect detection, an unconjugated primary antibody may be incubated with an antigen and then a labeled secondary antibody may bind to the primary antibody. Signal amplification may occur as several secondary antibodies may react with different epitopes on the primary antibody. In some embodiments two or more (at most four) primary antibodies (labeled or unlabeled) may be contacted with the tissue sample. Unlabeled antibodies may be then contacted with the corresponding labeled secondary antibodies. In alternate embodiments, a primary antibody and specific binding ligand-receptor pairs (such as biotin-streptavidin) may be used. The primary antibody may be attached to one member of the pair (for example biotin) and the other member (for example streptavidin) may be labeled with a signal generator or an enzyme. The secondary antibody, avidin, streptavidin, or biotin may be each independently labeled with a signal generator or an enzyme.

In embodiments where the primary antibody or the secondary antibody may be conjugated to an enzymatic label, a fluorescent signal generator-coupled substrate may be added to provide visualization of the antigen. In some embodiments, the substrate and the fluorescent signal generator may be embodied in a single molecule and may be applied in a single step. In other embodiments, the substrate and the fluorescent signal generator may be distinct entities and may be applied in a single step or multiple steps.

An enzyme coupled to the binder may react with the substrate to catalyze a chemical reaction of the substrate to covalently bind the fluorescent signal generator-coupled substrate the biological sample or the solid support to which the sample is bound. In some embodiments, an enzyme may include horseradish peroxidase and the substrate may include tyramine. Reaction of the horseradish peroxidase (HRP) with the tyramine substrate may cause the tyramine substrate to covalently bind to phenolic groups present in the sample or a solid support to which the sample is bound. In embodiments employing enzyme-substrate conjugates, signal amplification may be attained as one enzyme may catalyze multiple substrate molecules. In some embodiments, methods disclosed herein may be employed to detect low abundance targets using indirect detection methods (e.g., using primary-secondary antibodies), using HRP-tyramide signal amplification methods, or combinations of both (e.g., indirect HRP-tyramide signal amplification methods). Incorporation of signal amplification techniques into the methods disclosed herein and correspondingly the type of signal amplification techniques incorporated might depend on the sensitivity required for a particular target and the number of steps involved in the protocol.

Observing a Signal from the Probe

A signal from the signal generator may be detected using a detection system. The nature of the detection system used may depend upon the nature of the signal generators used. The detection system may include an electron spin resonance (ESR) detection system, a charge coupled device (CCD) detection system (e.g., for radioisotopes), a fluorescent detection system, an electrical detection system, a photographic film detection system, a chemiluminescent detection system, an enzyme detection system, an atomic force microscopy (AFM) detection system (for detection of microbeads), a scanning tunneling microscopy (STM) detection system (for detection of microbeads), an optical detection system, a near field detection system, or a total internal reflection (TIR) detection system.

One or more of the aforementioned techniques may be used to observe one or more characteristics of a signal from a signal generator (coupled with a binder or coupled with an enzyme substrate). In some embodiments, signal intensity, signal wavelength, signal location, signal frequency, or signal shift may be determined using one or more of the aforementioned techniques. In some embodiments, one or more aforementioned characteristics of the signal may be observed, measured, and recorded.

In some embodiments, a signal generator (coupled with a binder or couple with an enzyme substrate) may include a fluorophore and fluorescence wavelength or fluorescent intensity may be determined using a fluorescence detection system. In some embodiments, a signal may be observed in situ, that is, a signal may be observed directly from the signal generator associated through the binder to the target in the biological sample. In some embodiments, a signal from the signal generator may be analyzed within the biological sample, obviating the need for separate array-based detection systems.

In some embodiments, observing a signal may include capturing an image of the biological sample. In some embodiments, a microscope connected to an imaging device may be used as a detection system, in accordance with the methods disclosed herein. In some embodiments, a signal generator (such as, fluorophore) may be excited and the signal (such as, fluorescence signal) obtained may be observed and recorded in the form of a digital signal (for example, a digitalized image). The same procedure may be repeated for different signal generators (if present) that are bound in the sample using the appropriate fluorescence filters.

Applying a Chemical Agent to Modify the Signal

A chemical agent may be applied to the sample to modify the signal. In some embodiments, signal modification may include one or more of a change in signal characteristic, for example, a decrease in intensity of signal, a shift in the signal peak, a change in the resonant frequency, or cleavage (removal) of the signal generator resulting in signal removal. In some embodiments, a chemical agent may be applied to modify the signal by substantially inactivating the fluorescent signal generator and the enzyme (if employed). In some embodiments, a chemical agent may include an oxidizing agent, which may substantially oxidize the fluorescent signal generator. In some embodiments, a chemical agent may be applied to modify the signal by substantially oxidizing the cleavable linkage to cleave off the signal generator.

In some embodiments, a chemical agent may be in the form of a solution and the sample may be contacted with the chemical agent solution for a predetermined amount of time. In some embodiments, a chemical agent may be a basic solution having an oxidizing agent. The concentration of the basic solution and the contact time may be dependent on the type of signal modification desired. In some embodiments, a chemical agent solution may be contacted with the sample and the oxidation step may be performed for less than 30 minutes. In some embodiments, the oxidation step may be performed for less than 15 minutes. In some embodiments, the oxidation step may be performed for about 30 seconds to about 15 minutes. In some embodiments, the oxidation step may be performed for about 5 minutes. In some embodiments, the oxidation step may be performed at room temperature.

In some embodiments, the contacting conditions for the basic solution may be selected such that the binder, the target, the biological sample, and binding between the binder and the target may not be affected. In some embodiments, an oxidizing agent may only affect the signal generator and the enzyme (if employed) and the oxidizing agent may not affect the target/binder binding or the binder integrity. Thus by way of example, a binder may include a primary antibody or a primary antibody/secondary combination. An oxidizing agent according to the methods disclosed herein may only affect the signal generator, and the primary antibody or primary antibody/secondary antibody combination may essentially remain unaffected. In some embodiments, a binder (such as, a primary antibody or primary antibody/secondary antibody combination) may remain bound to the target in the biological sample after contacting the sample with the oxidizing agent.

In some embodiments, a binder may remain bound to the target in the biological sample after contacting the sample with the oxidizing agent and the binder integrity may remain essentially unaffected (for example, an antibody may not substantially denature or elute in the presence of a chemical agent). In some embodiments, after application of the oxidizing agent to the sample less than 25 percent of the binders may be stripped from the targets in the biological sample. In some embodiments, after application of the oxidizing agent to the sample less than 20, less than 15 percent, less than 10 percent, or less than 5 percent of the binders may be stripped from the targets in the biological sample.

In some embodiments, a characteristic of the signal may be observed after contacting the sample with the oxidizing agent to determine the effectiveness of the signal modification. For example, a color may be observed before application of the oxidizing agent and the color may be absent after application of the oxidizing agent. In another example, fluorescence intensity from a fluorescent signal generator may be observed before contacting with the oxidizing agent and after contacting with the oxidizing agent. In some embodiments, a decrease in signal intensity by a predetermined amount may be referred to as signal modification. In some embodiments, modification of the signal may refer to a decrease in the signal intensity by an amount in a range of greater than about 50 percent. In some embodiments, modification of the signal may refer to a decrease in the signal intensity by an amount in a range of greater than about 60 percent. In some embodiments, modification of the signal may refer to a decrease in the signal intensity by an amount in a range of greater than about 80 percent.

Contacting the Sample with a Subsequent Probe and Binding to a Subsequent Target The biological sample or the sample bound to a solid support may be contacted with a subsequent probe using one or more procedures described herein above for the first probe. The subsequent probe may be capable of binding to target different from the target bound in the earlier steps. In embodiments where a plurality of probes may be contacted with the biological sample in the earlier probe contact steps, the subsequent probe may be capable of binding a target different from the targets bound by the earlier probe set. In some embodiments, a biological sample may be contacted with a plurality of probes in the subsequent probe contact step. In embodiments where binders coupled to enzymes may be employed as probes, binding steps may further include reacting steps involving reaction of the enzyme with an enzyme substrate coupled to fluorescent signal generator.

In some embodiments, the signal generator (e.g., a fluorescent signal generator) used in the different binding steps may be the same, that is, detectable in the same detection channel. Methods employing the same signal generator in different binding steps may allow for detection of multiple targets when limited number of detection channels are available. In some embodiments, where a set of probes (2 to 4 probes) may be employed in the first binding step, the subsequent probes may include the same signal generators as in the earlier binding steps. For example, a first binding step may include Cy3, Cy5, and Cy7-conjugated different binders. In some embodiments, the subsequent binding steps may also include the same dye set, that is, Cy3, Cy5, and Cy7.

In some embodiments, the signal generator (e.g., a fluorescent signal generator) used in the different binding steps may be different, that is, independently detectable in different detection channels. For example, in some embodiments, a first probe may include a Cy3 dye, which has a fluorescent emission wavelength in the green region and a subsequent probe may include a Cy7 dye, which has a fluorescent emission wavelength in the red region.

In embodiments employing binder-coupled enzymes as probes, the enzymes and the substrates employed in the different binding and reacting steps may be the same. An oxidizing agent may inactivate the earlier enzyme before binding the sample to a subsequent enzyme to prevent cross-reaction of the earlier enzyme with the subsequent substrate. For example, a first binding and reacting step may include binder coupled to HRP and tyramine coupled to a first fluorophore. The oxidizing step may involve the steps of substantially oxidizing the fluorophore and substantially inactivating the HRP. In some embodiments, oxidation and inactivation steps may occur simultaneously. In some embodiments, oxidation and inactivation steps may occur sequentially. After the oxidation and inactivation steps, the sample may be contacted with a subsequent binder coupled to HRP, which may be further reacted with tyramine coupled to a second fluorophore. Similarly, the subsequent binding and reacting steps may be affected using multiple iterations of HRP-tyramine as enzyme substrate conjugates, each binding and reacting step followed by the oxidation and inactivation step. The first fluorophore and the subsequent fluorophores may be the same or different depending on the number of detection channels available for detection.

In some embodiments, the first binding step may include a set of probes (e.g., 2 to 4 probes), each probe including a binder capable of binding to a different target and each enzyme capable of catalyzing a chemical reaction of a different substrate. For example, in one embodiment, the first probe set may include a binder1 coupled to HRP and a binder2 coupled to AP. The reacting step may include contacting the sample with tyramine-coupled to Cy3 and NADP-coupled to Cy7. Following reaction of the enzymes with their corresponding substrates and observing the signals, the cyanine dyes may be oxidized and the enzymes inactivated by addition of a suitable oxidizing agent. The subsequent probing steps may include the same set of binder-enzyme and substrate-fluorophore pairs or different set of binder-enzyme and substrate-fluorophore pairs. The plurality of probes and the substrate-signal generator may be contacted with the biological sample simultaneously (for example, as a single mixture) or sequentially (for example, a probe1 may be contacted with the biological sample, followed by washing step to remove any unbound probe1, followed by contacting a probe2 with the biological sample, and so forth).

Observing a Subsequent Signal from a Subsequent Probe.

One or more detection methods described hereinabove may be used to observe one or more characteristics of a subsequent (e.g., second, third, etc.) signal from a subsequent signal generator (present in the subsequent probe). In some embodiments, signal intensity, signal wavelength, signal location, signal frequency, or signal shift may be determined using one or more of the aforementioned techniques. Similar to the first signal, a subsequent signal (for example, a fluorescence signal) obtained may be recorded in the form of a digital signal (for example, a digitalized image). In some embodiments, observing a subsequent signal may also include capturing an optical image of the biological sample.

Reiteration of the Contacting, Binding, and Observing Steps

In some embodiments, after contacting the sample with a subsequent (e.g., second, third, etc.) probe, oxidation of the signal generator, and subsequent probe administration may be repeated multiple times. In some embodiments, after observing a second signal from the second probe, the biological sample may be contacted with an oxidizing agent to modify the signal from the second probe. Furthermore, a third probe may be contacted with the biological sample, wherein the third probe may be capable of binding a target different from the first and the second probes. Likewise, a signal from the third probe may be observed followed by application of oxidizing agent to modify the signal. The binding, observing, and oxidation steps may be repeated iteratively multiple times using an $n^{th}$ probe capable of binding to additional targets to provide the user with information about a variety of targets using a variety of probes and/or signal generators. In embodiments where binders coupled to enzymes may be employed as probes, binding steps may further include reacting steps involving reaction of the enzyme with an enzyme substrate coupled to fluorescent signal generator. In some embodiments, the oxidation, binding, reacting (if applicable), and observing steps may be repeated one or more time. In some embodiments, the oxidation, binding, reacting (if applicable), and observing steps may be repeated at least 5, at least 10, or at least 20 times.

In some embodiments, a series of probes may be contacted with the biological sample in a sequential manner to obtained a multiplexed analysis of the biological sample. In some embodiments, a series of probe sets (including at most 4 probes in one set) may be contacted with the biological sample in a sequential manner to obtained a multiplexed analysis of the biological sample. Multiplexed analysis generally refers to analysis of multiple targets in a biological sample using the same detection mechanism.

Contacting the Sample with One or More Morphological Stain

In some embodiments, a biological sample may include a cell or a tissue, and the sample may be contacted with a morphological stain before, during, or after the contacting step with the first probe or subsequent probe. A morphological stain may include a dye that may stain different cellular components, in order to facilitate identification of cell type or disease status. In some embodiments, the morphological stain may be readily distinguishable from the signal generators in the probes, that is, the stain may not emit signal that may overlap with signal from the probe. For example, for a fluorescent morphological stain, the signal from the morphological stain may not autofluoresce in the same wavelength as the fluorophores used in the probes.

A morphological stain may be contacted with the biological sample before, during, or after, any one of the aforementioned steps. In some embodiments, a morphological stain may be contacted with biological sample along with the first probe contact step. In some embodiments, a morphological stain may be contacted with the biological sample before contacting the sample with a chemical agent and after binding the first probe to the target. In some embodiments, a morphological stain may be contacted with a biological sample after contacting the sample with a chemical agent and modifying the signal. In some embodiments, a morphological stain may be contacted with a biological sample along with the second probe contact step. In some embodiments, a biological sample may be contacted with the morphological stain after binding the second probe to the target. In some embodiments, where the morphological stains may result in background noise for the fluorescent signal from the signal generator, the morphological stains may be contacted with the biological sample after the probing, oxidizing and reprobing steps. For example, morphological stains like H&E may be sequentially imaged and registered after the methods disclosed herein.

In some embodiments, chromophores, fluorophores, or enzyme/enzyme substrates may be used as morphological stains. Suitable examples of chromophores that may be used as morphological stains (and their target cells, subcellular compartments, or cellular components) may include, but are not limited to, Eosin (alkaline cellular components, cytoplasm), Hematoxylin (nucleic acids), Orange G (red blood, pancreas, and pituitary cells), Light Green SF (collagen), Romanowsky-Giemsa (overall cell morphology), May-Grunwald (blood cells), Blue Counterstain (Trevigen), Ethyl Green (CAS) (amyloid), Feulgen-Naphthol Yellow S (DNA), Giemsa (differentially stains various cellular compartments), Methyl Green (amyloid), pyronin (nucleic acids), Naphthol-Yellow (red blood cells), Neutral Red (nuclei), Papanicolaou stain (a mixture of Hematoxylin, Eosin Y, Orange G and Bismarck Brown mixture (overall cell morphology)), Red Counterstain B (Trevigen), Red Counterstain C (Trevigen), Sirius Red (amyloid), Feulgen reagent (pararosanilin) (DNA), Gallocyanin chrom-alum (DNA), Gallocyanin chrom-alum and Naphthol Yellow S (DNA), Methyl Green-Pyronin Y (DNA), Thionin-Feulgen reagent (DNA), Acridine Orange (DNA), Methylene Blue (RNA and DNA), Toluidine Blue (RNA and DNA), Alcian blue (carbohydrates), Ruthenium Red (carbohydrates), Sudan Black (lipids), Sudan IV (lipids), Oil Red-O (lipids), Van Gieson's trichrome stain (acid fuchsin and picric acid mixture) (muscle cells), Masson trichrome stain (hematoxylin, acid fuchsin, and Light Green mixture) (stains collagen, cytoplasm, nucleioli differently), Aldehyde Fuchsin (elastin fibers), or Weigert stain (differentiates reticular and collagenous fibers).

Examples of suitable fluorescent morphological stains (and their target cells, subcellular compartments, or cellular components if applicable) may include, but are not limited to: 4',6-diamidino-2-phenylindole (DAPI) (nucleic acids), Eosin (alkaline cellular components, cytoplasm), Hoechst 33258 and Hoechst 33342 (two bisbenzimides) (nucleic acids), Propidium Iodide (nucleic acids), Spectrum Orange (nucleic acids), Spectrum Green (nucleic acids), Quinacrine (nucleic acids), Fluorescein-phalloidin (actin fibers), Chromomycin A 3 (nucleic acids), Acriflavine-Feulgen reaction (nucleic acid), Auramine O-Feulgen reaction (nucleic acids), Ethidium Bromide (nucleic acids). Nissl stains (neurons), high affinity DNA fluorophores such as POPO, BOBO, YOYO and TOTO and others, and Green Fluorescent Protein fused to DNA binding protein, such as histones, ACMA, Quinacrine and Acridine Orange.

Examples of suitable enzymes (and their primary cellular locations or activities) may include, but are not limited to, ATPases (muscle fibers), succinate dehydrogenases (mitochondria), cytochrome c oxidases (mitochondria), phosphorylases (mitochondria), phosphofructokinases (mitochondria), acetyl cholinesterases (nerve cells), lactases (small intestine), acid phosphatases (lysosomes), leucine aminopeptidases (liver cells), dehydrogenases (mitochondria), myodenylate deaminases (muscle cells), NADH diaphorases (erythrocytes), and sucrases (small intestine).

In some embodiments, a morphological stain may be stable towards an oxidizing agent, that is, the signal generating properties of the morphological stain may no be substantially affected by the oxidizing agent. In some embodiments, where a biological sample may be stained with a probe and a morphological stain at the same time, application of oxidizing agent to modify the signal from the probe may not modify the signal from the morphological stain. In some embodiments, a morphological stain may be used as a control to co-register the molecular information (obtained through the iterative probing steps) and the morphological information (obtained through the morphological stains).

Contacting the Sample with One or More Control Probe

In some embodiments, a control probe may be bonded to one or more targets in the biological sample. In some embodiments, a control probe may be bonded to the targets along with the first probe contact step. In some embodiments, a control probe may be applied to the biological sample simultaneously with the first probe. In some embodiments, a control probe may be applied to the biological sample sequentially, that is before or after the application of the first probe, but before application of the oxidizing agent.

A control probe may include a signal generator that is stable towards an oxidizing agent or the signal generating properties of the signal generator are not substantially effected when contacted with the oxidizing agent. A signal generator may include a radioisotope that is stable to the oxidizing agent or a fluorophore that is stable to the oxidizing agent. A suitable radioisotope may include $P^{32}$ or $H^3$, $^{14}C$, $^{125}I$ or $^{131}I$. A suitable fluorophore may include DAPI.

In some embodiments, a suitable signal generator may be coupled to a binder to form a control probe. For example, a radioactive label may be coupled to an antibody to form a control probe and the antibody may bind to one or more target antigens present in the biological sample. In other embodiments, a suitable signal generator may be capable of binding to one more targets in the sample and also providing a detectable signal, which is stable in the presence of the oxidizing agent. For example, a suitable control probe may be DAPI, which is capable of binding to nucleic acids in the sample and also capable of providing a fluorescent signal that is stable to the oxidizing agent.

In some embodiments, a control probe may be employed in the methods disclosed herein to provide an indication of the stability of the targets to the iterative staining steps. For example, a control probe may be bonded to a known target in the sample and a signal from the control observed and quantified. The control signal may be then monitored during the iterative staining steps to provide an indication of the stability of the targets or binders to the oxidizing agents. In some embodiments, a quantitative measure (for example, signal intensity) of the control signal may be monitored to quantify the amount of targets present in the sample after the iterative probing steps.

In some embodiments, a control probe may be employed to obtain quantitative information of the sample of interest, for example concentration of targets in the sample or molecular weight of the targets in the sample. For example, a control target (having known concentration or known molecular weight) may be loaded along with the sample of interest in a blotting technique. A control probe may be bonded to the control target and a control signal observed. The control signal may be then correlated with the signals observed from the sample of interest using methods described herein below.

In some embodiments, a control probe may be employed in the methods disclosed herein to provide for co-registration of multiple molecular information (obtained through the iterative probing steps) and the morphological information (obtained, e.g., using DAPI). In some embodiments, methods disclosed herein may include co-registration of multiple fluorescent images with the bright-field morphological images obtained e.g., using H&E. In some embodiments, the probes employed in the iterative probing steps may not have any common compartmental information that may be used to register with the H&E images. A control probe like a DAPI nuclear stain may be employed to co-register the nucleus stained with hematoxylin in the bright-field images with the fluorescent images. The fluorescent images and the bright-field images may be co-registered using image registration algorithms that may be grouped in two categories: intensity-based and feature-based techniques.

Correlating the First Signal and the Subsequent Signals

In some embodiments, a first signal, a subsequent signal, or the first signal and the subsequent signals may be analyzed to obtain information regarding the biological sample. For example, in some embodiments, a presence or absence of a first signal may indicate the presence or absence of the first target (capable of binding to the first binder) in the biological sample. Similarly, the presence or absence of a second signal may indicate the presence or absence of the second target (capable of binding to the second binder in the biological sample). In embodiments where multiple targets may be analyzed using a plurality of probes, the presence or absence of a particular signal may indicate the presence or absence of corresponding target in the biological sample.

In some embodiments, the observing steps may include a quantitative measurement of at least one target in the sample. In some embodiments, an intensity value of a signal (for example, fluorescence intensity) may be measured and may be correlated to the amount of target in the biological sample. A correlation between the amount of target and the signal intensity may be determined using calibration standards. In some embodiment, intensity values of the first and second signals may be measured and correlated to the respective target amounts. In some embodiments, by comparing the two signal intensities, the relative amounts of the first target and the second target (with respect to each other or with respect to a control) may be ascertained. Similarly, where multiple targets may be analyzed using multiple probes, relative amounts of different targets in the biological sample may be determined by measuring different signal intensities. In some embodiments, one or more control samples may be used as described hereinabove. By observing a presence or absence of a signal in the samples (biological sample of interest versus a control), information regarding the biological sample may be obtained. For example by comparing a diseased tissue sample versus a normal tissue sample, information regarding the targets present in the diseased tissue sample may be obtained. Similarly by comparing signal intensities between the samples (i.e., sample of interest and one or more control), information regarding the expression of targets in the sample may be obtained.

In some embodiments, the observing steps include co-localizing at least two targets in the sample. Methods for co-localizing targets in a sample are described in U.S. patent application Ser. No. 11/686,649, entitled "System and Methods for Analyzing Images of Tissue Samples", filed on Mar. 15, 2007; U.S. patent application Ser. No. 11/500,028, entitled "System and Method for Co-Registering Multi-Channel Images of a Tissue Micro Array", filed on Aug. 7, 2006; U.S. patent application Ser. No. 11/606,582, entitled "System and Methods for Scoring Images of a Tissue Micro Array, filed on Nov. 30, 2006, and S. application Ser. No. 11/680,063, entitled Automated Segmentation of Image Structures, filed on Feb. 28, 2007, each of which is herein incorporated by reference.

In some embodiments, a location of the signal in the biological sample may be observed. In some embodiments, a localization of the signal in the biological signal may be observed using morphological stains. In some embodiments relative locations of two or more signals may be observed. A location of the signal may be correlated to a location of the target in the biological sample, providing information regarding localization of different targets in the biological sample. In some embodiments, an intensity value of the signal and a location of the signal may be correlated to obtain information regarding localization of different targets in the biological sample. For examples certain targets may be expressed more in the cytoplasm relative to the nucleus, or vice versa. In some embodiments, information regarding relative localization of targets may be obtained by comparing location and intensity values of two or more signals.

In embodiments employing blotting techniques, the observing steps may include observing a location of the signal on the blot. The location of the signal in the blot may be then correlated with calibration standards loaded along with the sample in the gel to obtain information regarding the molecular weight of the targets in the different bands. In some embodiments, a location of the signal on the blot may be correlated to a molecular weight of the target and the isoelectric point of the target, e.g., in 2D-PAGE. In some embodiments, structural proteins such as actin or tubulin may be probed using control probes in western blots to quantify the amount of targets in the sample.

In some embodiments, one or more of the observing or correlating step may be performed using computer-aided means. In embodiments where the signal(s) from the signal generator may be stored in the form of digital image(s), computer-aided analysis of the image(s) may be conducted. In some embodiments, images (e.g., signals from the probe(s) and morphological stains) may be overlaid using computer-aided superimposition to obtain complete information of the biological sample, for example topological and correlation information.

In some embodiments, one or more of the aforementioned may be automated and may be performed using automated systems. In some embodiments, all the steps may be performed using automated systems.

The methods disclosed herein may find applications in analytic, diagnostic, and therapeutic applications in biology and in medicine. In some embodiments, the methods disclosed herein may find applications in histochemistry, particularly, immunohistochemistry. Analysis of cell or tissue samples from a patient, according to the methods described herein, may be employed diagnostically (e.g., to identify patients who have a particular disease, have been exposed to a particular toxin or are responding well to a particular therapeutic or organ transplant) and prognostically (e.g., to identify patients who are likely to develop a particular disease, respond well to a particular therapeutic or be accepting of a particular organ transplant). The methods disclosed herein, may facilitate accurate and reliable analysis of a plurality (e.g., potentially infinite number) of targets (e.g., disease markers) from the same biological sample.

Example 1

Selective Oxidation Using Hydrogen Peroxide of Cyanine Dyes without Affecting DAPI A solution of hydrogen peroxide ($H_2O_2$) was prepared in a sodium bicarbonate buffer by mixing 1 volume of 1M sodium bicarbonate, 3 volumes of water, and 1 volume of 30 percent (v/v) hydrogen peroxide. pH of sodium bicarbonate was adjusted to a pH 10 using sodium hydroxide, prior to mixing with hydrogen peroxide.

Three separate solutions of cyanine dyes: Cy3, Cy5, and Cy7 were prepared in water at a concentration of about 2 µM. An aliquot of a cyanine dye solution was mixed with an aliquot of the $H_2O_2$ solution to prepare a sample solution with a final concentration of about 3 volume percent $H_2O_2$ and 1 micromolar 1 µM cyanine dye (Samples 1 (Cy3), 2 (Cy5), and 3 (Cy7)). A 1 µM cyanine dye solution in water (without $H_2O_2$) was used as a control.

Figure 2:
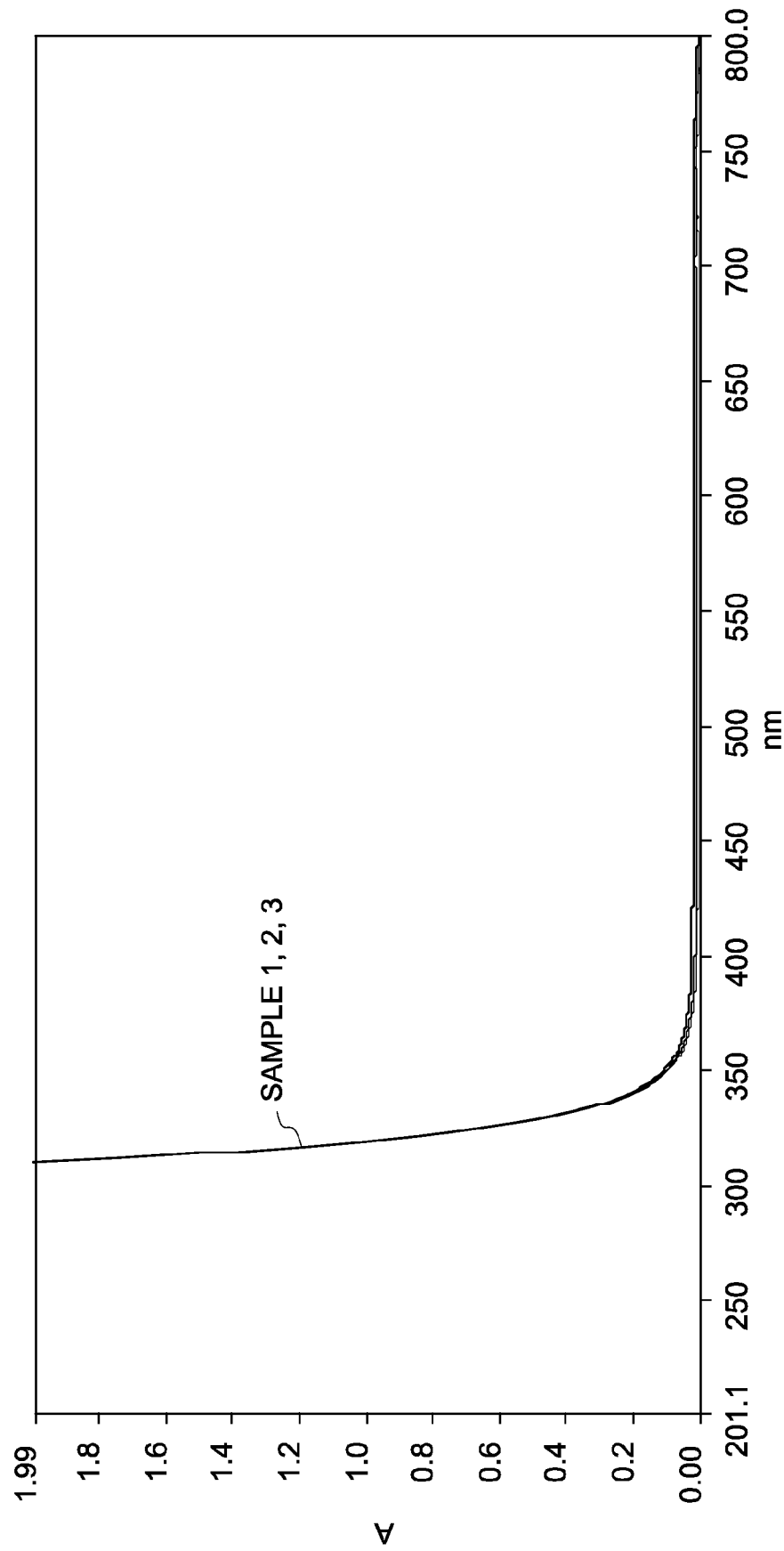
FIG. 2 shows the absorbance spectra for Samples 1, 2, and 3 as a function of wavelength.

Oxidation reaction of the cyanine dye was monitored by measuring absorbance spectrum of the dye on an ultraviolet/visible (UV/Vis) spectrophotometer as a function of time. FIG. 1 shows the absorbance spectra of Sample 1 as a function of wavelength, after duration of 10 minutes and 15 minutes. The absorbance value decreased considerably when compared with the control. FIG. 2 shows the absorbance values for Samples 1, 2, and 3 as a function of wavelength. The absorbance of the Samples 1, 2 and 3 reduced to zero after a duration of time exhibiting chemical destruction of the dye by $H_2O_2$. The time duration for the Samples 1, 2 and 3 was different for the different dye: 19 minutes for Sample 1, 15 minutes for Sample 2, and 3 minutes for Sample 3.

A solution of 4',6-diamidino-2-phenylindole (DAPI) was prepared in water at a concentration of about 57 µM. An aliquot of DAPI solution was mixed with an aliquot of the $H_2O_2$ solution to prepare a solution with a final concentration of about 3 volume percent $H_2O_2$ and 10 µg/mL DAPI (Sample 4). A 10 µg/mL DAPI solution in water (without $H_2O_2$) was used as a control.

Figure 3:
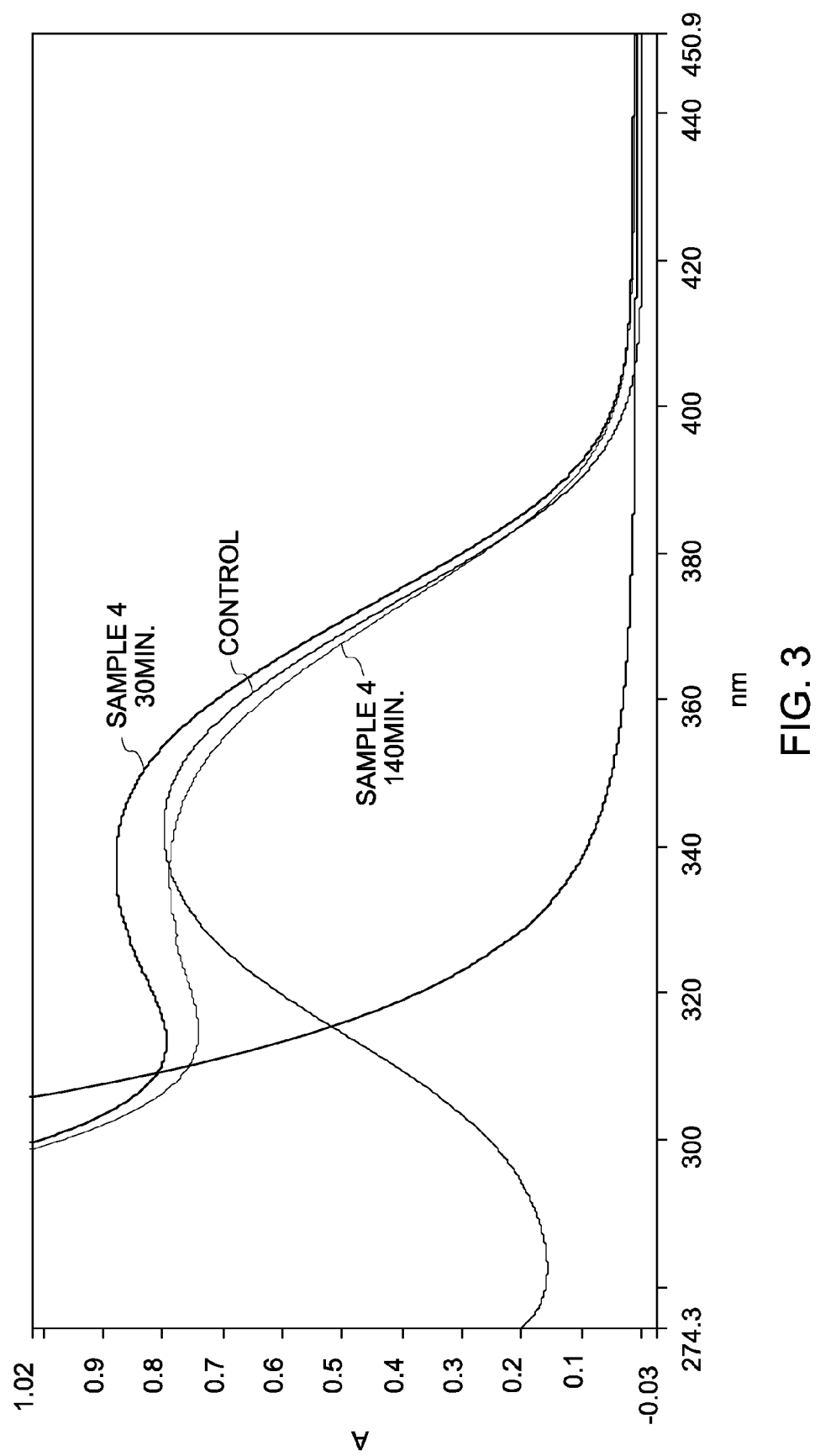
FIG. 3 shows the absorbance spectra of Sample 4 as a function of wavelength, after 30 minutes and 140 minutes.

Oxidation reaction of DAPI was monitored by measuring absorbance spectrum of Sample 4 as a function of time. FIG. 3 shows the absorbance spectra of Sample 4 as a function of wavelength, after duration of 30 minutes and 140 minutes. The absorbance value of Sample 4 did not vary much even after a period of 140 minutes and was in the same range as the control, exhibiting no significant effect of $H_2O_2$ on DAPI.

Example 2

Selective Oxidation (Using Sodium Periodate) of Cyanine Dyes without Affecting DAPI A solution of sodium periodate ($NaIO_4$) was prepared by mixing a 0.2 M solution of $NaIO_4$ in 0.1× phosphate buffer saline (PBS). Three separate solutions of cyanine dyes (Cy3, Cy5, and Cy7) were prepared in water at a concentration of about 2 µM. An aliquot of a cyanine dye solution was mixed with an aliquot of the $NaIO_4$ solution to prepare a solution with a final concentration of about 1 µM $NaIO_4$ and 1 µM cyanine dye (Samples 5 (Cy3), 6 (Cy5), and 7 (Cy7)). A 1 µM cyanine dye solution in water (without $NaIO_4$) was used as a control.

Figure 4:
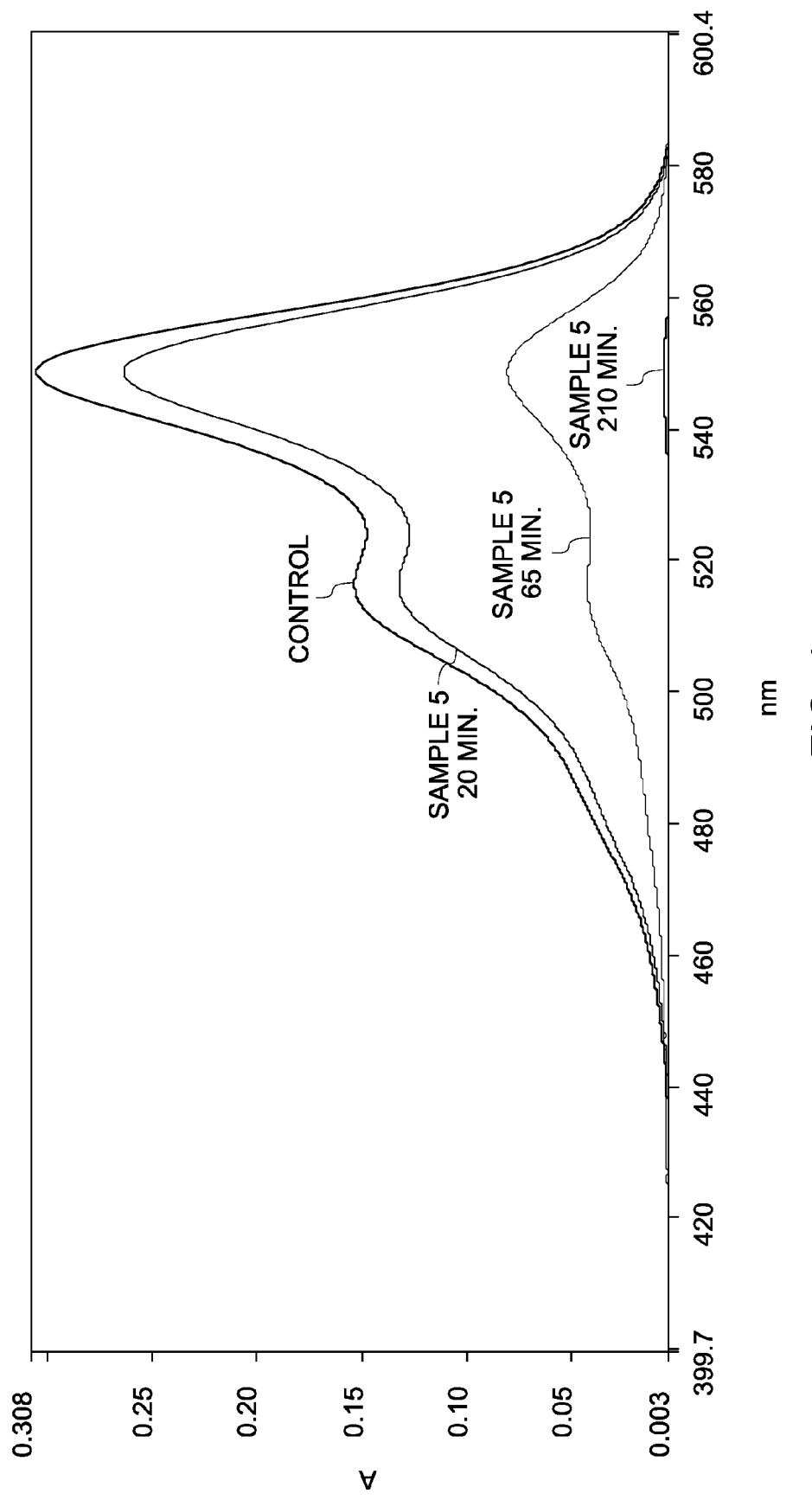
FIG. 4 shows the absorbance spectra of Sample 5 as a function of wavelength, after 20 minutes, 60 minutes, and 210 minutes.
Figure 5:
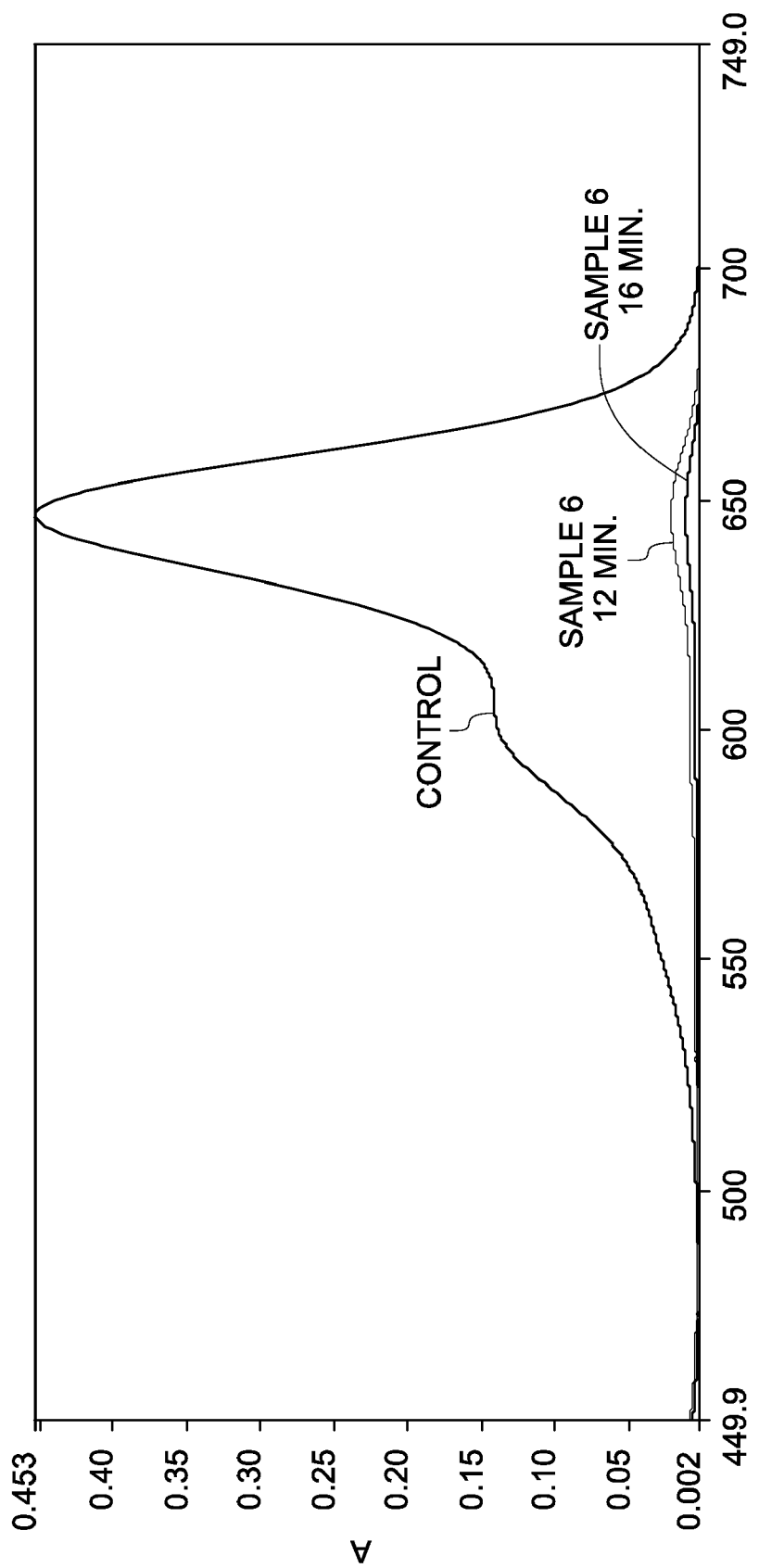
FIG. 5 shows the absorbance spectra of Sample 6 as a function of wavelength, after 12 minutes and 16 minutes.

Oxidation reaction of the cyanine dye was monitored by measuring absorbance spectrum of the dye on an ultraviolet/ visible (UV/Vis) spectrophotometer as a function of time. FIG. 4 shows the absorbance spectra of Sample 5 as a function of wavelength, after duration of 20 minutes, 60 minutes and 210 minutes. The absorbance value decreased as function of time when compared with the control. Complete absorbance loss was observed after 210 minutes for Sample 5. FIG. 5 shows the absorbance spectra of Sample 6 as a function of wavelength, after duration of 12 minutes and 16 minutes. The absorbance value decreased as function of time when compared with the control. Complete absorbance loss was observed rapidly, after 16 minutes.

A solution of 4',6-diamidino-2-phenylindole (DAPI) was prepared in water at a concentration of about 57 μM. An aliquot of DAPI solution was mixed with an aliquot of the $NaIO_4$ solution to prepare a solution with a final concentration of about 0.1 M $NaIO_4$ and 10 μg/mL DAPI (Sample 8). A 10 μg/mL DAPI solution in water (without $NaIO_4$) was used as a control.

Figure 6:
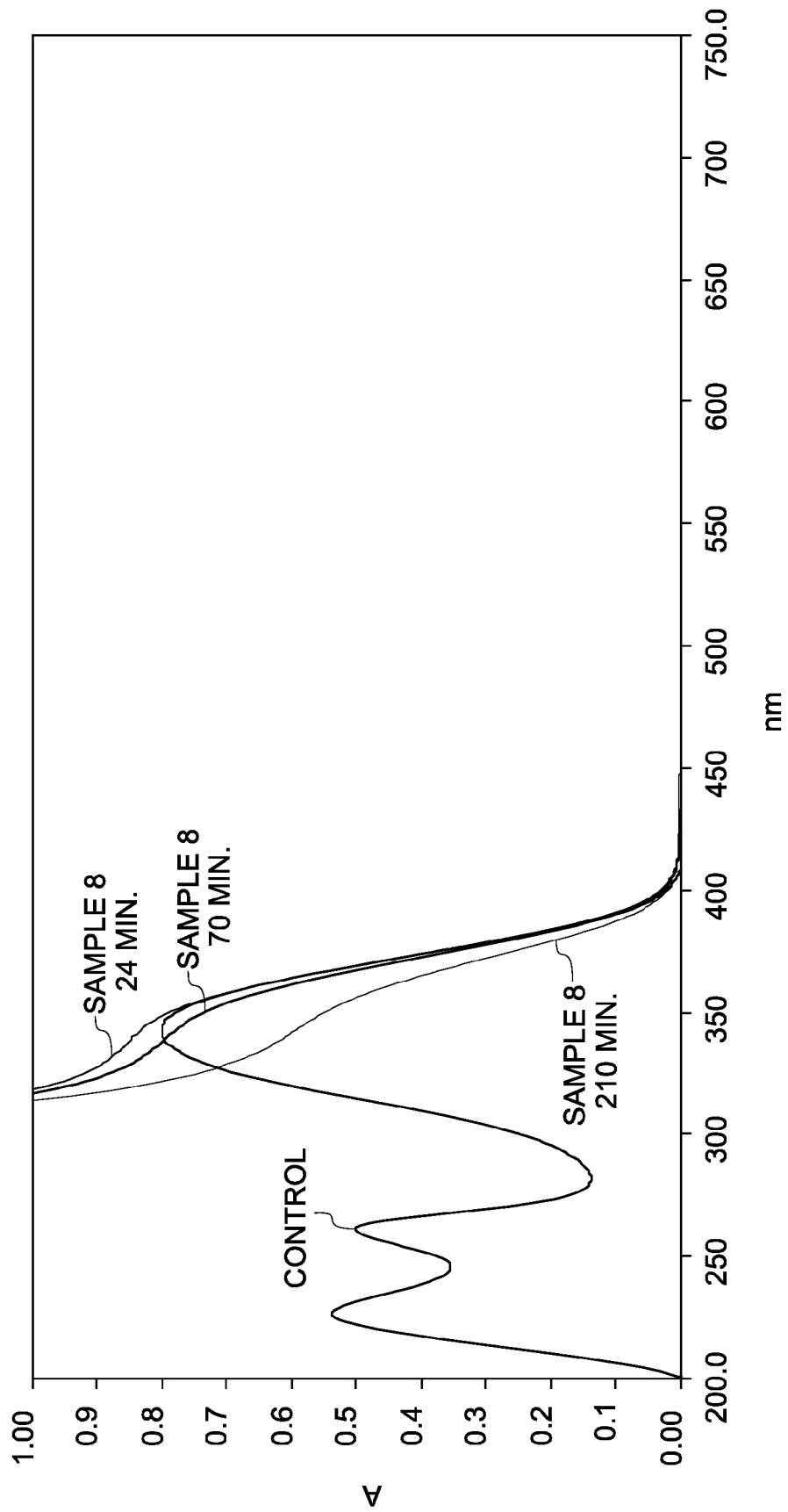
FIG. 6 shows the absorbance spectra of Sample 8 as a function of wavelength, after 22 minutes, 70 minutes, and 210 minutes.

Oxidation reaction of DAPI was monitored by measuring absorbance spectrum of Sample 8 as a function of time. FIG. 6 shows the absorbance spectra of Sample 8 as a function of wavelength, after duration of 22 minutes, 70 minutes and 210 minutes. The absorbance value of Sample 8 did not vary much even after a period of 210 minutes and a significant amount of DAPI remained intact when compared to the control.

Example 3

Selective Destruction (Using Sodium Hydroxide Base) of Cyanine Dyes Without Affecting DAPI A NaOH solution was prepared at a concentration of 0.1M and 1M. Three separate solutions of cyanine dyes, Cy3, Cy5, and Cy7 were prepared in water at a concentration of 2 μM. An aliquot of a cyanine dye solution was mixed with an aliquot of the NaOH solution of two different concentrations of NaOH: 0.1M NaOH (Samples 9a, 10a, and 11a) and 1M NaOH (Samples 9b, 10b, and 11b). A 1 μM cyanine dye solution in water (without NaOH) was used as a control.

Figure 7:
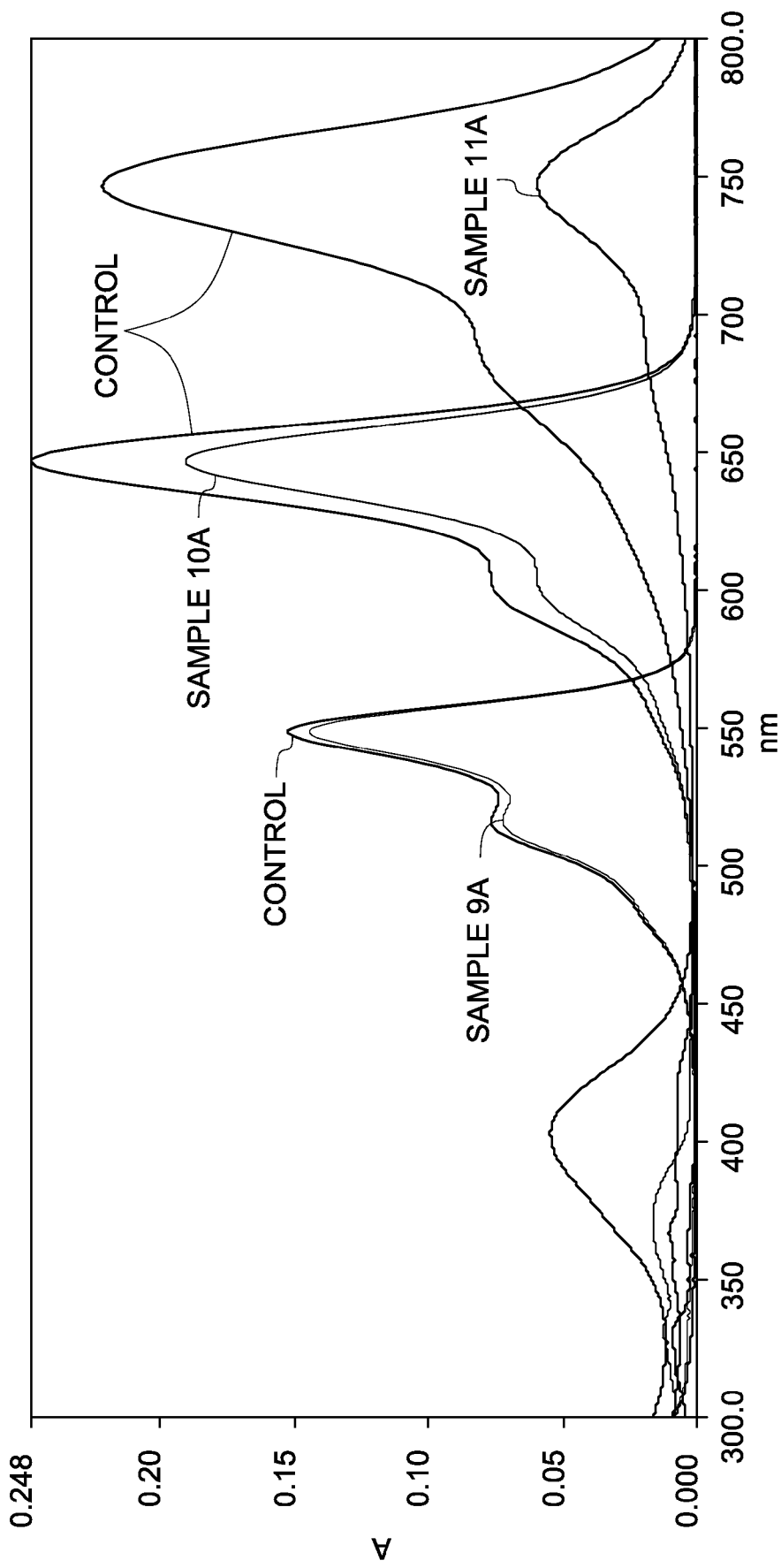
FIG. 7 shows the absorbance spectra of Samples 9a, 10a, and 11a as a function of wavelength.
Figure 8:
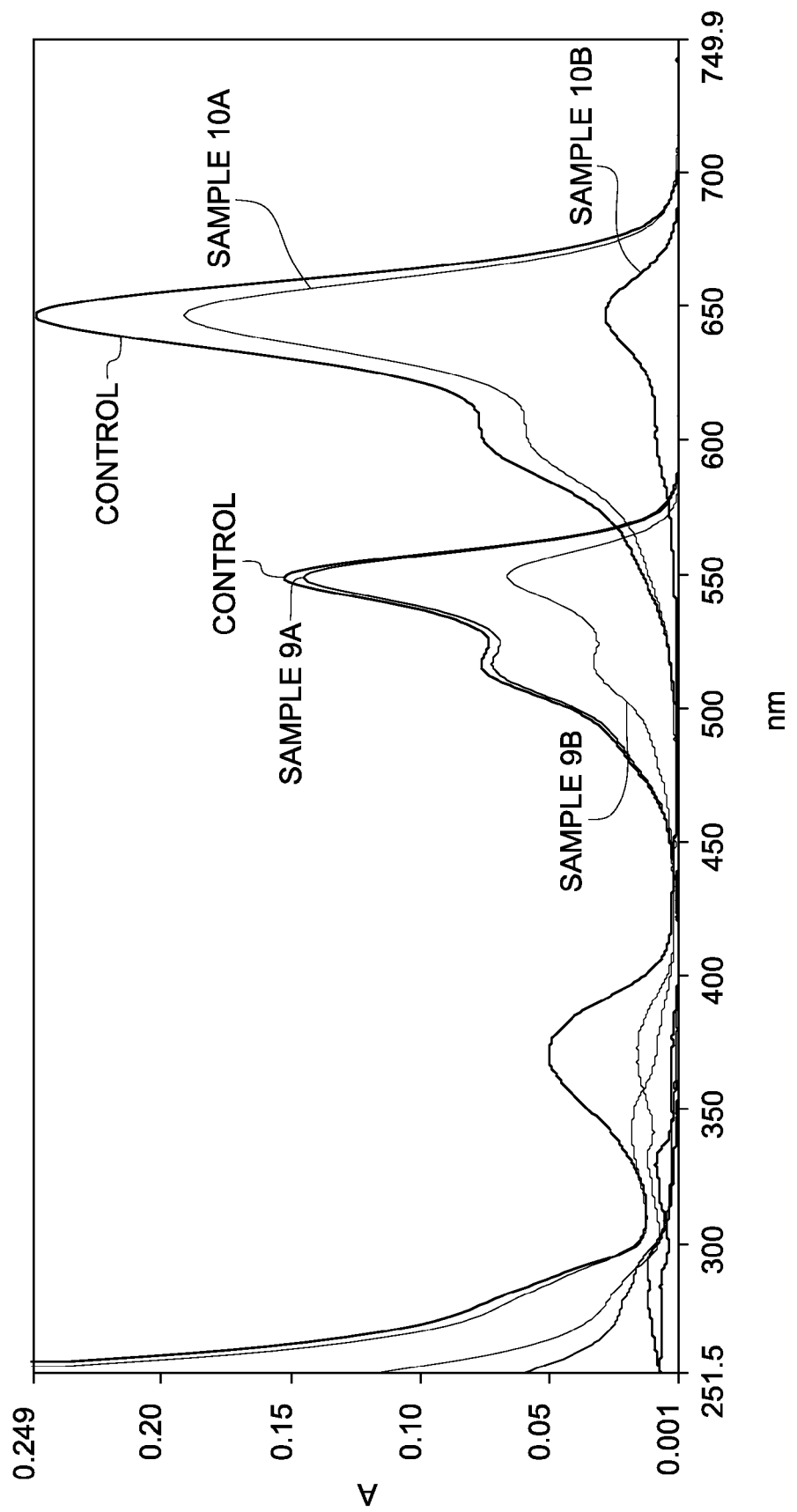
FIG. 8 shows the absorbance spectra of Samples 9b and 10b as a function of wavelength.

Base destruction of the dye was monitored by measuring absorbance spectrum of the samples as a function of time. FIG. 7 shows the absorbance spectra of Samples 9a, 10a, and 11a as a function of wavelength, after duration of less than 5 minutes. The absorbance value of Sample 9A did not vary much and a significant amount of Cy3 remained intact when compared to the control. Sample 10a showed a 20 percent decomposition of the Cy5 dye, while Sample 11A showed a 70 percent decomposition of the Cy7 dye using 0.1 M NaOH. FIG. 8 shows the absorbance spectra of Samples 9B and 10B as a function of wavelength, after duration of less than 5 minutes. Sample 9B showed a 50 percent decomposition of the Cy3 dye, while Sample 10B showed an 80 percent decomposition of the Cy5 dye using 1 M NaOH.

Figure 9:
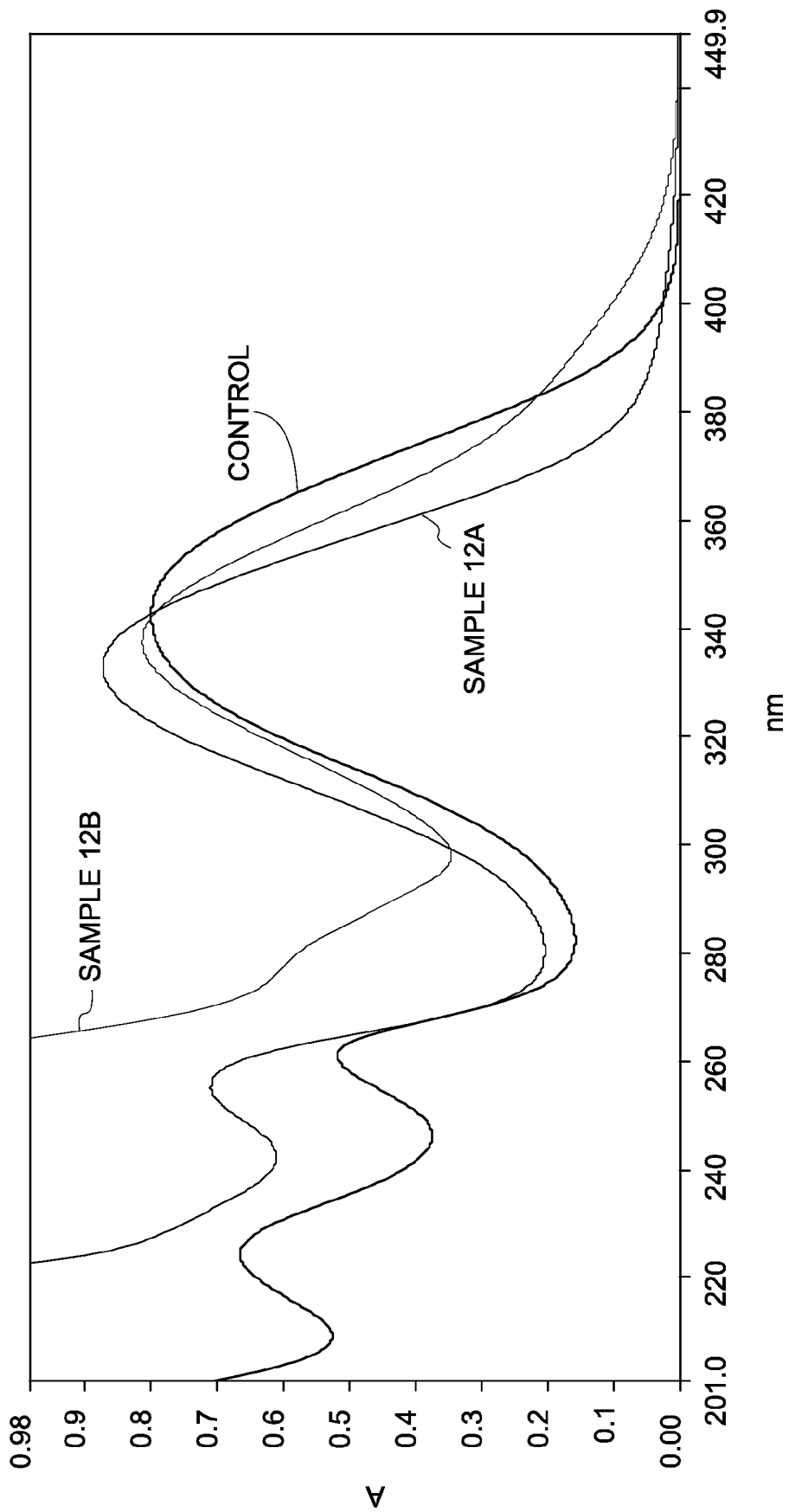
FIG. 9 shows the absorbance spectra of Samples 12a and 12b as a function of wavelength.

A solution of 4',6-diamidino-2-phenylindole (DAPI) was prepared in water at a concentration of about 57 μM. An aliquot of DAPI solution was mixed with an aliquot of the NaOH solution of two different concentrations 0.1M NaOH (Samples 12A) and 1M NaOH (Samples 12B). A 10 μg/mL DAPI dye solution in water (without NaOH) was used as a control. Base destruction of DAPI was monitored by measuring absorbance spectrum of Samples 12A and 12B as a function of time. FIG. 9 shows the absorbance spectra of Samples 12A and 12B as a function of wavelength. The absorbance value of the samples did not vary much and a significant amount of DAPI remained intact when compared to the control.

Example 4

Selective Destruction of Cy5 and Cy7 Dyes without Affecting Cy3

A 5 percent (w/v) solution of a nucleophile was prepared by mixing tris[2-carboxyethyl]-phosphine hydrochloride (TCEP.HCl) in 1M-sodium bicarbonate buffer (final pH 7.7). Three separate solutions of cyanine dyes, Cy3, Cy5, and Cy7 were prepared in water at a concentration of about 2 μM. An aliquot of a cyanine dye solution was mixed with an aliquot of the TCEP.HCl solution to prepare Samples 13 (Cy3), 14 (Cy5), and 15 (Cy7). A 1 μM cyanine dye solution in water (without TCEP.HCl) was used as a control.

Figure 10:
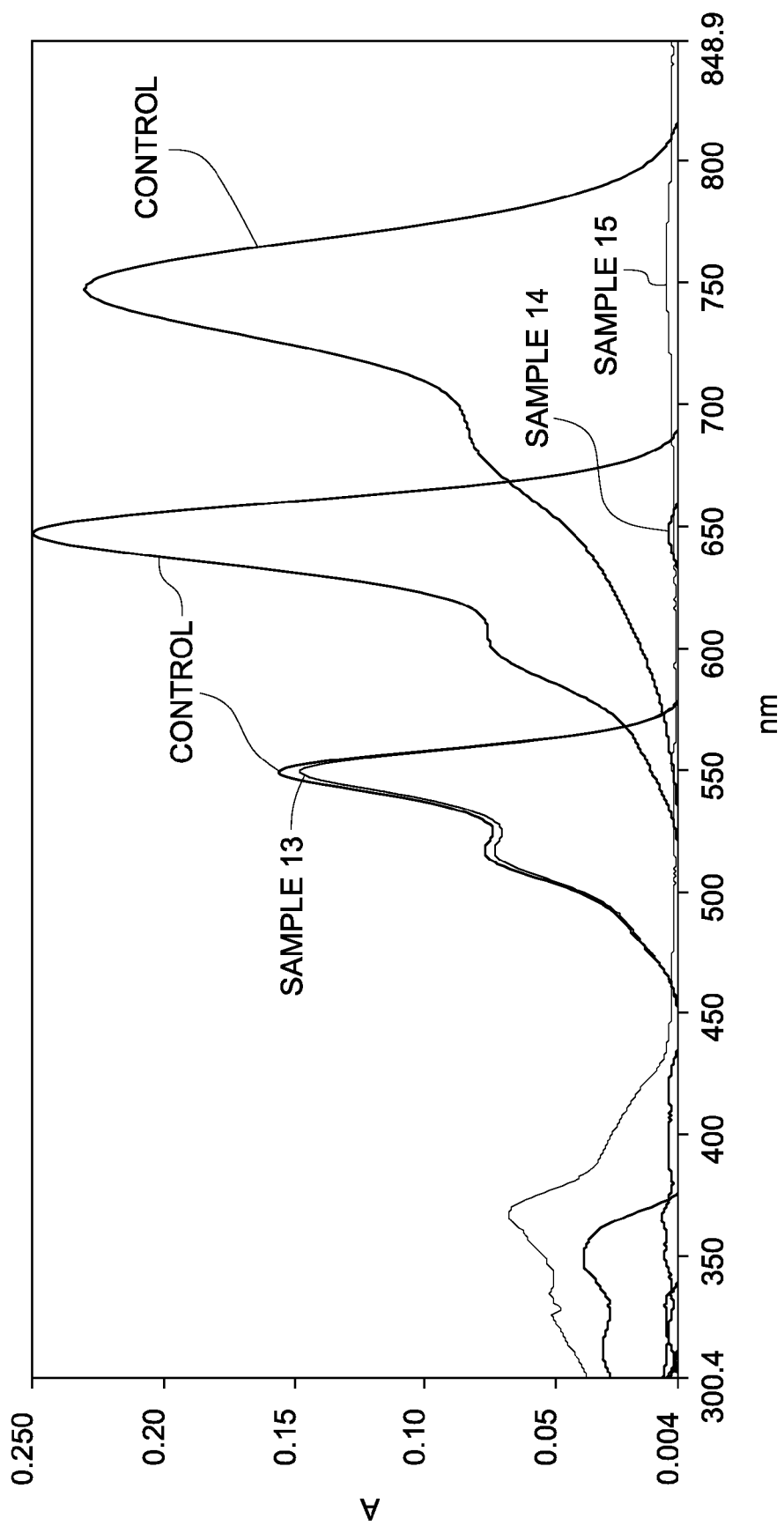
FIG. 10 shows the absorbance spectra of Samples 13, 14, and 15 as a function of wavelength.

Destruction of the dye was monitored by measuring absorbance spectrum of the samples as a function of time. FIG. 10 shows the absorbance spectra of Samples 13, 14, and 15 as a function of wavelength. The absorbance value of Sample 13 did not vary much and a significant amount of Cy3 remained intact when compared to the control after duration of 60 minutes. Samples 14 and 15 showed a significant decomposition of the Cy5 and Cy7 dyes after duration of 0.5 minutes.

Example 5

Selective Destruction of Cy7 Dye without Affecting Cy3

A solution of hydrogen peroxide ($H_2O_2$) was prepared in a phosphate buffer saline solution (PBS) by mixing a 6% (v/v) solution of $H_2O_2$ in 0.8×PBS (final pH 6.6). Two separate solutions of cyanine dyes, Cy3 and Cy7 were prepared in water at a concentration of about 2 μM. An aliquot of a cyanine dye solution was mixed with an aliquot of the $H_2O_2$ solution to prepare Samples 16 (Cy3) and 17 (Cy7)). A 1 μM cyanine dye solution in water (without $H_2O_2$) was used as a control.

Figure 11:
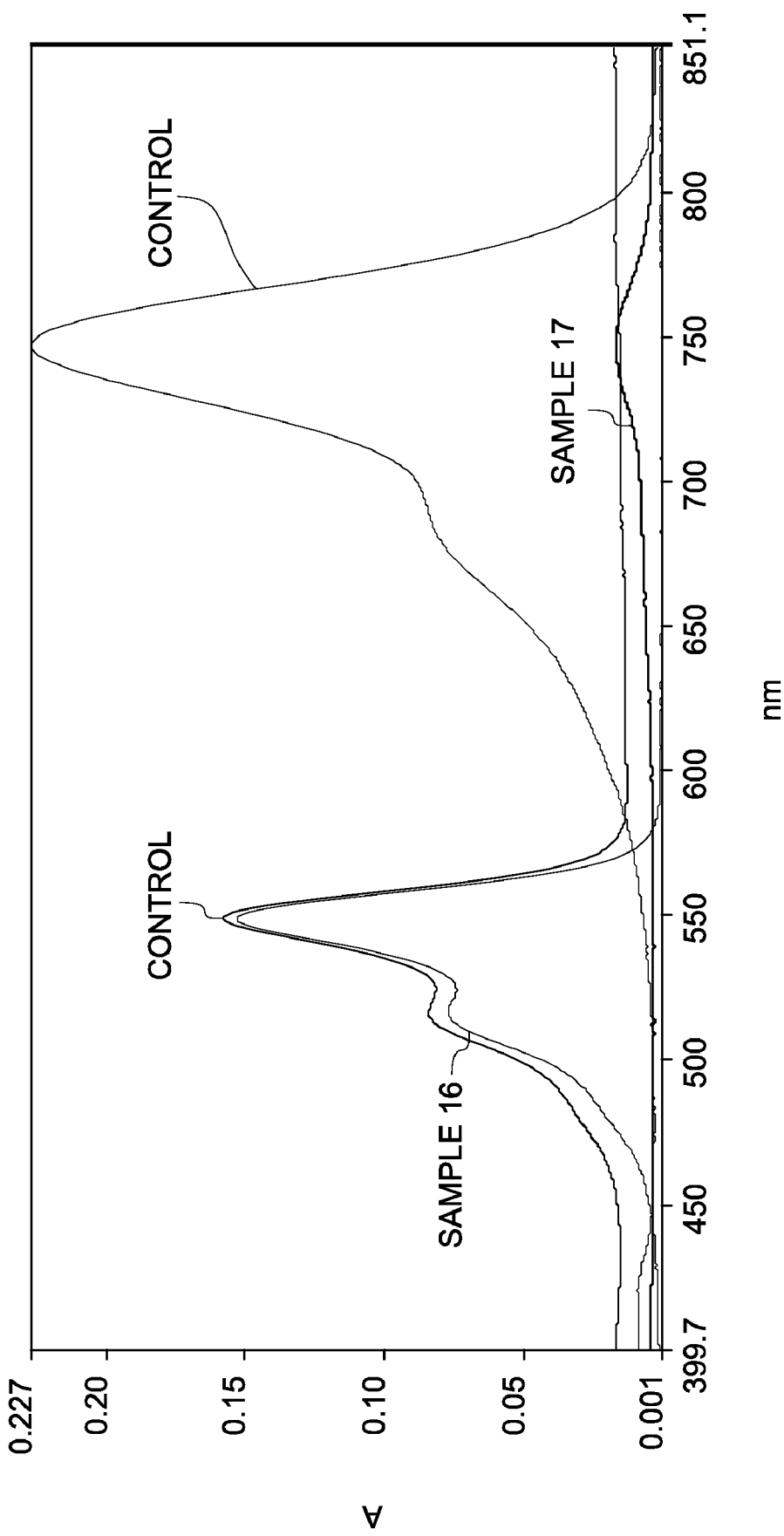
FIG. 11 shows the absorbance spectra of Samples 16 and 17 as a function of wavelength.

Destruction of the dye was monitored by measuring absorbance spectrum of the samples as a function of time. FIG. 11 shows the absorbance spectra of Samples 16 and 17 as a function of wavelength. The absorbance value of Sample 16 did not vary much and a significant amount of Cy3 remained intact when compared to the control after duration of 60 minutes. Sample 17 showed a significant decomposition of the Cy7 dye after duration of 60 minutes.

The following examples 6-21 illustrate embodiments of the invention according to which multiple imaging of tissue samples is conducted. Multiple staining is obtained by staining, imaging, chemically destroying the fluorophore, restaining, imaging, and repeating the steps Example 6

Preparation of Tissue Samples for Staining

Adult human tissue samples were obtained as tissue slides embedded in paraffin. The tissue samples included slides of colon (Biochain, T2234090), normal breast tissue (Biochain, T2234086), prostate cancer (Biochain, T2235201-1), colon adenocarcinoma (Biochain, T2235090-1), breast tissue microarray (Imgenex, IMH 367, p61), breast TMA (Imegenex IMH 367, p32), and normal prostate (Biochain, T2234201). Paraffin embedded slides of adult human tissue were subjected to an immunohistochemistry protocol to prepare them for staining. The protocol included deparaffinization, rehydration, incubation, and wash. Deparaffinization was carried by washing the slides with Histochoice (or toluene) for a period of 10 minutes and with frequent agitation. After deparaffinization, the tissue sample was rehydrated by washing the slide with ethanol solution. Washing was carried out with three different solutions of ethanol with decreasing concentrations. The concentrations of ethanol used were 90 volume %, 70 volume %, and 50 volume %. The slide was then washed with a phosphate buffer saline (PBS, pH 7.4). Membrane permeabilization of the tissue was carried out by washing the slide with 0.1 weight percent solution of Triton TX-100. Citrate buffer pH 6.0 (Vector Unmasking Solution) was used for antigen retrieval. The slides were exposed to the buffer in a pressure cooker for a period of 15 minutes followed by cooling at room temperature for 20 minutes. The slide was then blocked against nonspecific binding by washing with PBS and 900 μL of 3 volume percent bovine serum albumin (BSA) for 45 minutes at 37 C. For staining with secondary antibodies (optional), the slide was also blocked with 100 μL of serum from secondary antibody host species.

Example 7

Conjugation of Antibodies with a Dye

Dye-conjugated antibodies were prepared according to the following procedure. The antibodies used for conjugating and staining included anti-proliferating cell nuclear antigen, clone pc10 (Sigma Aldrich, P8825); anti-smooth muscle alpha actin (SmA), clone 1A4 (Sigma, A2547); rabbit anti-beta catenin (Sigma, C 2206); mouse anti-pan cytokeratin, clone PCK-26 (Sigma, C1801); mouse anti-estrogen receptor alpha, clone 1D5 (DAKO, M 7047); beta catenin antibody, clone 15B8 (Sigma, C 7738); goat anti-vimentin (Sigma, V4630); cycle androgen receptor clone AR441 (DAKO, M3562); Von Willebrand Factor VII, keratin 5, keratin 8/18, e-cadherin, Her2/neu, Estrogen receptor, p53, progesterone receptor, beta catenin; donkey anti-mouse (Jackson Immunoresearch, 715-166-150); and donkey anti-rabbit (Jackson Immunoresearch, 711-166-152).

A micron YM-10 spin column was wetted with 250 mL of PBS and the column was spun for 15 minutes. 500 mL of the antibody (200 μg/mL) was pipetted into the wet column. The column was spun for 30 minutes at 11000 rpm at 4 C. The concentrated antibody/protein was then transferred into a new tube and spun for 30 seconds to remove the concentrated protein. A coupling buffer solution was then mixed with the concentrated antibody solution. The coupling buffer solution included 1M sodium carbonate (pH between 8-9) and 5 μL of the buffer was used per 100 μL of the antibody solution. The antibody and buffer solution was added to 0.01-0.1 milligrams of the cyanine dye. The dye was reconstituted in DMSO to a 10-20-mg/mL concentration prior to incubating with the antibody. The resulting solution was mixed thoroughly by pipetting and any bubbles formed were removed by spinning the tube. The solution was covered with a foil and incubated at room temperature for a period of about 30-45 minutes. Post incubation the solution was added to YM-10 spin column and spun for 30 minutes at 4 C at 11000 rpm. The solution was washed with PBS and spun to remove any unconjugated dye or antibody. The dye-conjugated antibody solution was then diluted with 50 percent glycerol and stored in a freezer at −20 C.

Example 8

Staining and Imaging of Tissue with Dyes

A slide prepared in Example 6 was incubated with a dye-conjugated antibody prepared in Example 7. Incubation was conducted in 3 percent BSA for 45 minutes at 37 C. After incubation, the slide was subjected to an extensive series of PBS washes. When secondary antibodies were used, the slide was incubated with a secondary antibody in BSA for 45 minutes at 37 C. After incubation, the slide was subjected to an extensive series of PBS washes. A primary antibody or secondary antibody-stained slide was counterstained with the morphological stain, DAPI, and cover slipped.

A cover slipped slide was imaged using a camera. The camera used was a monochromatic Leica DFC 350FX monochromatic high-resolution camera mounted in a Leica DMRA2 fluorescent microscope. The magnification used was 20× unless otherwise stated. After image acquisition, the cover slip was removed and the slide was washed with PBS to prepare for signal destruction.

Example 9

Dye Destruction, Staining, and Imaging

NaOH solution and $H_2O_2$ solution were used for signal destruction. A NaOH solution was prepared using 500 μL of 50 volume percent NaOH and 49.5 mL of PBS. The final pH of the NaOH solution was around 11.9-12.5. A $H_2O_2$ solution was prepared by mixing 10 mL of 0.5M sodium carbonate (pH 10), 5 mL of 30 volume percent $H_2O_2$, and 35 mL of water. A slide was placed in the NaOH or $H_2O_2$ solution for 15 minutes with gentle agitation. After 15 minutes, the slide was washed again with PBS, cover slipped and either imaged again (optional) to check the efficacy of the dye destruction or restained and imaged. Restaining and reimaging steps were carried out using the process described in Example 8. Following imaging, a slide was subjected to signal destruction, staining, and imaging cycles, and the process was repeated a multiple number of times. The tissue samples were imaged using 1-9 different antibodies. After imaging with the cyanine series, the slide was optionally stained and imaged with morphological stains H&E.

Example 10

Figure 12:
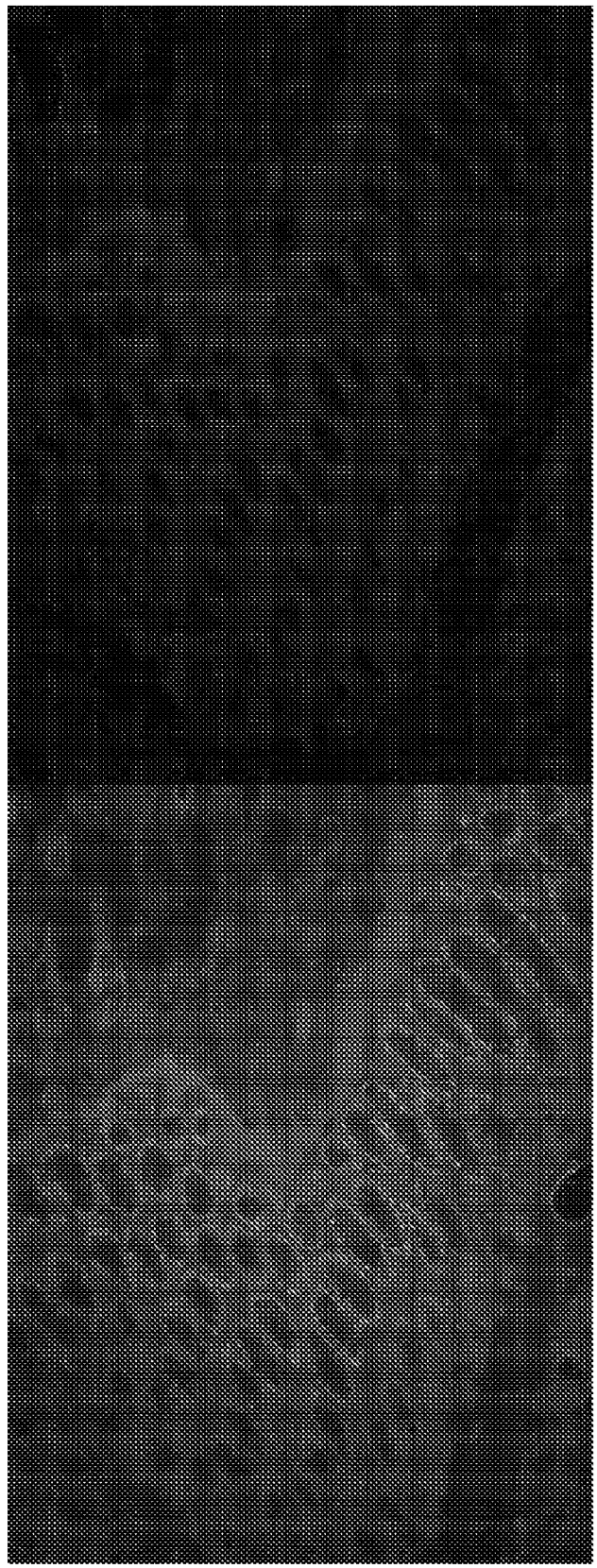
FIG. 12 shows the micrographs (at 10× magnification) of Sample 18A (before signal modification) and Sample 18B (after signal modification).

Single Channel Staining and Imaging of a Normal Colon Tissue Followed by Signal Destruction Using NaOH A normal colon slide was stained with a primary antibody mouse anti-proliferating cell nuclear antigen (PCNA) clone pc 10, and detected with a Cy3-conjugated donkey anti-mouse to form Sample 18A. Sample 18A was imaged and then treated with a NaOH solution to form Sample 18B, which was imaged again. Staining, imaging, and dye destruction steps were performed according to the procedures described herein in Examples 8 and 9. FIG. 12 shows micrographs (at 10× magnification) of Sample 18A (before dye destruction) and Sample 18B (after dye destruction). After treatment with NaOH little or no signal from Cy3 remained.

Example 11

Figure 13:
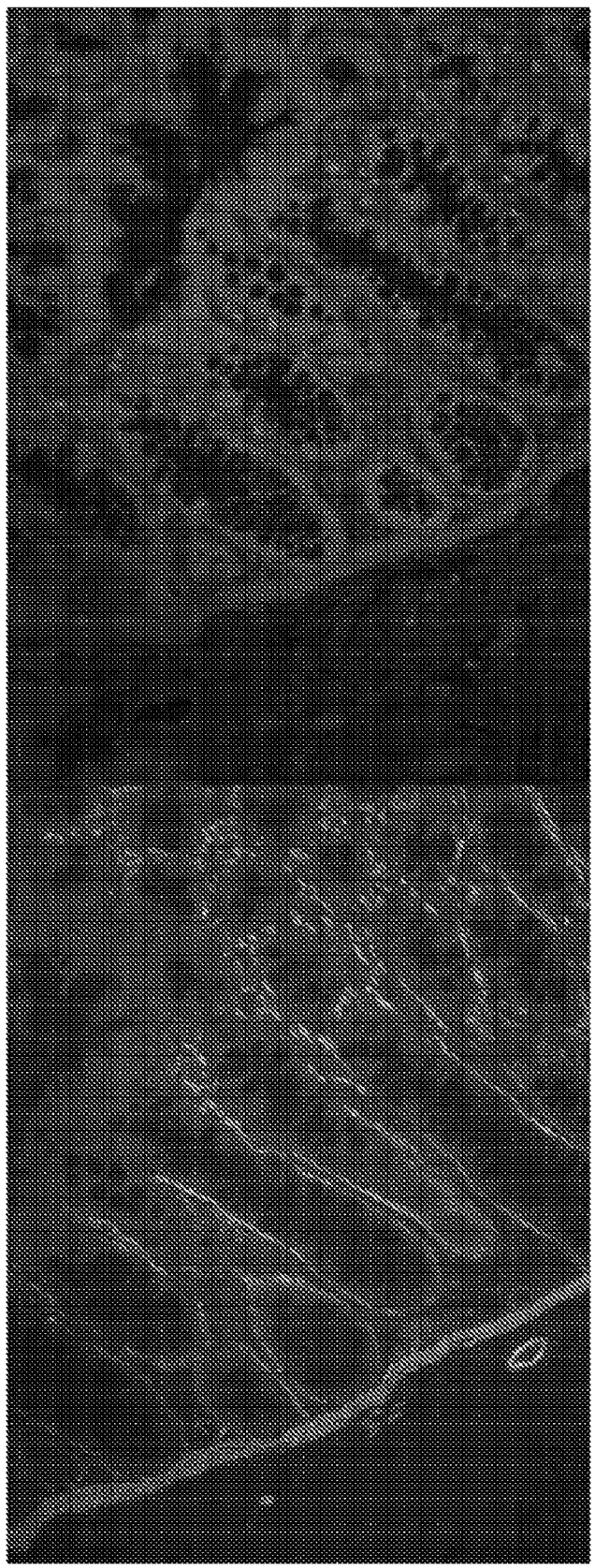
FIG. 13 shows the micrographs (at 10× magnification) of Sample 19A (before signal modification) and Sample 19B (after signal modification).

Single Channel Staining and Imaging of a Normal Colon Tissue Followed by Signal Destruction Using NaOH A normal colon slide was stained with a primary antibody mouse anti-smooth muscle alpha actin (SmA) clone 1A4, and detected with a Cy3-conjugated donkey anti-mouse to form Sample 19A. Sample 19A was imaged and then treated with a NaOH solution to form Sample 19B, which was imaged again. Staining, imaging, and dye destruction steps were performed according to the procedures described herein in Examples 8 and 9. FIG. 13 shows micrographs (at 10× magnification) of Sample 19A (before dye destruction) and Sample 19b (after dye destruction). After treatment with NaOH a little amount of signal from Cy3 remained.

Example 12

Two Channel Staining and Imaging of a Normal Breast Tissue Using NaOH

A normal breast tissue was stained with a primary antibody SmA, detected with a Cy3-conjugated donkey anti-mouse, and counter-stained with DAPI to form Sample 20A. Sample 20a was imaged and then treated with a NaOH solution to form Sample 20B, which was imaged again. Staining, imaging, and dye destruction steps were performed according to the procedures described herein in Examples 8 and 9. Sample 20B was restained with a primary antibody rabbit anti-beta catenin, and detected with a Cy3-conjugated anti-rabbit to form Sample 20C. Sample 20C was imaged and then counter-stained with H&E to form Sample 20D and imaged again.

Figure 14:
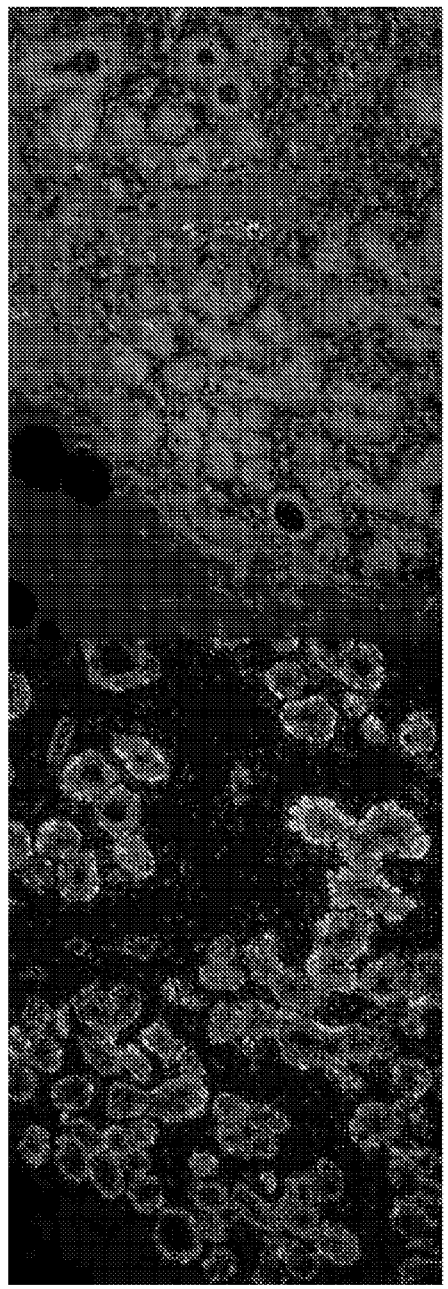
FIG. 14 shows the micrographs of Sample 20A (before signal modification) and Sample 20B (after signal modification).
Figure 14:
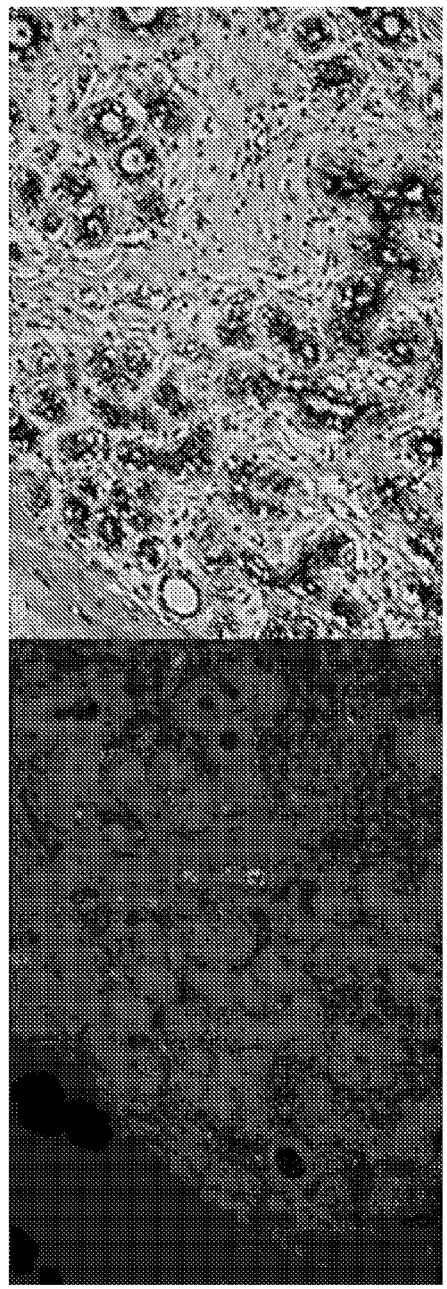

FIG. 14 shows micrographs of Sample 20A (before dye destruction) and Sample 20B (after dye destruction). After treatment with NaOH little or no signal from Cy3 remained and only DAPI was observed. Micrograph of Sample 20c showed imaging in the same Cy3 channel was possible by staining with a different antibody. Morphological information about the tissue was obtained by further staining with H&E (Sample 20D).

Example 13

Two Channel Staining and Imaging of a Prostrate Cancer Tissue Using NaOH

A prostrate cancer tissue was stained with a primary antibody mouse anti-pan cytokeratin clone PCK-26, and detected with a Cy3-conjugated donkey anti-mouse, to form Sample 21A. Sample 21A was imaged and then counterstained with DAPI to form Sample 21B. Sample 21B was imaged and then treated with a NaOH solution to form Sample 21C, which was imaged again. Staining, imaging, and dye destruction steps were performed according to the procedures described herein in Examples 8 and 9. Sample 21C was restained with a primary antibody SmA, and detected with a Cy3-conjugated anti-rabbit to form Sample 21D and imaged again.

Figure 15:
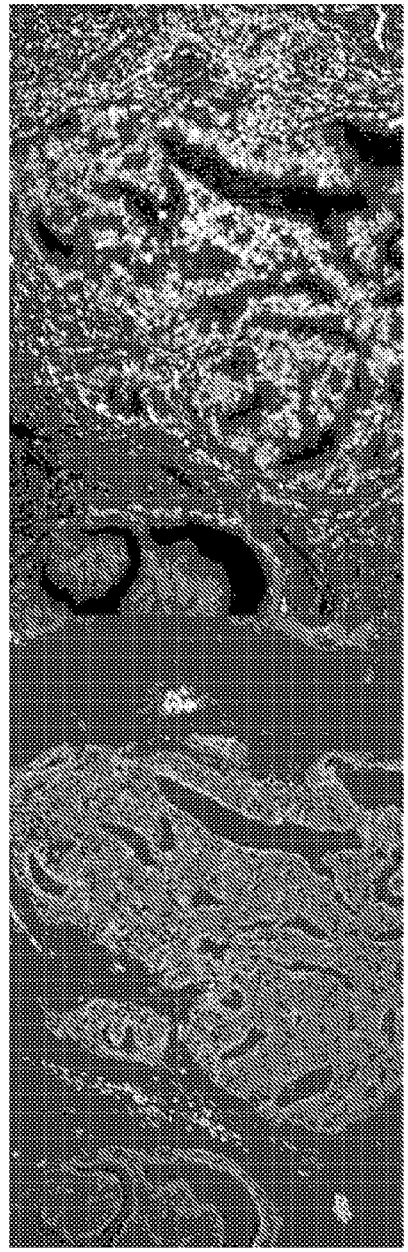
FIG. 15 shows the micrographs of Samples 21A and 21B (before signal modification) and Sample 21C (after signal modification).
Figure 15:
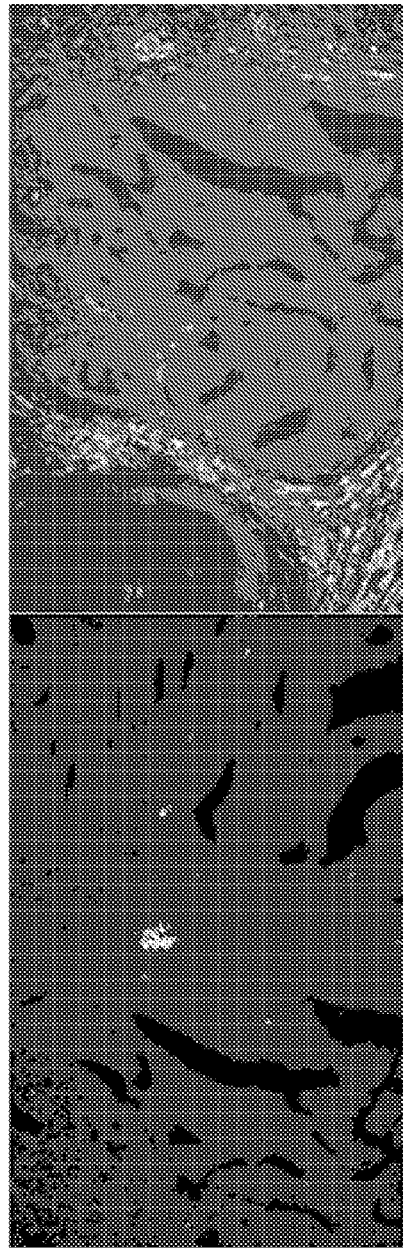

FIG. 15 shows micrographs of Sample 21A (Cye channel) and Sample 21B (DAPI channel) before dye destruction and Sample 21C (Cye channel) after dye destruction. After treatment with NaOH little or no signal from Cy3 remained (21C) and only DAPI was observed (not shown). Micrograph of Sample 21D showed imaging in the same Cy3 channel was possible by staining with a different antibody.

Example 14

Two Channel Staining and Imaging of a Colon Adenocarcinoma Using NaOH

A colon adenocarcinoma slide was stained with a primary antibody mouse anti-anti-pan cytokeratin clone PCK-26, and detected with a Cy3-conjugated donkey anti-mouse, to form Sample 22A. Sample 22A was imaged and then counter-stained with DAPI to form Sample 22B. Sample 22B was imaged and then treated with a NaOH solution to form Sample 22C, which was imaged again. Staining, imaging, and dye destruction steps were performed according to the procedures described herein in Examples 8 and 9. Sample 22C was restained with a primary antibody SmA, and detected with a Cy3-conjugated anti-rabbit to form Sample 22d and imaged again.

Figure 16:
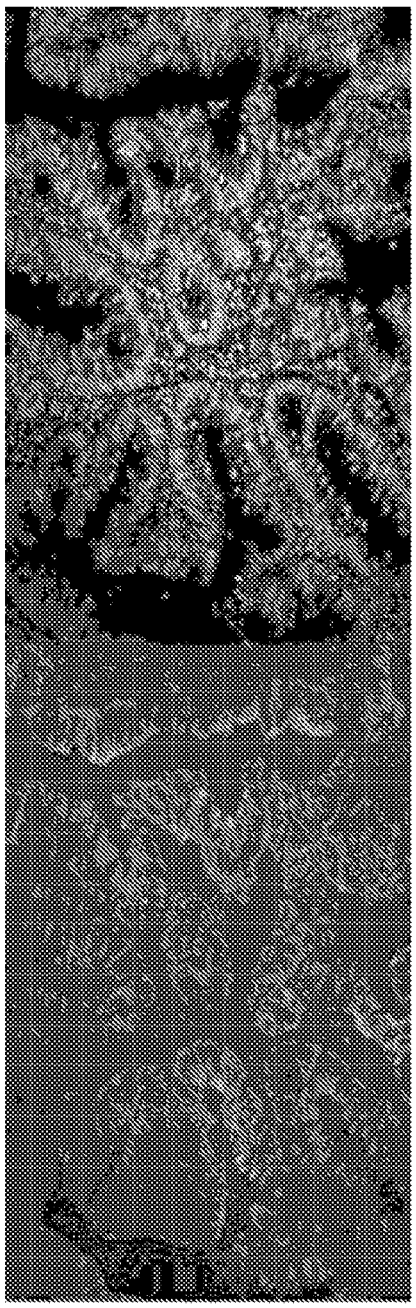
FIG. 16 shows the micrographs of Samples 22A and 22B (before signal modification) and Sample 22C (after signal modification).
Figure 16:
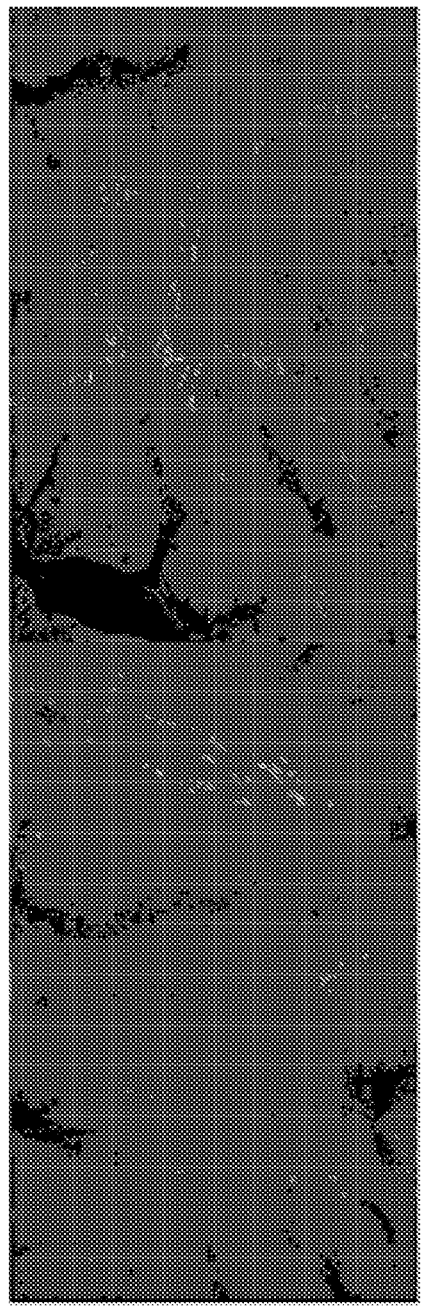

FIG. 16 shows micrographs of Samples 22A (Cye channel) and 22B (DAPI channel) before dye destruction) and Sample 22c after dye destruction. After treatment with NaOH little or no signal from Cy3 remained (22D) and only DAPI was observed (not shown). Micrograph of Sample 22D showed imaging in the same Cy3 channel was possible by staining with a different antibody. Nuclear information about the tissue was obtained by staining with DAPI (Sample 22B).

Example 15

Two Channel Staining and Imaging of a Breast Tissue Microarray with Baseline Measurement Using NaOH A breast tissue microarray (Sample 23A) was imaged in the DAPI and Cy3 channel to measure the autofluorescence from the tissue. Sample 23A was then stained with DAPI to form Sample 23B, imaged and then treated with NaOH to form Sample 23C, and imaged again. Sample 23A was also stained with a primary antibody mouse anti-estrogen receptor alpha clone 1D5, and detected with a Cy3-conjugated donkey anti-mouse, to form Sample 23D. Sample 23D was imaged then treated with a NaOH solution to form Sample 23E, which was imaged again. Staining, imaging, and dye destruction steps were performed according to the procedures described herein in Examples 8 and 9.

Figure 17:
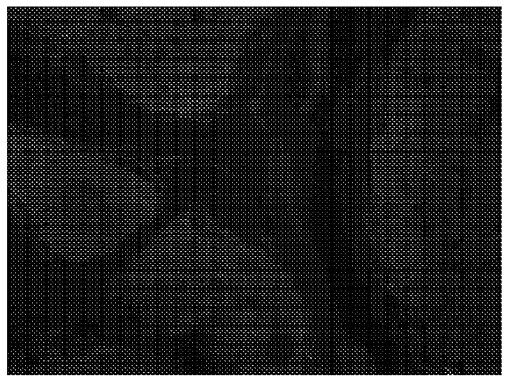
FIG. 17 shows the micrographs of Samples 23A-E.
Figure 17:
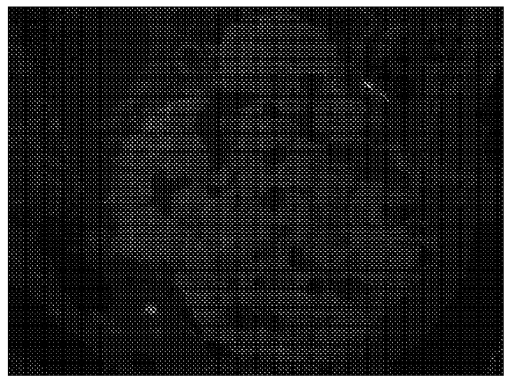
Figure 17:
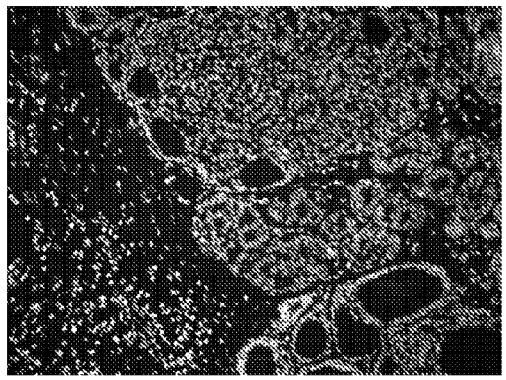
Figure 17:
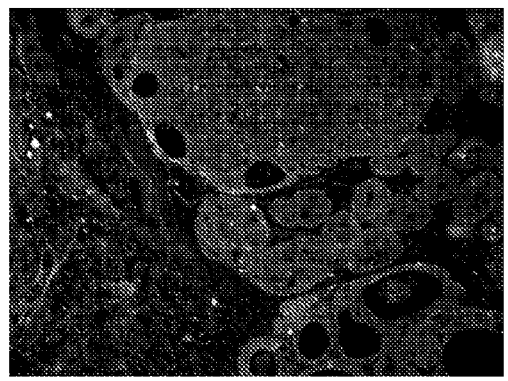
Figure 17:
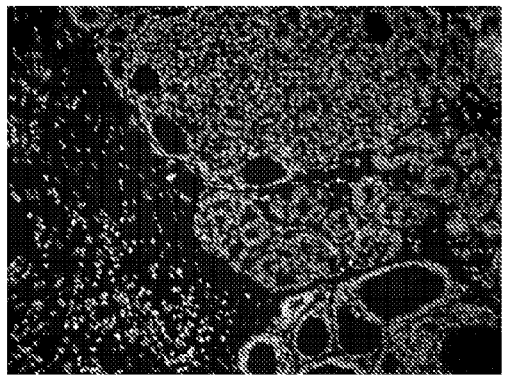
Figure 17:

FIG. 17 shows micrographs of Samples 23A-E. Micrographs of Samples 23C and 23E were compared to the autofluorescence (baseline) observed in Sample 23A. Both Samples showed signal reduction. DAPI-stained sample showed signal reduction possibly due to destruction of nucleic acids to which DAPI binds.

Example 16

Three Channel Staining and Imaging of Breast TMA Using NaOH

Figure 18:
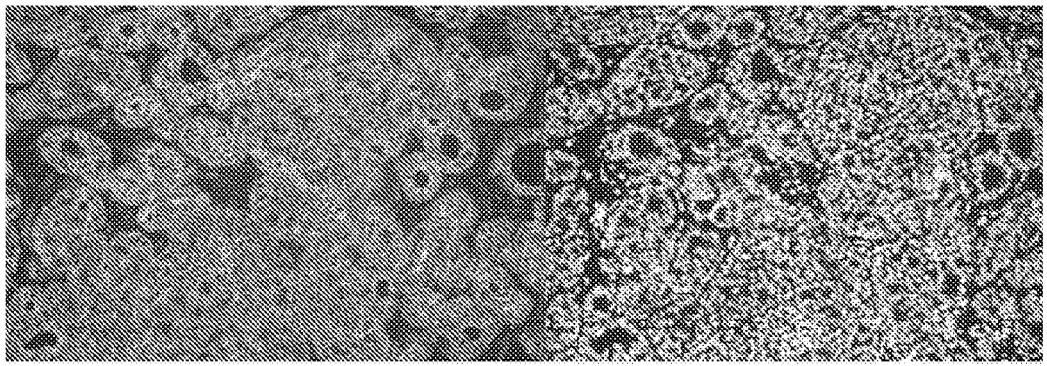
FIG. 18 shows the micrographs of Sample 24A (before signal modification) and Sample 24b (after signal modification).
Figure 18:
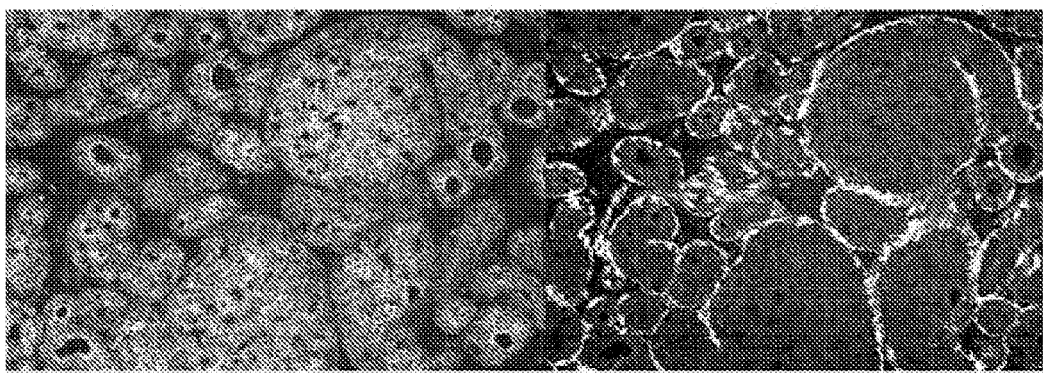
Figure 18:
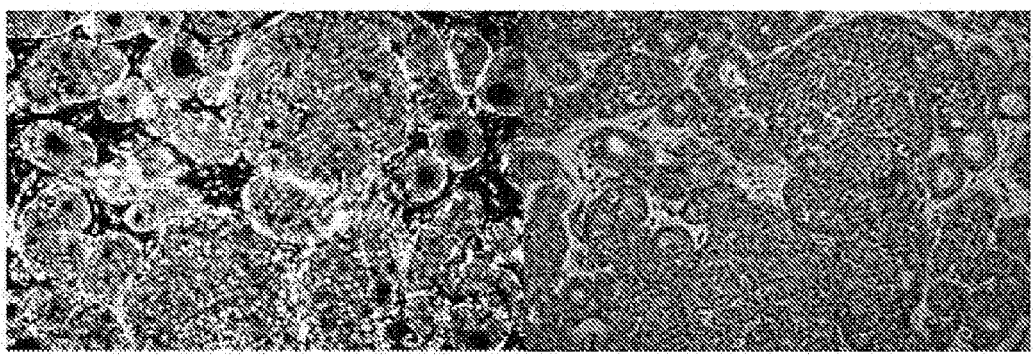

A breast sample was stained with a primary antibody mouse anti-pan cytokeratin clone PCK-26, detected visualized with a Cy3-conjugated donkey anti-mouse to form Sample 24A, and counterstained with DAPI (not shown) and imaged. Sample 24A was then treated with a NaOH solution to remove Cy3 signal (not shown), while retaining DAPI signal to form Sample 24B and imaged as shown in FIG. 18 at Sample 24B Staining, imaging, and dye destruction steps were performed according to the procedures described herein in Examples 8 and 9. Sample 24B was restained with a Cy3-directly conjugated beta catenin antibody to form Sample 24C and imaged again. The sample was again treated with NaOH and labeled with Cy3-direct conjugated SmA antibody to form Sample 24D and imaged again. The images obtained were registered, pseudo colored and overlaid (Sample 24E) to give spatial information for expressing antigen. Sample 24D was further stained with H&E to form Sample 24F.

FIG. 18 shows micrographs of Sample 24A (Cy3 channel before dye destruction) and Sample 24B (DAPI channel after dye destruction). After treatment with NaOH little or no signal from Cy3 remained and only DAPI was observed. Micrographs of Samples 24C and 24D showed imaging in the same Cy3 channel was possible by staining with different antibodies. Morphological information about the tissue was obtained by staining with H&E (Sample 24F).

Example 17

Twelve Channel Staining and Imaging of Normal Prostrate Using NaOH

Images were taken prior to staining to baseline the autofluorescence coming from each channel. A normal prostrate slide was stained with a cocktail of two primary antibodies: goat anti-vimentin and mouse anti-pan cytokeratin. The two primary antibodies were detected with a second cocktail of secondary antibodies: Cy3-conjugated donkey anti-goat and Cy5-conjugated donkey anti-mouse to form Sample 25A Cy3 and Cy5 respectively. Sample 25A was imaged and then treated with a NaOH solution. The tissue was then sequentially stained with a two primary antibodies: rabbit anti-alpha catenin, which was subsequently detected with Cy3 conjugated secondary antibody, and then Cy5 conjugated anti-androgen receptor, to form Samples 25B (25b-Cy3 and 25b-Cy5 respectively). Following imaging, the sample was treated with a NaOH solution followed by staining-imaging-NaOH treatment-staining steps using seven Cy-directly conjugated antibodies (Samples 25C-25I). The antibodies used were: smooth muscle alpha actin, beta catenin, pan cadherin, Von Willebrand Factor VII, keratin 5, keratin 8/18, and e-cadherin. Each staining step included counterstaining with DAPI (Sample 25J).

Figure 19:
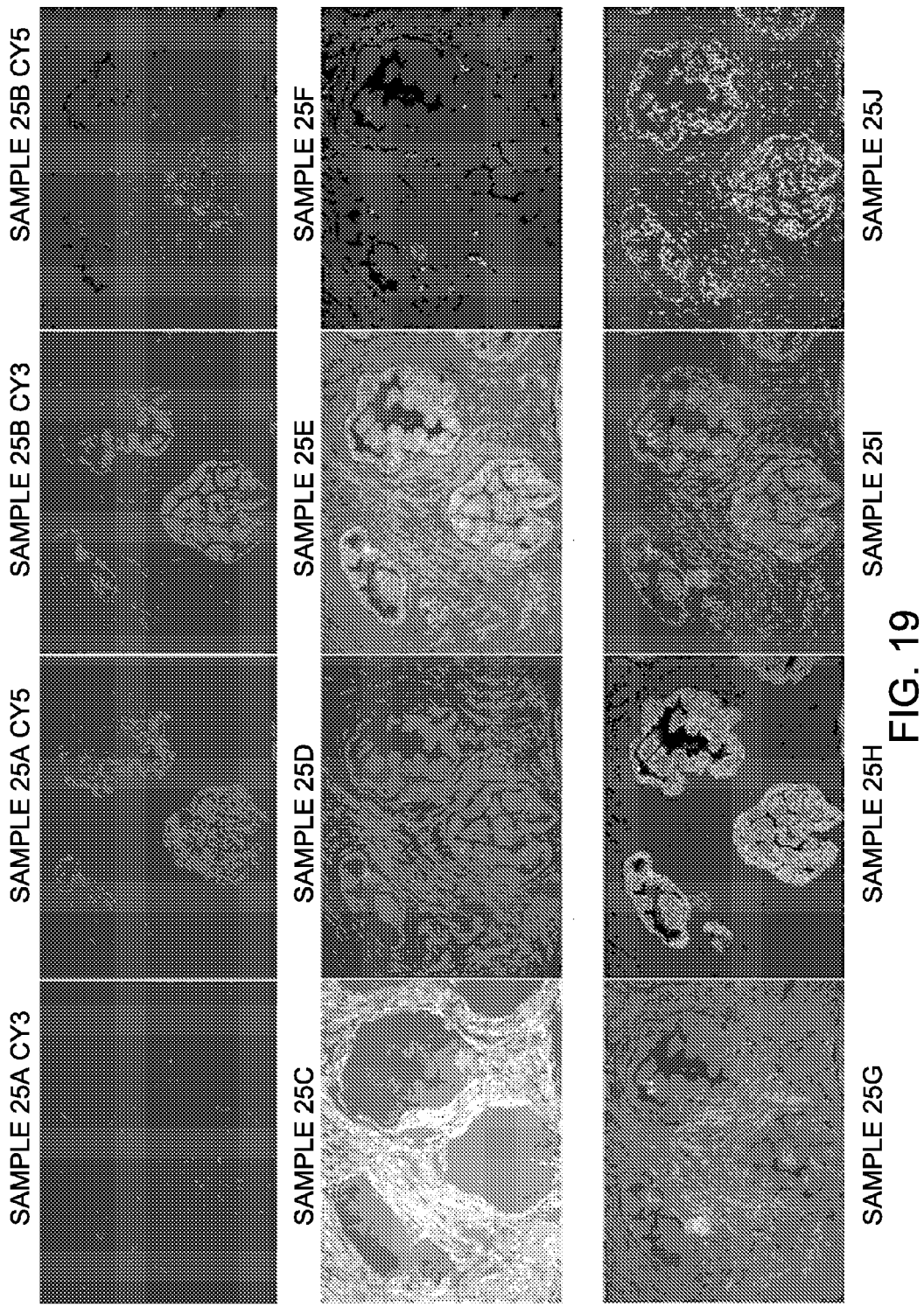
FIG. 19 shows the micrographs of Sample 25A (Cy3 and Cy5 channels), Sample 25B (Cy3 and Cy5 channels), and Samples 25C-25J.

FIG. 19 shows micrographs of Sample 25A (Cy3 and Cy5 channels), Sample 25B (Cy3 and Cy5 channels), and Samples 25C-25J. FIG. 19 shows that multiple imaging in the same Cy3 channel was possible by staining with different antibodies. 12-channel multiple imaging was possible with 9 of the channels being Cy3 channels.

Example 18

Four Channel Staining and Imaging of Normal Prostrate Using $H_2O_2$

Images were taken before staining to baseline the autofluorescence coming from each channel. A normal prostrate slide was stained with a Cy3-directly conjugated anti-pan cadherin to form Sample 26A. The slide was imaged and treated with $H_2O_2$ (Sample 26B), restained with Cy3-conjugated anti-vimentin (Sample 26c), treated with $H_2O_2$ (Sample 26D), restained with Cy3-conjugated anti-pan cytokeratin (Sample 26E), treated with $H_2O_2$ (Sample 26F), restained with Cy3-conjugated anti-SmA (Sample 26g), and treated with $H_2O_2$ (Sample 26H).

Figure 20:
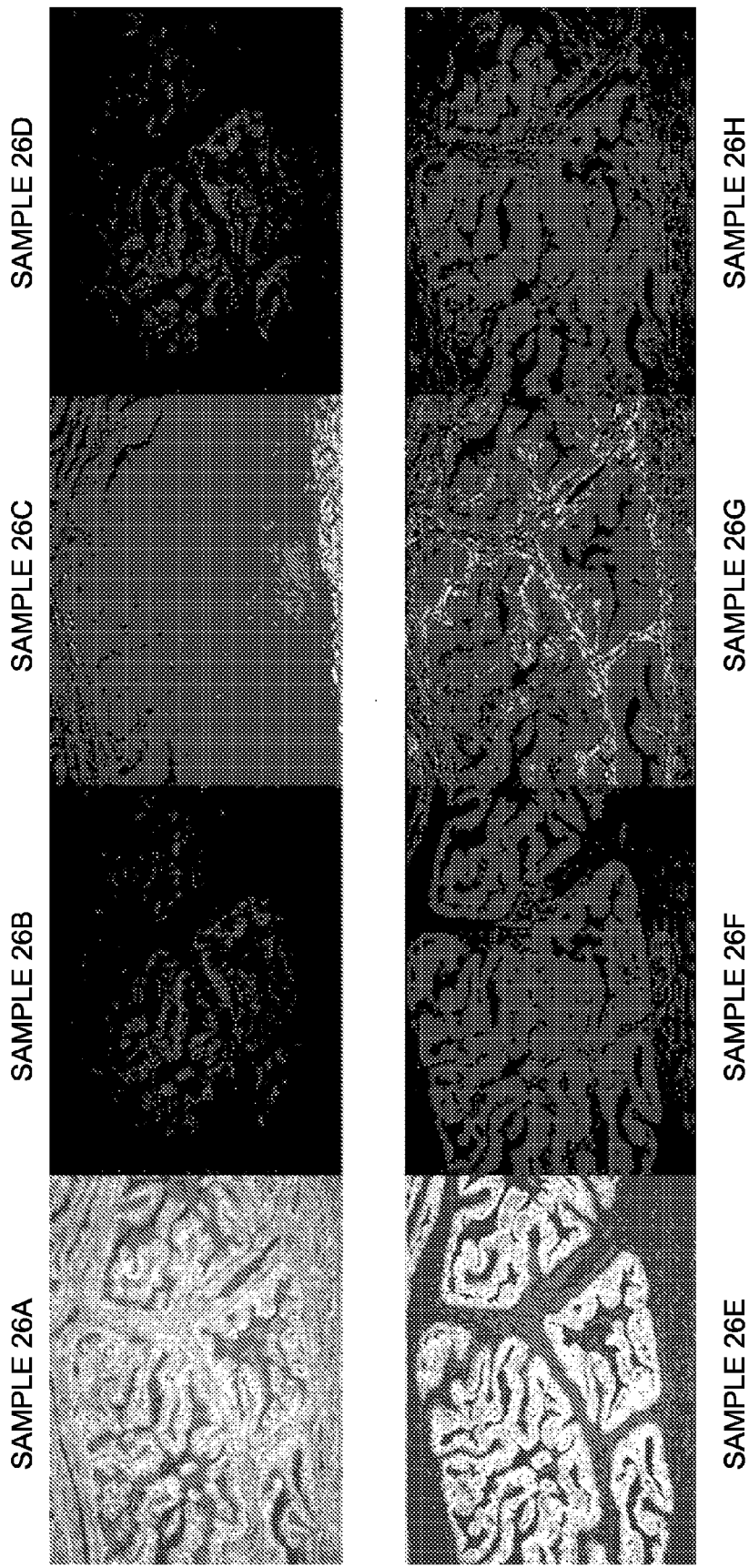
FIG. 20 shows the micrographs of Samples 26A-H.

FIG. 20 shows micrographs of Samples 26A-G. FIG. 20 shows that multiple imaging in the same Cy3 channel was possible by staining with different antibodies and destroying the signal using $H_2O_2$.

Example 19

Residual Stain Following Staining for Abundant Proteins Using NaOH

Figure 21:
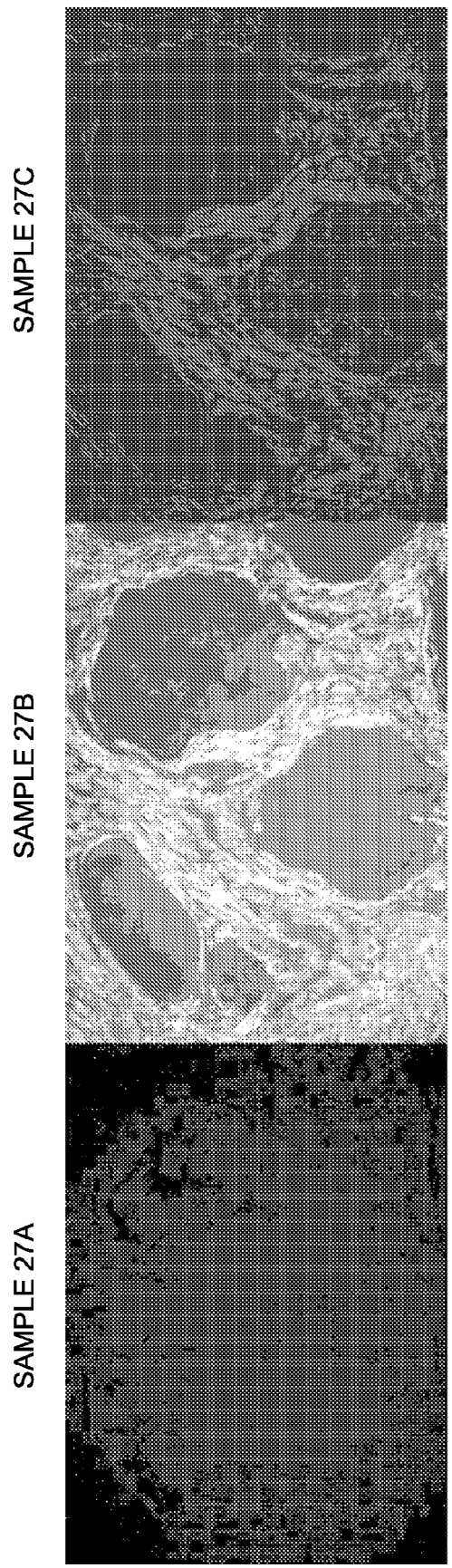
FIG. 21 shows the micrographs of Samples 27A-C.

A normal prostrate (Sample 27A) was imaged in the Cy3 channel to measure the autofluorescence from the tissue. Sample 27A was then stained with Cy3-conjugated anti-SmA to form Sample 27B, imaged and then treated with NaOH to form Sample 27C, and imaged again. Staining, imaging, and dye destruction steps were performed according to the procedures described herein in Examples 8 and 9. FIG. 21 shows the micrographs of Samples 27A-C. Residual stain was observed post NaOH treatment shown in sample 27C.

Figure 22:
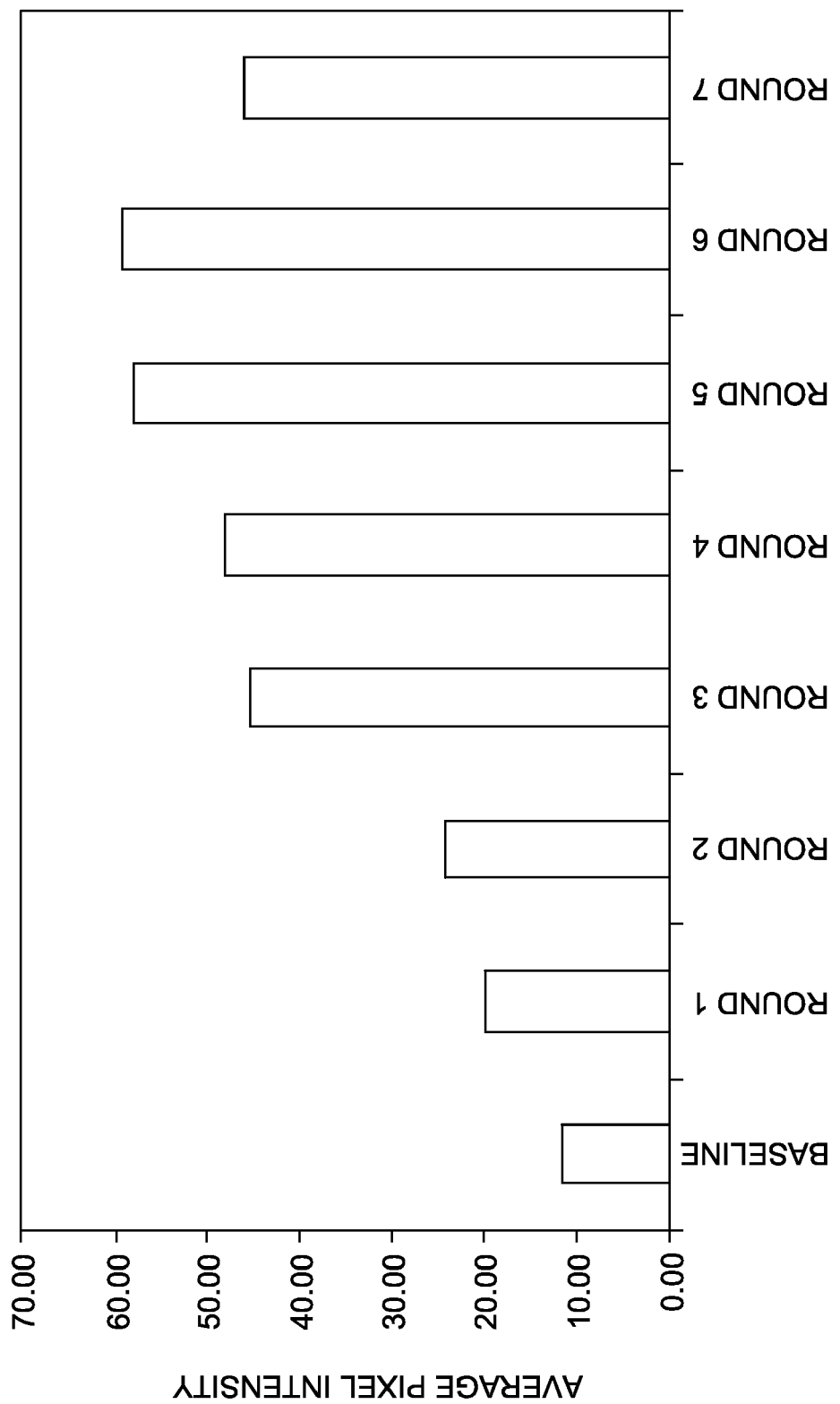
FIG. 22 shows the plot of average pixel intensity of the background for each cycle in the imaging in Example 20.

Residual stain values were also monitored during the twelve channels multiple imaging described in Example 17. Using Gimp 2.2, average pixel intensities were collected for each background and NaOH treated image and tabulated. FIG. 22 shows a plot of average pixel intensity of the background for each cycle in the imaging as well as a small image of what the background looked like prior to staining. A large spike in residual stain intensity was observed in cycle 4 as SmA, an abundantly expressed protein was stained in cycle 3.

Example 20

Residual Stain Following Staining for Abundant Proteins Using NaOH and $H_2O_2$ Treatment Two prostate slides were stained with Cy3-directly conjugated SmA (Samples 28A and 28B left panels). Both slides were given identical pretreatment steps, concentrations, antigen retrieval and the only difference was signal-destruction method: method-one being with NaOH (Sample 28C), the other with $H_2O_2$ (Sample 28D). Two other prostate slides were stained with Cy3-directly conjugated pan cadherin (Samples 29A and 29B right panels). Both slides were given identical pretreatment steps, concentrations, antigen retrieval and the only difference was signal destruction method; method one being with NaOH (Sample 29C), the other with $H_2O_2$ (Sample 29D).

Figure 23:
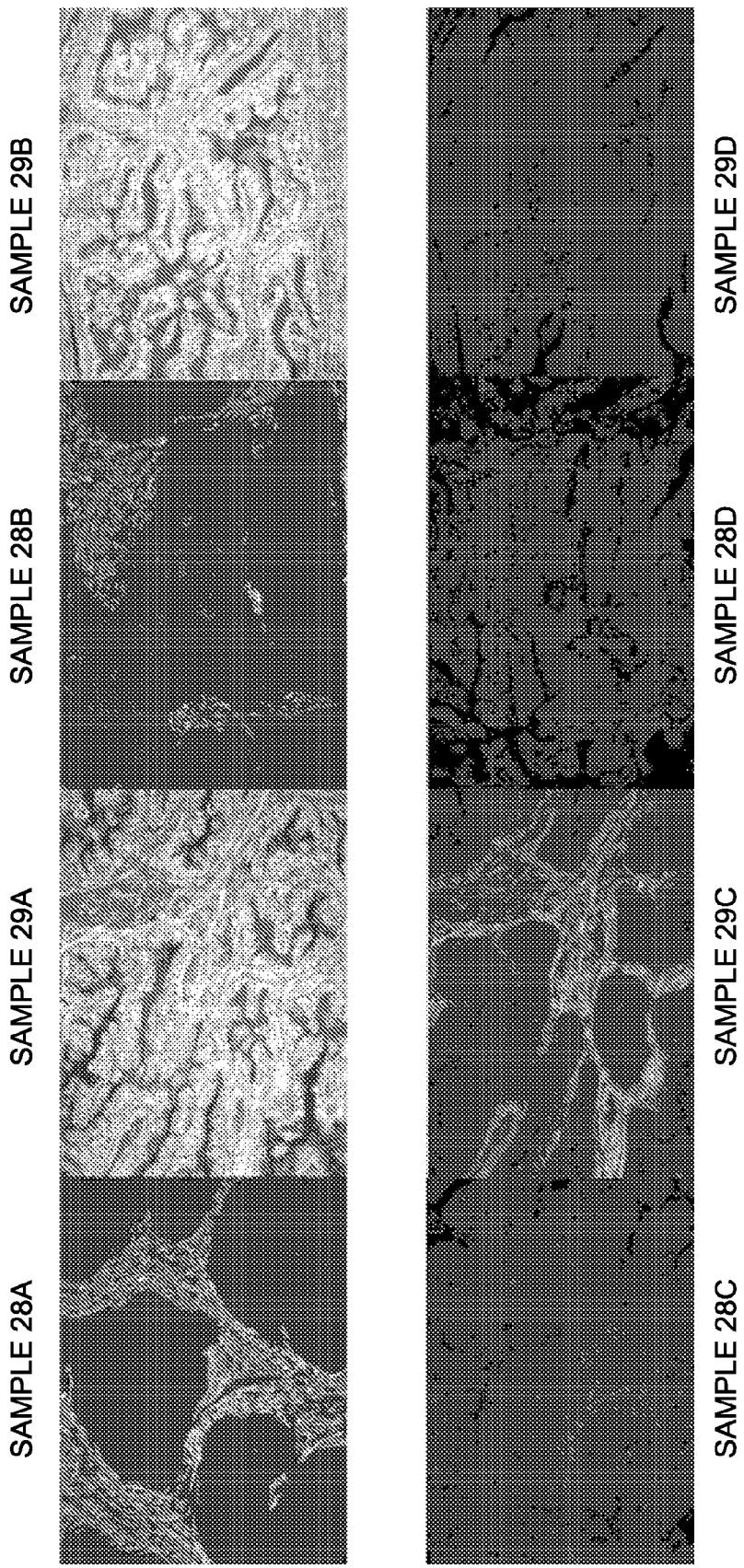
FIG. 23 shows the comparison between micrographs of Samples 28A-C and 29A-C.

FIG. 23 shows head-to-head micrographs of SmA and pan cadherin staining and signal removal. $H_2O_2$ showed more efficient dye removal for both SmA and pan cadherin when compared to NaOH.

Example 21

Residual Stain Following Multiple Cycle Staining for Abundant Proteins Using NaOH and $H_2O_2$ Treatment Two prostate slides were stained with Cy3-directly conjugated pan cadherin (Samples 30A and 30B). Both slides were given identical pretreatment steps including antigen retrieval and the only difference was signal-destruction method; method one being with NaOH, the other with $H_2O_2$. The slides were subjected to 9 mock staining-and-signal-destruction cycles before staining with Cy3-conjugated pan-cytokeratin to produce Sample 30C and Sample 30D in FIG. 24.

Figure 24:
FIG. 24 shows the micrographs of Samples 30A-D.
Figure 24:
Figure 24:
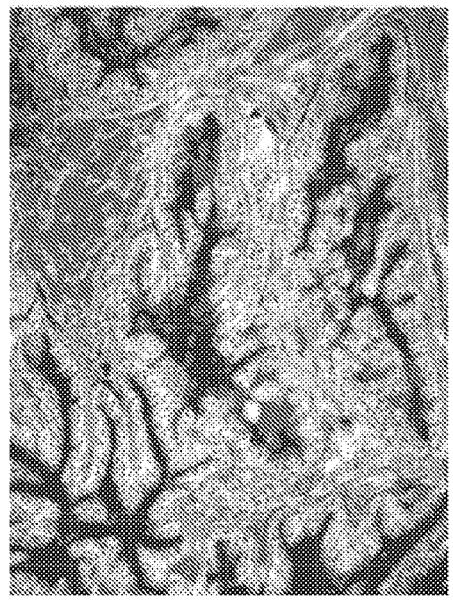
Figure 24:
Figure 25:
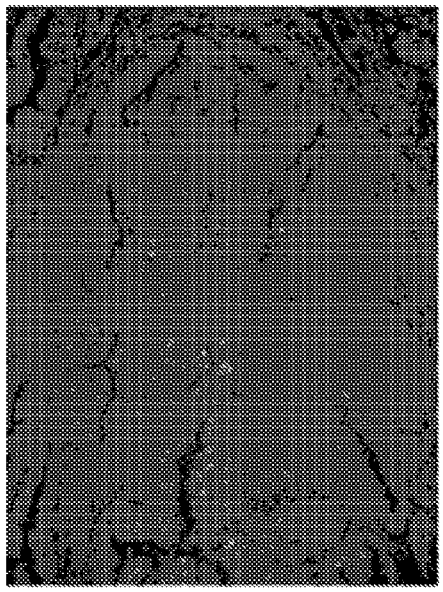
FIG. 25 shows the micrographs of Samples 30C-F.
Figure 25:
Figure 25:
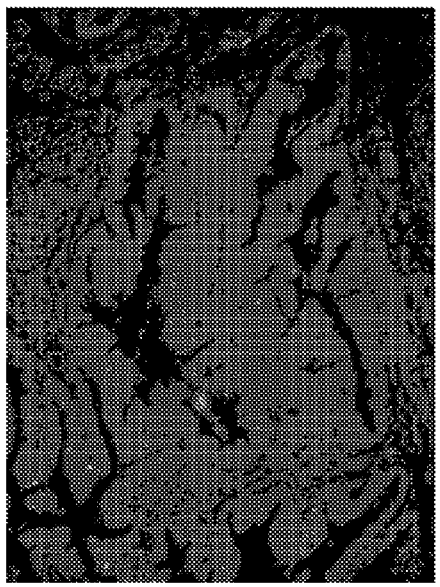
Figure 25:
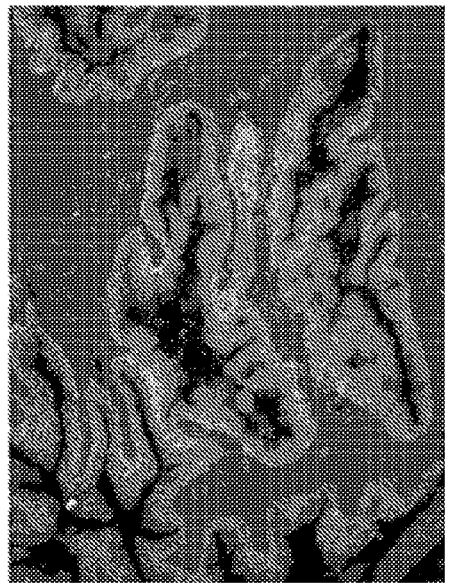
Figure 26:
FIG. 26 shows the plot of average pixel intensities for the background of each cycle for Samples 30C and 30D.

FIG. 24 compares staining from first cycle pan cadherin stain to the $9^{th}$ cycle of pan cytokeratin using NaOH or $H_2O_2$ to destroy the signal after each staining. FIG. 25 compares background from after dye removal (Samples 30E and 30F) in the first cycle and after 9 cycles of NaOH or $H_2O_2$ treatment (Samples 30C and 30D). $H_2O_2$ (Sample 30D, FIG. 25) showed more efficient dye removal of pan keratin when compared to NaOH (Sample 30C, FIG. 25) after the $9^{th}$ step FIG. 26 is a plot of average pixel intensities for the background of each cycle for the NaOH or $H_2O_2$ slides. As the plot in FIG. 26 shows, the background for the H₂O₂ slide was significantly less for each cycle after the initial baseline.

Example 22

Antibody Stability to Chemical Agents

Figure 27:
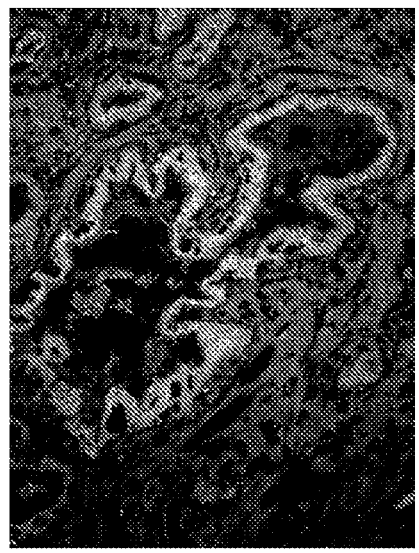
FIG. 27 shows the micrographs of Samples 31A, 31B, and 31C.
Figure 27:
Figure 27:
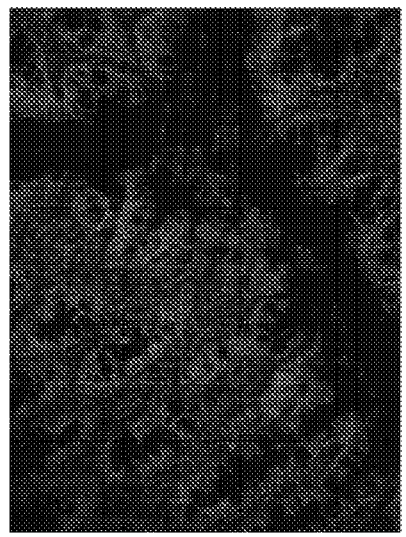

A colon tissue slide was stained with a primary antibody rabbit anti-beta catenin and detected with a Cy3-conjugated donkey anti-rabbit secondary antibody to form Sample 31A. Sample 31A was imaged and then treated with a NaOH solution to form Sample 31B, which was imaged again. Staining, imaging, and dye destruction steps were performed according to the procedures described herein in Examples 8 and 9. Sample 31B was restained with a Cy3-conjugated anti-rabbit secondary antibody to form Sample 31C, and imaged again. FIG. 27 shows micrographs of Samples 31A-C. FIG. 27 shows that the primary antibody remains bound to the sample after NaOH treatment.

Figure 28:
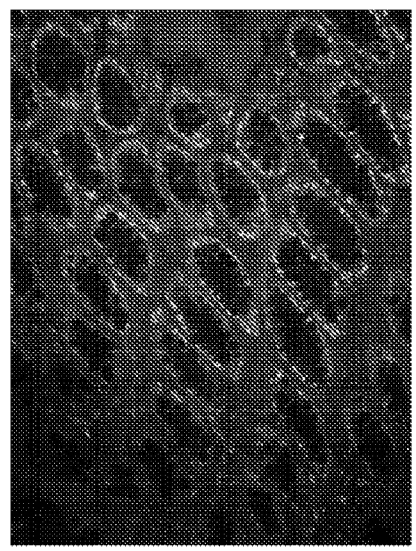
FIG. 28 shows the micrographs of Samples 32A, 32B, and 32C.
Figure 28:
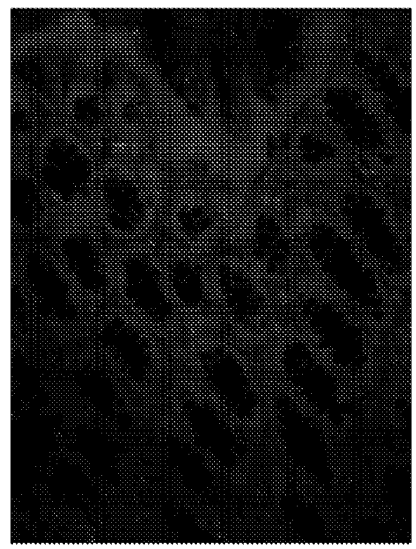
Figure 28:
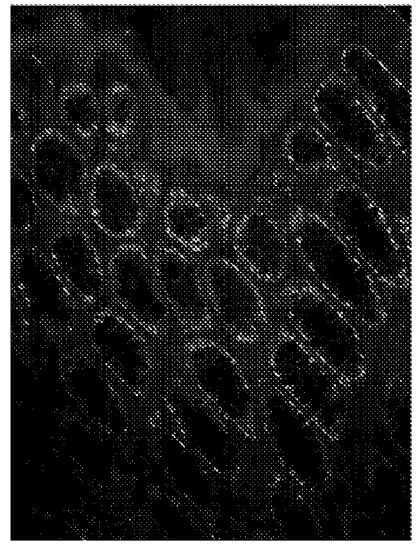

A colon tissue slide was stained with a primary antibody mouse-anti-PCNA and detected with a Cy3-conjugated donkey anti-mouse secondary antibody to form Sample 32A. Sample 32A was imaged and then treated with a NaOH solution to form Sample 32C, which was imaged again. Staining, imaging, and dye destruction steps were performed according to the procedures described in Examples 8 and 9. Sample 32B was restained with a Cy3-conjugated anti-mouse secondary antibody to form Sample 32C, and imaged again. FIG. 28 shows that the primary antibody is still bound to the sample after treatment with NaOH.

The following examples 23-26 illustrate embodiments of the invention according to which multiple imaging of tissue samples is conducted using enzyme-substrate-fluorophore conjugates. Multiple staining is obtained by staining, imaging, chemically destroying the fluorophore, restaining, imaging, and repeating the steps

Example 23

Conjugation of Antibodies with an Enzyme

The antibodies used were rabbit anti-β-catenin directly conjugated to horse radish peroxidase (HRP) enzyme, mouse anti-keratin 5 and donkey anti-mouse conjugated to HRP antibody. The substrate for the HRP enzyme was Cy5-conjugated tyramide substrate.

Example 24

Staining and Imaging of Tissue with HRP

Figure 29:
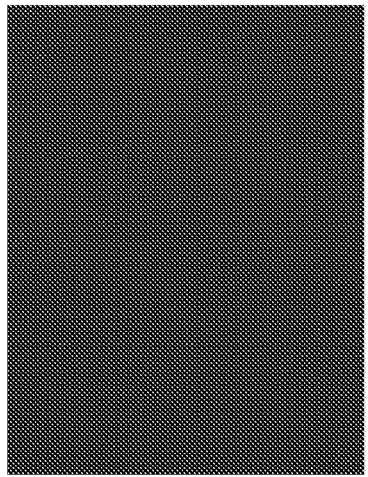
FIG. 29 shows the micrographs of Samples 33, 34, 35, and 36.
Figure 29:
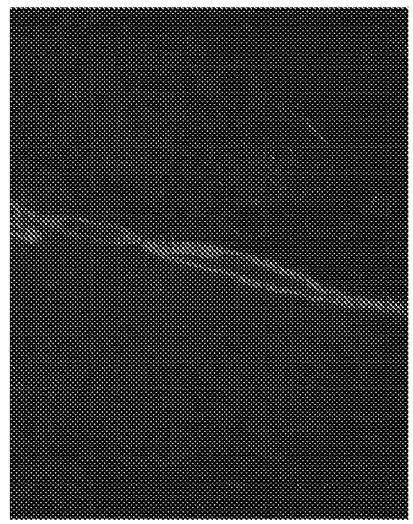
Figure 29:
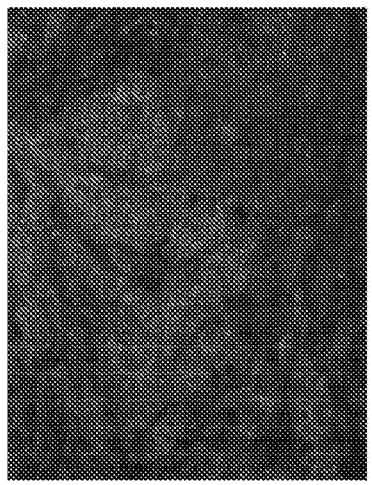
Figure 29:

A slide prepared in as Example 6 was incubated with HRP-conjugated anti-β-catenin antibody prepared in Example 23. Primary antibody incubation was conducted in 3 percent BSA for 45 minutes at 37° C. After incubation, the slide was subjected to an extensive series of PBS washes. The HRP-stained slide was incubated with Cy5-conjugated tyramide substrate in PBS/0.1% Triton X-100 for 10 minutes. After incubation, the slide was subjected to an extensive series of PBS washes. The Cy5 tyramide substrate was then imaged with a Zeiss Axio Imager. The magnification used was 20× unless otherwise stated. FIG. 29 shows a micrograph of Sample 33 after staining for β-catenin. After image acquisition, the slide was washed with PBS to prepare for signal destruction.

Example 25

Modification of Signal, Staining and Imaging

H₂O₂ solution was used for signal destruction. A H₂O₂ solution was prepared by mixing 10 mL of 0.5 M sodium carbonate (pH 10), 5 mL of 30 volume percent H₂O₂, and 35 mL of water. A slide was placed in the H₂O₂ solution for 15 minutes with gentle agitation. After 15 minutes, the slide was washed again with PBS (Sample 34), coverslipped and imaged again to check the efficacy of the dye destruction. The reimaging step was carried out using the process described above in Example 24. FIG. 29 shows a micrograph of Sample 34 after signal modification showing substantial removal of signal after signal destruction. Sample 34 was then re-incubated with Cy5-tyramide to determine residual activity of the HRP enzyme and imaged as above. FIG. 29 shows a micrograph of Sample 35 and no further Cy5 and HRP enzyme is chemically inactivated by H₂O₂ solution such that no further enzyme-substrate reaction occurs.

Example 26

Restaining and Reimaging of Tissue with Dye

The slide (Sample 35) from Example 25 was incubated mouse anti-keratin 5 antibody. Incubation was conducted in 3 percent BSA for 45 minutes at 37 C. After incubation, the slide was subjected to an extensive series of PBS washes. The keratin 5 antibody was then detected with an HRP conjugated donkey anti-mouse antibody in BSA for 45 minutes at 37° C. The HRP-stained slide was incubated with Cy5-conjugated tyramide substrate as in Example 25. After incubation, the slide was subjected to an extensive series of PBS washes. The Cy5-restained slide (Sample 36) was counterstained with the morphological stain, DAPI, and coverslipped. The coverslipped slide was re-imaged using the process described above in Example 24. FIG. 29 shows a micrograph of Sample 36 after staining for k5 protein.

The following Examples 27-31 illustrate embodiments of the invention according to which multiple imaging of dot blots is conducted. Multiple staining is obtained by staining, imaging, chemically destroying the fluorophore, restaining, imaging, and repeating the steps

Example 27

Immobilization of Targets on a Blot

Target proteins, β-catenin peptide (Sigma 26561-1 lot R1078-005) and CEA antigen were spotted on a polyvinylidene fluoride (PVDF) membrane at three different concentrations: 1 micrograms, 100 nanograms, and 10 nanograms. The blot was blocked using 5% milk, in 1×TBS-T (Tris-buffered saline Tween 20 buffer) for 1 hour at room temperature.

Example 28

Staining of β-Catenin and Imaging of Blots

Figure 30:
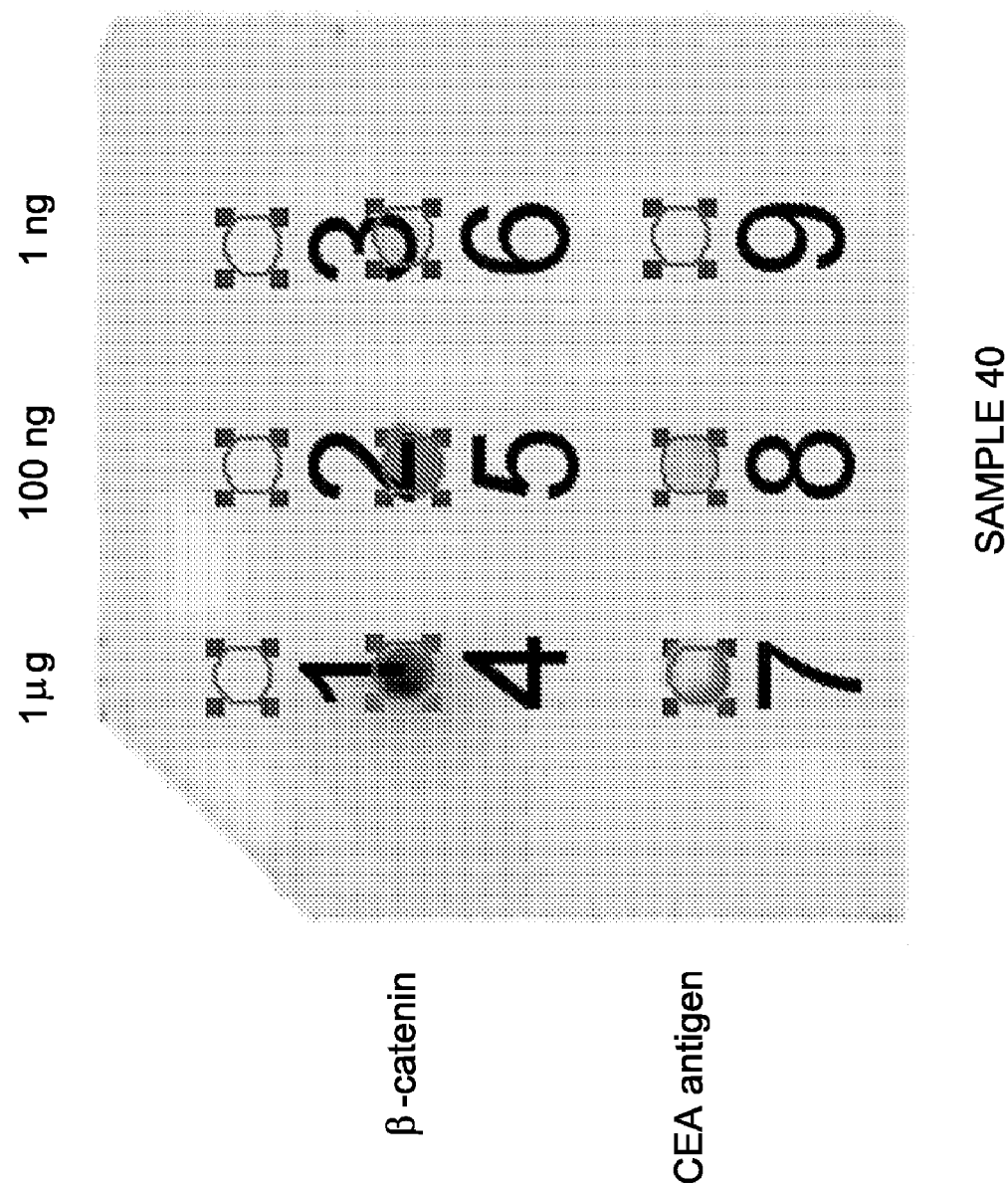
FIG. 30 shows the dot blots for Samples 37, 38, 39 and 40.

A blot prepared in Example 27 was incubated with a primary antibody, rabbit anti-β-catenin antibody (Sigma, C7738). Incubation was conducted at 1:200 dilution of antibody using 1 percent milk in 1×TBS-T for 1 hour at room temperature (RT). After incubation, the blot was subjected to an extensive series of washes. The blot was then incubated with a dye-conjugated secondary antibody donkey anti-rabbit Cy5 (prepared as in Example 6) at 1:500 dilution using 1 percent milk in 1×TBS-T for 1 hour at room temperature (RT). After incubation, the blot (Sample 37) was washed with 1×TBS-T. Images of the blot (Sample 37) were captured on Typhoon Imager (GE Healthcare) using Cy5 channel and a voltage setting of 450V. FIG. 30 shows an image of Sample 37. As shown in FIG. 30, spots of variable signal intensities are observed for the three different concentrations of β-catenin target protein.

Example 29

Dye Destruction, and Imaging $H_2O_2$ solution was used for signal destruction. A $H_2O_2$ solution was prepared by mixing 10 mL of 0.5M sodium carbonate (pH 10), 5 mL of 30 volume percent $H_2O_2$, and 35 mL of water. The blot prepared in Example 28 was placed in the $H_2O_2$ solution for 15 minutes at room temperature with gentle agitation. After 15 minutes, the blot was washed three times using 1×TBS-T for 5 minutes to form Sample 38. The blot (Sample 38) was reimaged and images of the blot were captured on Typhoon Imager (GE Healthcare) using Cy5 channel and a voltage setting of 450V. FIG. 30 shows an image of Sample 38. As shown in FIG. 30, no spots were observed after the dye destruction step indicating substantially complete destruction of Cy5.

Example 30

Staining of CEA Antigen and Imaging of Blot

The blot from Example 29 was incubated with a primary antibody mouse anti-CEA antibody. Incubation was conducted at 1:200 dilution using 1 percent milk in 1×TBS-T for 1 hour at room temperature (RT). After incubation, the blot was subjected to an extensive series of washes. The blot was then incubated with a dye-conjugated secondary antibody donkey anti-mouse Cy5 (prepared in Example 6) at 1:500 dilution using 1 percent milk in 1×TBS-T for 1 hour at room temperature (RT). After incubation, the blot (Sample 39) was subjected to an extensive series of washes. Images of the blot (Sample 39) were captured on Typhoon using Cy5 channel and a voltage setting of 450V. FIG. 30 shows an image of Sample 39. As shown in FIG. 30, spots of variable signal intensities are observed for the three different concentrations of CEA antigen. The Example illustrates that two different targets may be detected using a single signal generator.

Example 31

Quantification of Signal after Each Step

Figure 31:
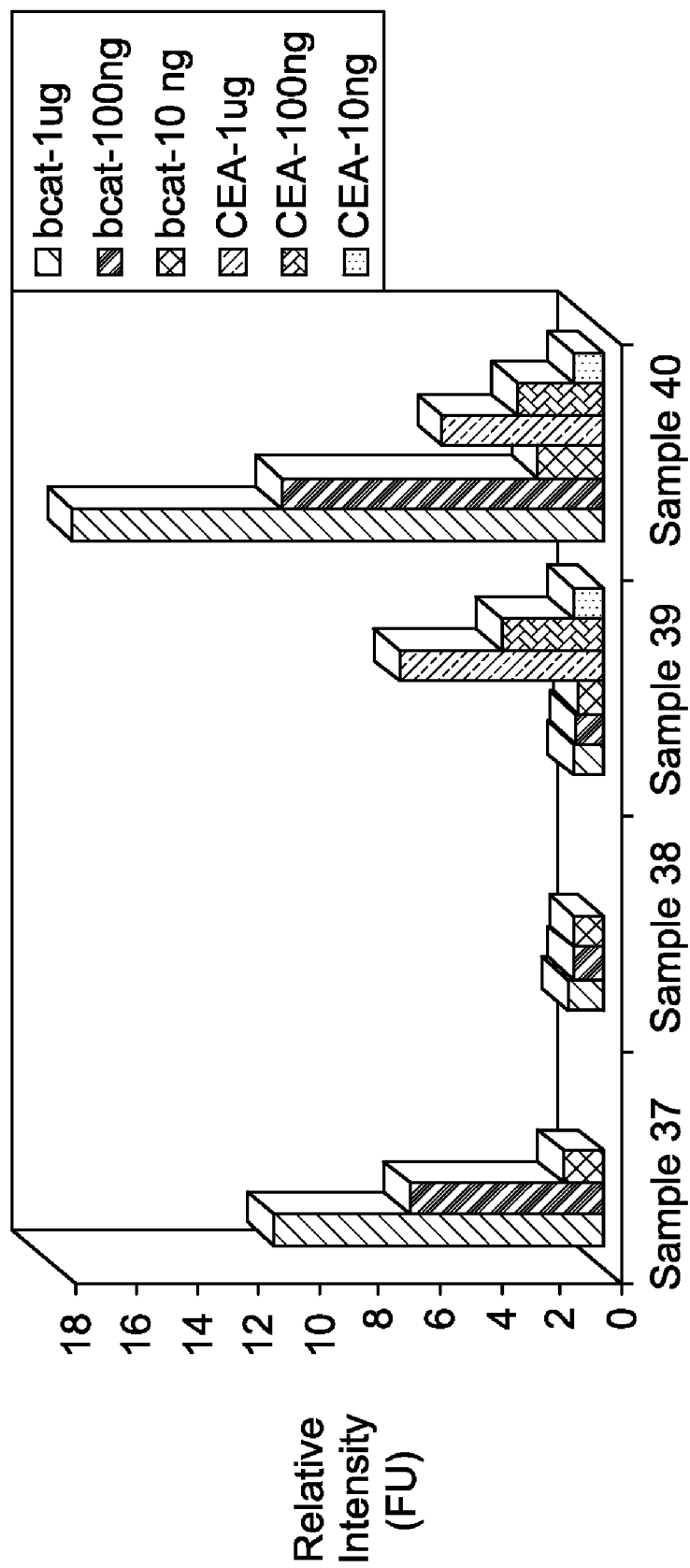
FIG. 31 shows the bar chart of relative signal intensities of dots for Samples 37, 38, 39 and 40.

Samples 37, 38, 39, and 40 were further analyzed to quantify the signals in the three detected spots for each peptide (a representative example of regions chosen for analysis is shown in FIG. 30 with regions highlighted by a square numbered 4-9 in FIG. 30). The signals from each sample each of the peptide spots were normalized to an average of three background spots 1, 2, and 3 as shown in FIG. 30. FIG. 31 is a plot of relative signal intensities of the spots for Samples 37, 38, 39, and 40, showing that signal intensities reduce 10-fold after the dye-destruction step (Sample 38).

The following examples 32-34 illustrate embodiments of the invention according to which the fluorophore is destroyed by an oxidizing agent without significantly stripping the probe (primary antibody) from the solid-support.

Example 32

Preparation of Cell Cultures

Alexa 488, BODIPY FL C5 (D6184), hydroxycoumarin (H1193) were obtained from Invitrogen (Carlsbad, Calif.); ATTO 495, ATTO 635, and ATTO 655, were obtained from ATTO-TEC (Siegen, Germany); DY-734-NHS was obtained from Dyomics (Jena, Germany); Fluorescein cadaverine was obtained from Biotium Inc. (Hayward, Calif.). Goat anti-mouse IgG-Cy3 and goat anti-mouse IgG-Cy5 were obtained from Jackson ImmunoResearch Laboratories, Inc. (West Grove, Pa.). DPBS and PBS were obtained from Invitrogen; 16% PFA were obtained from Electron Microscopy Sciences (Hatfield, Pa.). Goat serum was obtained from Vector Laboratories (Burlingame, Calif.). All other reagents were obtained from Sigma (St. Louis, Mo.).

LS174T cells (ATCC, CL-188) expressing carcino embryonic antigen (CEA) were cultured in EMEM (ATCC, cat#30-2003) Supplemented with 10% FBS. Cells were incubated at 37° C. and 5% $CO_2$. Upon 90% confluence, they were subcultured or seeded into 96-well-plates and continued to grow for additional two days.

Confluent cells on 96-well-plates were rinsed with DPBS (with calcium) twice, and then 2% PFA (final concentration) was added to fix cells for 10 minutes, followed by permeabilization using 0.1% Triton X-100 in PBS for 5 minutes. Next, cells were incubated in a blocking buffer (10% goat serum+3% BSA) for 1 hour at room temperature. Mouse anti-CEA (final concentration 10 µg/ml in 3% BSA) was added immediately after the blocking step and incubated overnight.

Example 33

Contacting the Primary Antibody with Oxidizing Agents

To investigate the effect of oxidizing agents on primary antibody, various oxidizing agent solutions (as described in Table 1) were added to half the plate for 30 minutes, and then rinsed thoroughly with PBS. The oxidizing reagents employed were hydrogen peroxide, aqueous bromine, potassium permanganate, sodium dichromate, $I_2$/KI solution, t-butyl peroxide, and t-butyl hydrogen peroxide. The other half of the plate was used as control with parallel PBS incubations and washes and no oxidizing agent solutions were applied. To test the effect of a base on the probe different bases, such as NaOH, aqueous DBU (diazobicyclos-undecene), and aqueous butyl amine were also contacted with the plate. PBS was applied as a control agent.

All wells were incubated with 50 µl/well goat anti-mouse IgG-Cy3 or goat anti-mouse IgG-Cy5 (1:200 dilution). The whole plate was scanned using Gemini M5 spectrophotometer (Molecular Device, Sunnyvale, Calif.). A total of five spots were scanned in each well and then averaged to get one reading for each well. For Cy3 dye, fluorescence was read at excitation wavelength at 544 nm, emission 580 nm, and cutoff 570 nm. For Cy5, Excitation 640 nm, Emission 675, and cutoff 665.

Table 1 shows the fluorescence values measured after application of the oxidizing agent to the primary antibody as shown in columns 2 (Cy3) and 4 (Cy5). The values in the Table are normalized fluorescence intensity, that is, a ratio of the fluorescence intensity measured for wells contacted with the oxidizing agent to the fluorescence intensity measured for the control wells (no oxidizing solution applied) multiplied by 100. Therefore, a value close to 100% means that the oxidizing solution has no effect on primary antibody when compared to its control (no oxidizing solution applied).

Table 1 shows that some oxidizing agent (e.g. $H_2O_2$) have almost no effect on primary antibody (P>0.1), whereas in other cases, the concentration of the oxidizing agent may be varied (e.g., for $I_2$/KI) such that the primary antibody is not effected substantially. The bases employed (NaOH and butyl amine) exhibited substantial destruction of the primary antibodies across a variety of concentrations employed. PBS showed no effect on the primary antibody.

Example 34

Contacting the Fluorophores with Oxidizing Agents

To test the effect of oxidizing agent on fluorophore-labeled cells, various oxidizing agent solutions (as described in Table 1) were added to different rows (control part of the plate) for 30 minutes. The plate was read again after thorough washing as described in Example 33.

Table 1 shows that some oxidizing agent (e.g. $H_2O_2$) have almost no effect on primary antibody but result in substantial loss of fluorescence properties for the cyanine dye. The data reported in Table 1 further shows that fluorescent signal destruction worked better at high pH for $H_2O_2$ solutions. As described herein, in other cases, the concentration of the oxidizing agent may be varied (e.g. for $I_2$/KI) such that the primary antibody is not affected substantially but the cyanine dye is. The bases employed (NaOH and butyl amine) exhibited substantial loss of signal from the cyanine dye but this may be due to destruction (or stripping) of the primary antibodies by the base. PBS showed no effect on the primary antibody and the cyanine dye.

TABLE 1

Normalized fluorescence intensity measured after contacting the plate with different oxidizing agents.

| Bleaching Solution | On primary Cy3 (up to 6 sets) | Bleaching Cy3 (up to 4 sets) | On Primary Cy (2 sets) | Bleaching Cy5 (1 set) |
|---|---|---|---|---|
| Oxidizing reagents | | | | |
| 3% $H_2O_2$, pH10 | 105% | 11% | 124% | 0% |
| 3% $H_2O_2$ pH5 | 99% | 73% | | |
| Aqueous Bromine | 100% | 14% | | |
| 4% potassium permanganate | 0% | 0% | 1% | 0% |
| 1% potassium permanganate | 80% | 4% | | |
| 4% sodium dichromate.2$H_2O$ | 111% | 69% | 88% | 25% |
| 4% sodium dichromate.2$H_2O$ in Acetic acid | 213% | 10% | | |
| 5% $I_2$, 10% KI | 9% | 0% | 7% | 4% |
| 0.5% $I_2$, 1% KI | 82% | 10% | | |
| 0.05% $I_2$, 0.1% KI | 101% | 72% | | |
| 3.5% t-butyl peroxide in Acetonitrile | 45% | 103% | 49% | 84% |
| 3.5% t-butyl hydroperoxide | 166% | 65% | 107% | 44% |
| Bases | | | | |
| 0.35 N NaOH | 17% | 11% | 14% | |
| 0.1 N NaOH | 37% | 13% | 34% | |
| 5% DBU | 40% | 12% | 40% | |
| 1% DBU | 38% | | 41% | |
| 5% Butylaminine | 20% | 13% | 38% | |
| Control | | | | |
| PBS | 108% | 79% | 91% | 96% |

Example 35

Measurement of Dye-Bleaching Spectrum

Optical density (O.D.) was used to monitor dye destruction. 10 μl of dye was mixed with equal volume of oxidizing solution and then 2 μl of the mixed solution was loaded to ND-1000 Spectrophotometer (Nanoprop Technologies, Inc. Wilmington, Del.). Optical density (O.D.) was read at a full spectrum ranging from 200 nm to 750 nm. For kinetic study, measurements were taken at time 0, 5 min, 15 min, and 30 min.

Example 36

Kinetic study of Cy3 and Cy5 Destruction with $H_2O_2$

Figure 32:
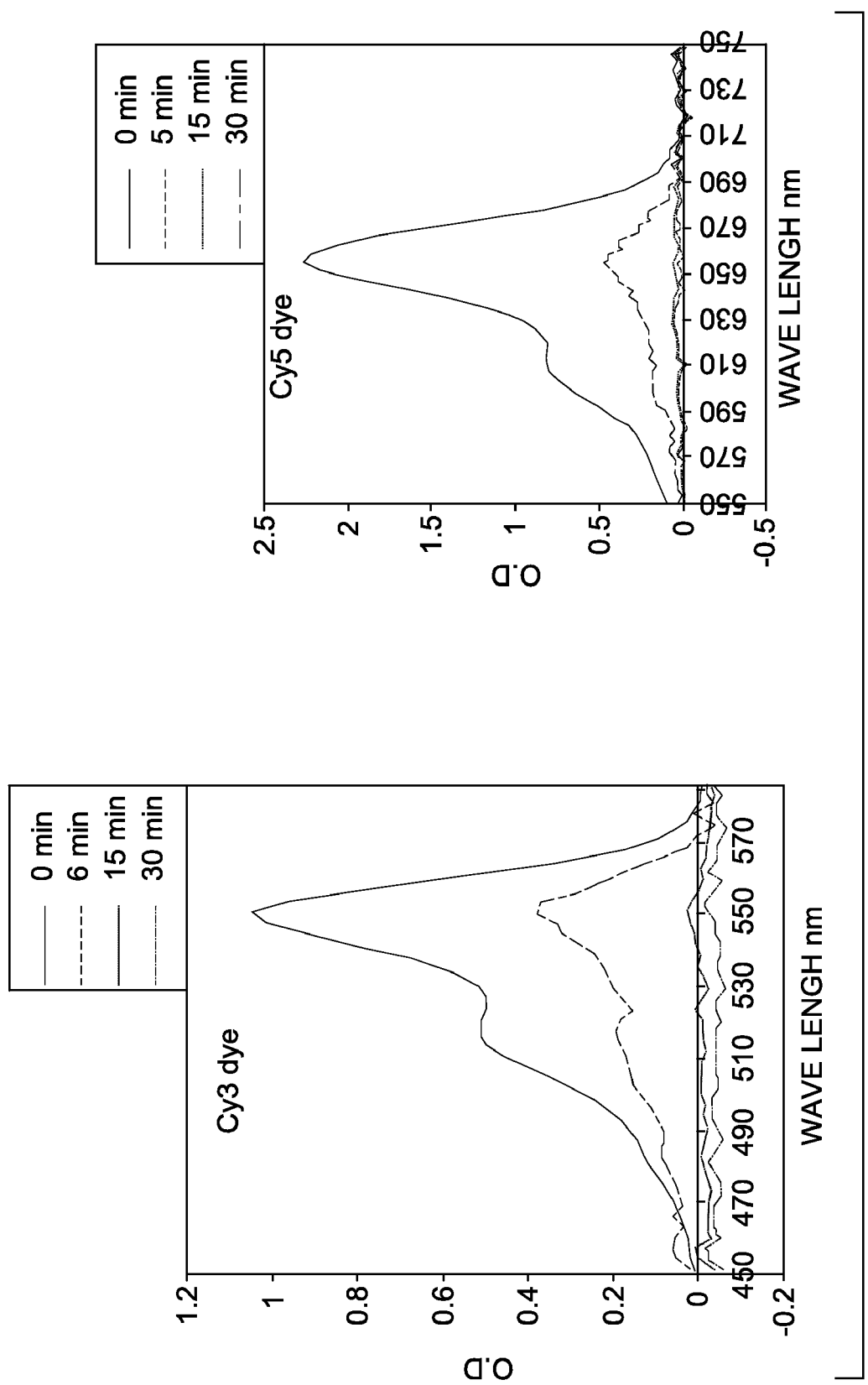
FIG. 32 shows the time profile of spectra of Cy3 and Cy5.

To study the kinetics of dye destruction, hydrogen peroxide (1.5% $H_2O_2$ at pH 10) was used as an oxidizing agent and Cy3 and Cy5 as representative dyes using the method describe in Example 36. The fluorescence spectrum of the dye-oxidizing solution mixture was monitored for a period of 30 minutes. FIG. 32 shows the time profile of spectrums of Cy3 and Cy5. A rapid decrease in O.D. was observed, indicating dye destruction. In both cases, 15 minute incubation in 1.5% $H_2O_2$ could practically destroy the dyes. O.D. values at peak excitation reduced to 2% for both Cy3 and Cy5 after 15 minutes.

Example 37

Effect of $H_2O_2$ Concentrations on Cy3 Bleaching

Figure 33:
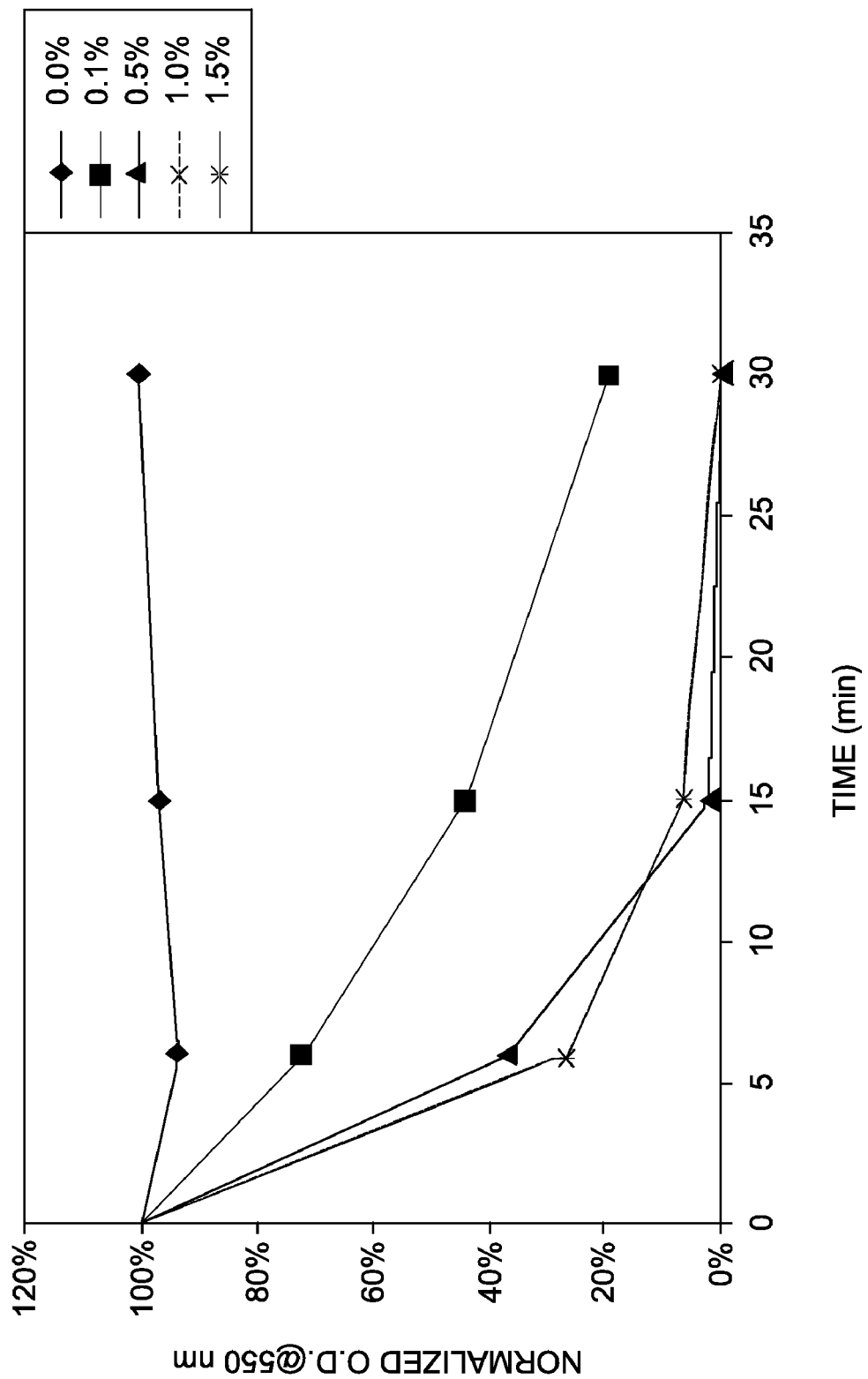
FIG. 33 shows the Cy3 absorbance values as function of time for different $H_2O_2$ concentrations.

A range of $H_2O_2$ concentrations from 0 to 1.5% were tested and absorbance spectrum was monitored over 30 minutes using the method described in Example 35. The pH of $H_2O_2$ solution was kept at 10. Cy3 was used as a dye, and absorbance was recorded at its peak wavelength at 550 nm. Except for 0.1% $H_2O_2$, all other concentrations of $H_2O_2$ showed very similar results, and almost reduced dye absorbance to 5% within 15 minutes as shown in FIG. 33. There is no statistical difference among treatments with concentrations of 0.5%, 1% and 1.5% (P>0.1).

Example 38

Effect of $H_2O_2$ on Various Fluorophores

Figure 34:
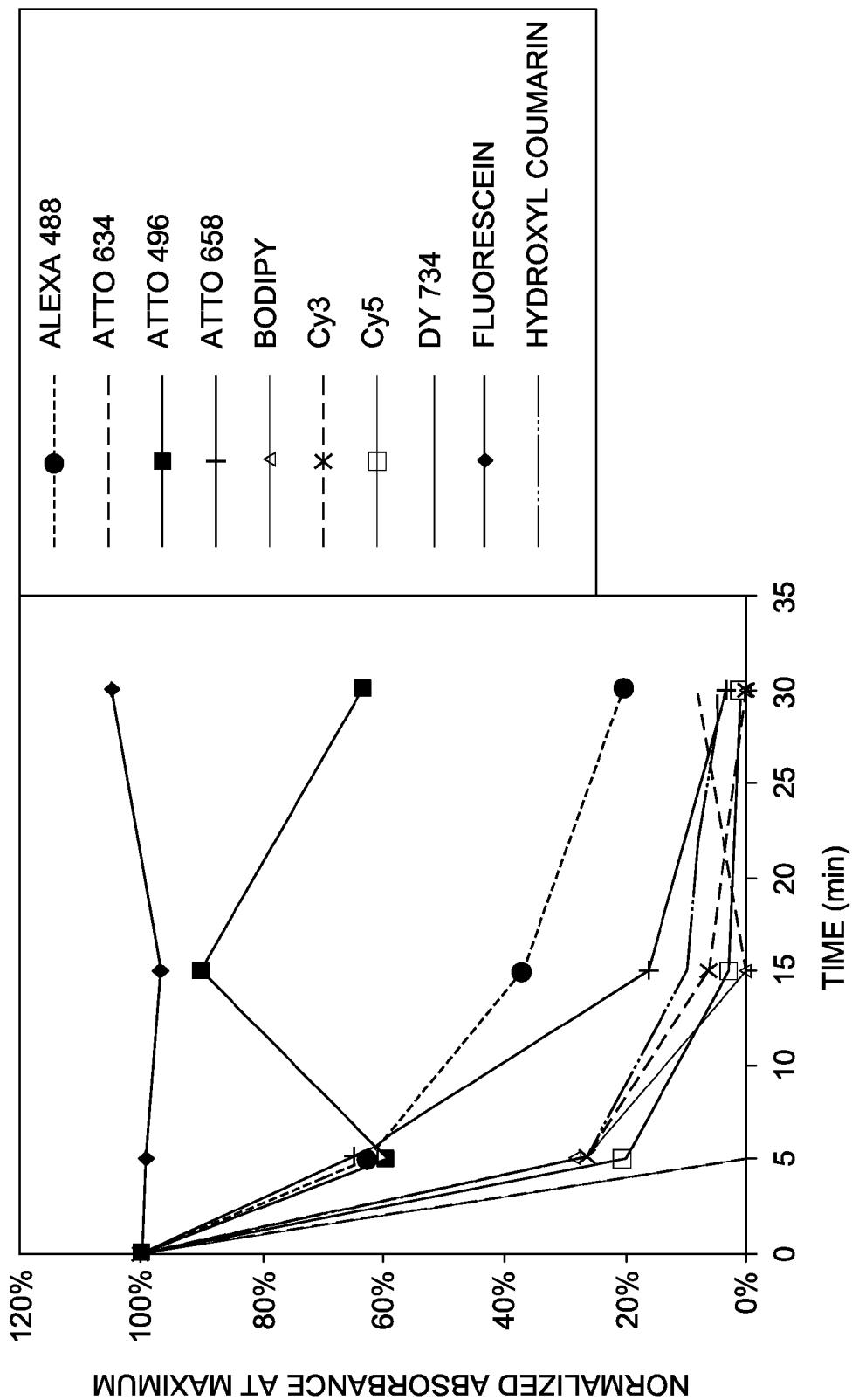
FIG. 34 shows the absorbance values as function of time for different fluorophores.

A panel of fluorescent dyes was tested for the effect of $H_2O_2$ (3% $H_2O_2$ at pH 10) on different fluorophores using the method described in Example 35. Absorbance spectrum was monitored over 30 minutes and the absorbance values are shown in FIG. 34. Data shown here are O.D. values at dye's maximum absorbance wavelength normalized to O.D. at time 0. Fluorescein, which is very sensitive to photobleaching, was relatively stable to this oxidizing method. ATTO 496 and Alexa 488, were also less sensitive to the oxidizing agent when compared to other dyes. FIG. 34 shows that the dyes could be destroyed using $H_2O_2$.

Example 39

Effect of $H_2O_2$ on Quantum Dots (QD 655)

A range of $H_2O_2$ concentrations (from 20× to 2000× dilution) were tested and absorbance spectrum was monitored over 30 minutes using the method described in Example 36. The pH of $H_2O_2$ solution was kept at 10. The absorbance values were compared to a control sample of a solution of QD 655 at different concentrations (from 20× to 2000× dilution).

Qdot 655 goat F(ab')2 anti-mouse IgG conjugate (1 uM) solution was diluted 10×, 100× or 1000× with 0.775M sodium bicarbonate solution (adjusted to pH 10). To each solution an equal volume of 6% hydrogen peroxide was added. 100 ul aliquots of each in triplicates were placed in a 96 well microtitre plate. Samples without peroxide but diluted to the same final concentration with water were used as controls. A 2× diluted bicarbonate solution was used as background control. Fluorescence was measured over time on spectromax M2 plate reader using following parameters: Excitation 350 nm, Emission 655 nm and auto cut off 630 nm. For the lowest concentration, 99% reduction in fluorescence was achieved after 5 min. With in 30 min, fluorescence of all peroxide samples was reduced by >99.5%. Fluorescence of control samples was mostly intact (>93% for the lowest conc. sample and ~99% for the highest conc. sample).

Figure 35:
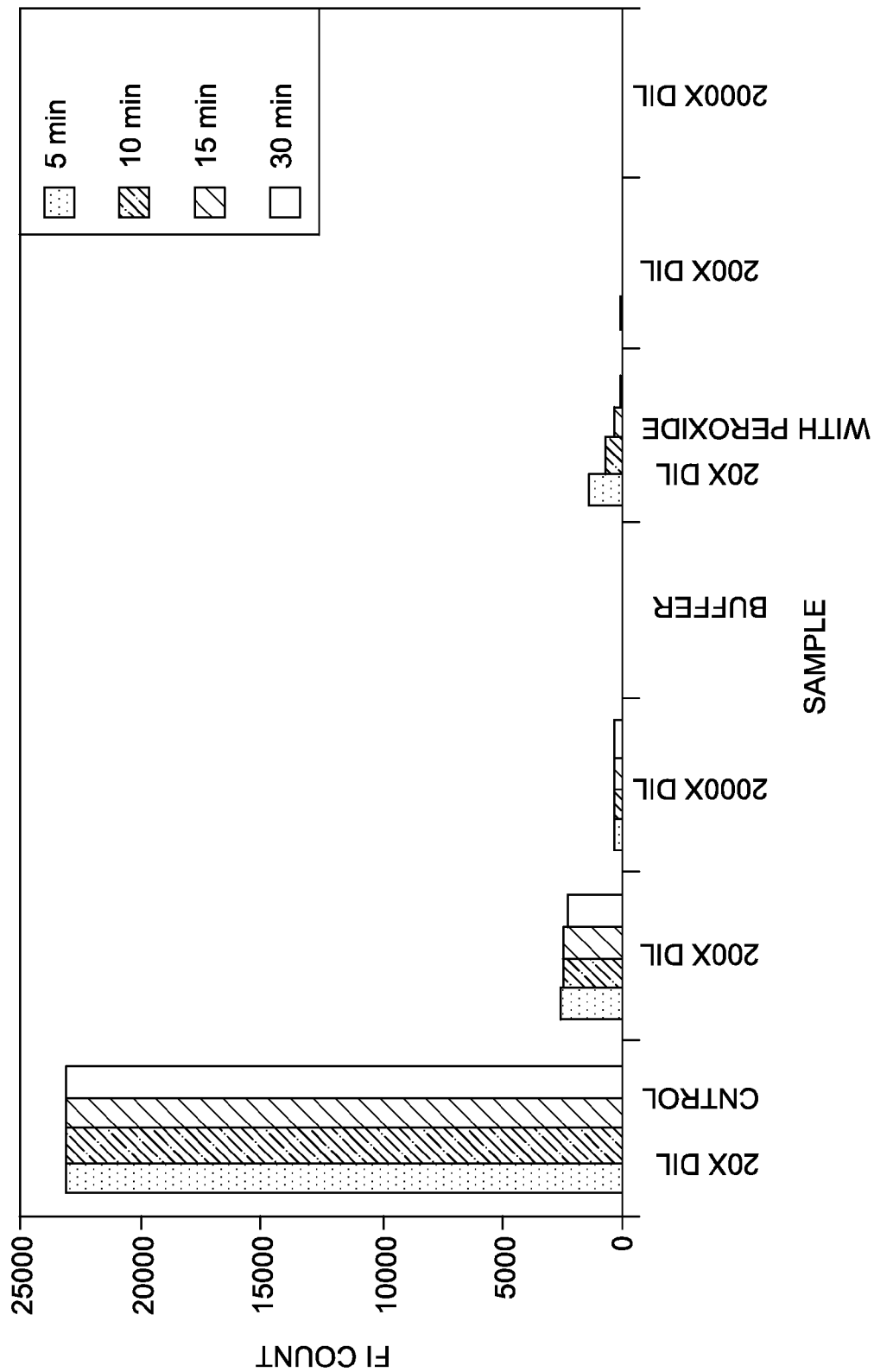
FIG. 35 shows the QD 655 absorbance values as function of time for $H_2O_2$.

Three percent hydrogen peroxide in bicarbonate buffer (pH 10) was used to destroy signal. The absorbance values were compared to a control sample of a solution of QD 655 at different concentrations (from 20× to 2000× dilution). At all concentrations of qdot the fluorescence reduced to less than 6% of the control value within 5 minutes as shown in FIG. 35.

Example 40

Effect of Hydroxyl Radicals on Fluorescein

Figure 36:
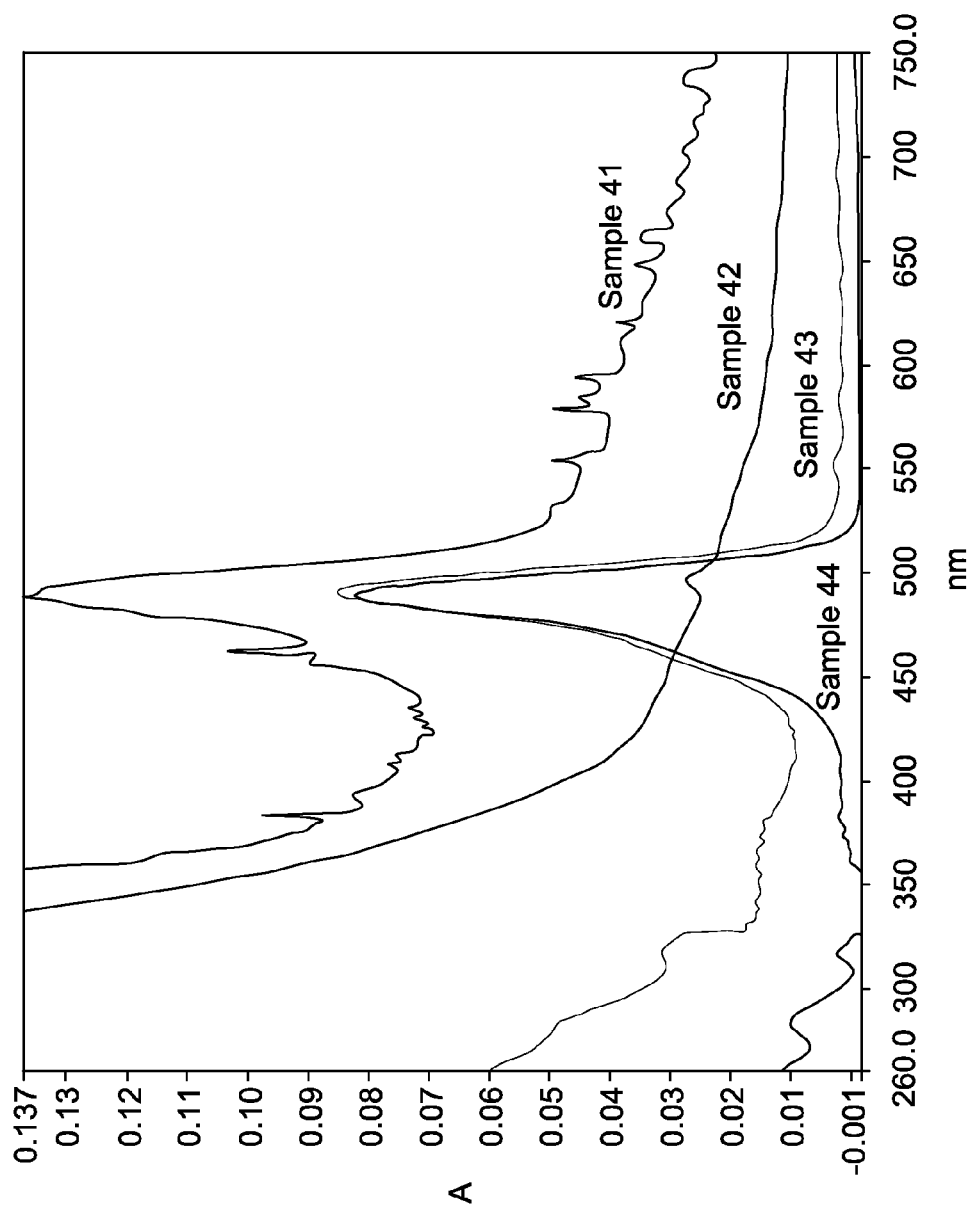
FIG. 36 shows the absorbance spectra for fluorescein using $H_2O_2$.

Absorbance spectra of the fluorescein dye FAM cadaverine ("FAM-CAD") were measured using different oxidizing agent conditions for Samples 41 (FAM-CAD, $H_2O_2$ and $H_2O$ (1:1:1), 42 (FAM-CAD, $H_2O_2$ and $FeCl_3$ (1:1:1)), 43 (FAM-CAD, $H_2O$ and $FeCl_3$ (1:1:1)), 44 (FAM-CAD and $H_2O$ (1:2)). A solution of Fluorescein-cadaverine was mixed with 9% hydrogen peroxide and a 2% solution of $FeCl_3$ in water in the ratio of 1:1:1 by volume. Mixture was allowed to stand for 5 minutes. Since the addition of $FeCl_3$ changes pH to highly acidic and fluorescein spectrum is known to be different under acidic conditions, prior to UV/VIS spectrum measurement, solution was made basic by addition of 1N NaOH, filtered and its spectrum was recorded. Solutions similarly treated except where either the hydrogen peroxide was replaced with water or $FeCl_3$ solution was replaced with water were used as controls. A solution where both $FeCl_3$ and hydrogen peroxide were replaced with water was also used as another control. Although in the presence of peroxide, spectra are a bit noisy and baseline is raised due to bubble formation, spectra clearly showed that while control samples were unaffected, practically all of the fluorescein was destroyed in the test sample. The absorbance reduced considerably after 5 minutes for Sample 42 as shown in FIG. 36, indicating that fluorescein can be destroyed by employing an oxidizing agent to create hydroxyl radicals.

The invention may be embodied in other specific forms without departing from the spirit or essential characteristics thereof. The foregoing embodiments are therefore to be considered in all respects as illustrative rather than limiting on the invention described herein. The scope of the invention is thus indicated by the appended claims rather than by the foregoing description, and all changes that come within the meaning and range of equivalency of the claims are therefore intended to be embraced therein. The invention may be embodied in other specific forms without departing from the spirit or essential characteristics thereof. The foregoing embodiments are therefore to be considered in all respects as illustrative rather than limiting on the invention described herein. The scope of the invention is thus indicated by the appended claims rather than by the foregoing description, and all changes that come within the meaning and range of equivalency of the claims are therefore intended to be embraced therein.

The invention claimed is:

1. A method of probing multiple targets in a biological sample comprising:
   (a) providing a biological sample containing multiple targets adhered to a solid support;
   (b) binding at least one fluorescent probe to one or more targets present in the sample;
   (c) observing a signal from the fluorescent probe bound in step (b);
   (d) oxidizing the bound fluorescent probe with a solution comprising an oxidizing agent that substantially inactivates the fluorescent probe;
   (e) binding at least one fluorescent probe to one or more targets present in the sample of step (d); and
   (f) observing a signal from the fluorescent probe bound in step (e).

2. The method of claim 1, wherein the solution in step (d) is a basic solution.

3. The method of claim 2, wherein the basic solution has a pH of about 10.

4. The method of claim 2, wherein the basic solution does not contain a reducing agent or a surfactant.

5. The method of claim 1, wherein the oxidation step is performed without stripping more than, or about, 20% of the fluorescent probe from the target adhered to the solid support.

6. The method of claim 1, wherein the oxidizing agent is selected from hydrogen peroxide, potassium permanganate, sodium dichromate, aqueous bromine, iodine-potassium iodide, and t-butyl hydroperoxide.

7. The method of claim 1, wherein the fluorescent probe comprises a binder and a fluorescent signal generator.

8. The method of claim 7, wherein the fluorescent signal generator comprises a cyanine dye.

9. The method of claim 1, wherein the sample comprises whole cells or tissue sections.

10. The method of claim 1, wherein the sample comprises proteins or nucleic acids.

11. The method of claim 1, wherein steps (d)-(f) are repeated one or more times.

12. The method of claim 1, wherein steps (d)-(f) are repeated at least 5, at least 10, or at least 20 times.

13. The method of claim 1, wherein the oxidation step (d) is performed for less than, or about, 30 minutes.

14. The method of claim 1, wherein the oxidation step (d) is performed for about 30 seconds to about 15 minutes.

15. The method of claim 1, wherein the oxidation step (d) is performed at room temperature.

16. The method of claim 1, further comprising measuring one or more intensity values of the signal observed in observing step (c), step (f), or steps (c) and (f).

17. The method of claim 16, further comprising correlating the intensity value with an amount of target present in the sample.

18. The method of claim 7, wherein the fluorescent signal generator in step (b) is the same as the fluorescent signal generator in step (e).

19. The method of claim 7, wherein the fluorescent signal generator in step (b) is different from the fluorescent signal generator in step (e).

20. The method of claim 1, wherein the signals observed in step (c) and step (f) are both detectable in a single detection channel.

21. The method of claim 1, wherein the signal observed in step (c) or step (f) is independently detectable in different detection channels.

22. A method of probing multiple targets in a biological sample comprising:
   (a) providing a biological sample containing multiple targets adhered to a membrane;
   (b) binding at least one fluorescent probe to one or more targets present in the sample;
   (c) observing a signal from the fluorescent probe bound in step (b);
   (d) oxidizing the bound fluorescent probe with a solution comprising an oxidizing agent that substantially inactivates the fluorescent probe;
   (e) binding at least one fluorescent probe to one or more targets present in the sample of step (d);
   (f) observing a signal from the fluorescent probe bound in step (e).

23. The method of claim 22, wherein the membrane is selected from nylon, agarose, nitrocellulose, and polyvinylidene difluoride.

24. The method of claim 22, further comprising separating the multiple targets by electrophoresis before step (a).

* * * * *